United States Patent
Moses et al.

(10) Patent No.: US 11,260,132 B2
(45) Date of Patent: Mar. 1, 2022

(54) ENGINEERED LIPOSOMES AS CANCER-TARGETED THERAPEUTICS

(71) Applicant: Children's Medical Center Corporation, Boston, MA (US)

(72) Inventors: Marsha A. Moses, Brookline, MA (US); Peng Guo, Boston, MA (US); Jiang Yang, West Lafayette, IN (US); Debra Auguste, Briarcliff Manor, NY (US); Daxing Liu, Stony Brook, NY (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/494,551

(22) PCT Filed: Mar. 16, 2018

(86) PCT No.: PCT/US2018/022865
§ 371 (c)(1),
(2) Date: Sep. 16, 2019

(87) PCT Pub. No.: WO2018/170398
PCT Pub. Date: Sep. 20, 2018

(65) Prior Publication Data
US 2020/0085972 A1   Mar. 19, 2020

Related U.S. Application Data

(60) Provisional application No. 62/472,206, filed on Mar. 16, 2017.

(51) Int. Cl.
*A61K 47/69* (2017.01)
*A61K 47/68* (2017.01)
(Continued)

(52) U.S. Cl.
CPC ........ *A61K 47/6913* (2017.08); *A61K 31/704* (2013.01); *A61K 47/6849* (2017.08);
(Continued)

(58) Field of Classification Search
CPC combination set(s) only.
See application file for complete search history.

(56) References Cited

U.S. PATENT DOCUMENTS

| | | |
|---|---|---|
| 5,284,931 A | 2/1994 | Springer et al. |
| 5,626,870 A | 5/1997 | Minshipouri et al. |

(Continued)

FOREIGN PATENT DOCUMENTS

| | | |
|---|---|---|
| EP | 2468775 A1 | 6/2012 |
| WO | WO 1991/16928 A1 | 11/1991 |

(Continued)

OTHER PUBLICATIONS

Cahall et al., A Quantitative Perspective on Surface Marker Selection for the Isolation of Functional Tumor Cells. Breast Cancer (Auckl). Jul. 27, 2015;9(Suppl 1):1-11.

(Continued)

*Primary Examiner* — Gollamudi S Kishore
(74) *Attorney, Agent, or Firm* — Wolf, Greenfield & Sacks, P.C.

(57) ABSTRACT

The disclosure provides liposomes (e.g., cancer-targeting liposomes) with ligands (e.g., EGFR ligands and ICAM-1 ligands) conjugated to liposome surfaces. In some embodiments, the molecular ratio of different ligands complement the relative molecular density (i.e., ratio) of overexpressed protein on the surface of a cell targeted by the liposome (e.g., cancer cell).

15 Claims, 33 Drawing Sheets

(51) Int. Cl.
  *A61P 35/04* (2006.01)
  *A61P 35/00* (2006.01)
  *A61K 31/704* (2006.01)
  *C07K 16/28* (2006.01)

(52) U.S. Cl.
  CPC ...... *A61K 47/6855* (2017.08); *A61K 47/6915* (2017.08); *A61P 35/00* (2018.01); *A61P 35/04* (2018.01); *C07K 16/2821* (2013.01); *C07K 16/2863* (2013.01)

(56) References Cited

U.S. PATENT DOCUMENTS

| | | | |
|---|---|---|---|
| 6,316,024 | B1 | 11/2001 | Allen et al. |
| 6,569,451 | B1 | 5/2003 | Bednarski et al. |
| 9,737,492 | B2 | 8/2017 | Mao et al. |
| 10,421,758 | B2 * | 9/2019 | Chiosis ............... C07D 519/00 |
| 2002/0071843 | A1 | 6/2002 | Bednarski et al. |
| 2004/0013720 | A1 | 1/2004 | Ellens et al. |
| 2007/0111331 | A1 | 5/2007 | Hong et al. |
| 2007/0280948 | A1 | 12/2007 | Williams et al. |
| 2008/0187595 | A1 | 8/2008 | Jordan et al. |
| 2009/0186078 | A1 | 7/2009 | Kliche et al. |
| 2010/0008978 | A1 | 1/2010 | Drummond et al. |
| 2010/0209490 | A1 * | 8/2010 | Morita ............... C07K 16/2878 424/450 |
| 2010/0285002 | A1 | 11/2010 | Peer et al. |
| 2011/0244048 | A1 | 10/2011 | Amiji et al. |
| 2013/0034548 | A1 | 2/2013 | Moyo et al. |
| 2013/0064763 | A1 | 3/2013 | Abulrob et al. |
| 2014/0127187 | A1 | 5/2014 | Niitsu et al. |
| 2014/0127287 | A1 | 5/2014 | Xiong et al. |
| 2014/0314666 | A1 | 10/2014 | Muro Galindo et al. |
| 2015/0064265 | A1 | 3/2015 | Fahmy et al. |
| 2017/0173005 | A1 | 6/2017 | Auguste et al. |
| 2021/0113466 | A1 | 4/2021 | Moses et al. |

FOREIGN PATENT DOCUMENTS

| | | |
|---|---|---|
| WO | WO 1998/016201 A1 | 4/1998 |
| WO | WO 1998/016202 A1 | 4/1998 |
| WO | WO 02/36073 A2 | 5/2002 |
| WO | WO 2006/116107 A2 | 11/2006 |
| WO | WO 2007/127219 A2 | 11/2007 |
| WO | WO 2007/127221 A2 | 11/2007 |
| WO | WO 2007/127272 A2 | 11/2007 |
| WO | WO 2009/026328 A2 | 2/2009 |
| WO | WO 2012/007516 A1 | 1/2012 |
| WO | WO 2012/106559 A1 | 8/2012 |
| WO | WO 2012/155048 A1 | 11/2012 |
| WO | WO 2014/046630 A1 | 3/2014 |
| WO | WO 2015/066535 A1 | 5/2015 |
| WO | WO 2015/089419 A2 | 6/2015 |
| WO | WO 2015/148971 A2 | 10/2015 |
| WO | WO 2016/064882 A1 | 4/2016 |
| WO | WO 2017/223135 A1 | 12/2017 |

OTHER PUBLICATIONS

Crown et al., Emerging targeted therapies in triple-negative breast cancer. Ann Oncol. Aug. 2012;23 Suppl 6:vi56-65.
Grijalvo et al., Biodegradable liposome-encapsulated hydrogels for biomedical applications: a marriage of convenience. Biomater Sci. Apr. 2016;4(4):555-74.
Gunawan et al., Complementary targeting of liposomes to IL-1α and TNF-α activated endothelial cells via the transient expression of VCAM1 and E-selectin. Biomaterials. Dec. 2011;32(36):9848-53.
Guo et al., ICAM-1 as a molecular target for triple negative breast cancer. Proc Natl Acad Sci U S A. Oct. 14, 2014;111(41):14710-5.
Guo et al., ICAM-1-Targeted, Lcn2 siRNA-Encapsulating Liposomes are Potent Anti-angiogenic Agents for Triple Negative Breast Cancer. Theranostics. Jan. 1, 2016;6(1):1-13.
Guo et al., Inhibiting metastatic breast cancer cell migration via the synergy of targeted, pH-triggered siRNA delivery and chemokine axis blockade. Mol Pharm. Mar. 3, 2014;11(3):755-65.
Guo et al., Abstract 4410: An ICAM-1-targeted, Lcn2 siRNA-encapsulating liposome as a potent anti-angiogenic agent for triple-negative breast cancer. In: Proceedings of the 106th Annual Meeting of the American Association for Cancer Research; Apr. 18-22, 2015; Philadelphia, PA. Philadelphia (PA): AACR; Cancer Res 2015;75(15 Suppl):Abstract nr 4410.
Hendriks et al., Impact of tumor HER2/ERBB2 expression level on HER2-targeted liposomal doxorubicin-mediated drug delivery: multiple low-affinity interactions lead to a threshold effect. Mol Cancer Ther. Sep. 2013;12(9):1816-28.
Yu et al., Improved delivery of Cas9 protein/gRNA complexes using lipofectamine CRISPRMAX. Biotechnol Lett. Jun. 2016;38(6):919-29.
U.S. Appl. No. 16/494,568, filed Sep. 16, 2019, Moses et al.
PCT/US2018/022865, Jun. 6, 2018, International Search Report and Written Opinion.
PCT/US2018/022865, Sep. 26, 2019, International Preliminary Report on Patentability.
PCT/US2018/022890, Jul. 16, 2018, International Search Report and Written Opinion.
PCT/US2018/022890, Sep. 26, 2019, International Preliminary Report on Patentability.
Dan et al., Binding, transcytosis and biodistribution of anti-PECAM-1 iron oxide nanoparticles for brain-targeted delivery. PLoS One. 2013;8(11):e81051. Published Nov. 20, 2013.
Huang et al., Casein-coated iron oxide nanoparticles for high MRI contrast enhancement and efficient cell targeting. ACS Appl Mater Interfaces. 2013;5(11):4632-4639.
Liu et al., Self-assembled nanoparticles based on a carboxymethylcellulose-ursolic acid conjugate for anticancer combination therapy. RSC Advances. 2017;7:36256.
Mauro et al., ICAM-1 expression and the soluble ICAM-1 level for evaluating the metastatic potential of gastric cancer. Int J Cancer. 2002;100(4):486-490.
Morral-Ruiz et al., Multifunctional polyurethane-urea nanoparticles to target and arrest inflamed vascular environment: a potential tool for cancer therapy and diagnosis. J Control Release. 2013;171(2):163-171.
Muro et al., Slow intracellular trafficking of catalase nanoparticles targeted to ICAM-1 protects endothelial cells from oxidative stress. Am J Physiol Cell Physiol. 2003;285(5):C1339-C1347.
Papademetriou et al., Comparative binding, endocytosis, and biodistribution of antibodies and antibody-coated carriers for targeted delivery of lysosomal enzymes to ICAM-1 versus transferrin receptor. J Inherit Metab Dis. 2013;36(3):467-477. doi:10.1007/s10545-012-9534-6.
Rosette et al., Role of ICAM1 in invasion of human breast cancer cells. Carcinogenesis. 2005;26(5):943-950.
Xu et al., Antibody conjugated magnetic iron oxide nanoparticles for cancer cell separation in fresh whole blood. Biomaterials. 2011;32(36):9758-9765.
Zhang et al., Delivery of ursolic acid (UA) in polymeric nanoparticles effectively promotes the apoptosis of gastric cancer cells through enhanced inhibition of cyclooxygenase 2 (COX-2). Int J Pharm. 2013;441(1-2):261-268.
[No Author Listed]Enlimomab Acute Stroke Trial Investigators. Use of anti-ICAM-1 therapy in ischemic stroke: results of the Enlimomab Acute Stroke Trial. Neurology. Oct. 23, 2001;57(8):1428-34.
Carter et al., Antibody-drug conjugates for cancer therapy. Cancer J. May-Jun. 2008;14(3):154-69.
Chen, Small-molecule delivery by nanoparticles for anticancer therapy. Trends Mol Med. Dec. 2010;16(12):594-602.
Chittasupho et al., ICAM-1 targeting of doxorubicin-loaded PLGA nanoparticles to lung epithelial cells. Eur J Pharm Sci. May 12, 2009;37(2):141-50.
Ducry et al., Antibody-drug conjugates: linking cytotoxic payloads to monoclonal antibodies. Bioconjug Chem. Jan. 2010;21(1):5-13.

(56) References Cited

OTHER PUBLICATIONS

Mastrobattista et al., Cellular uptake of liposomes targeted to intercellular adhesion molecule-1 (ICAM-1) on bronchial epithelial cells. Biochim Biophys Acta. Jul. 15, 1999;1419(2):353-63.
Senter, Potent antibody drug conjugates for cancer therapy. Curr Opin Chem Biol. Jun. 2009;13(3):235-44.
Sughrue et al., Anti-adhesion molecule strategies as potential neuroprotective agents in cerebral ischemia: a critical review of the literature. Inflamm Res. Oct. 2004;53(10):497-508.
Taniguchi et al., Effects of the anti-ICAM-1 monoclonal antibody on dextran sodium sulphate-induced colitis in rats. J Gastroenterol Hepatol. Sep. 1998;13(9):945-9.
Villanueva et al., Microbubbles targeted to intercellular adhesion molecule-1 bind to activated coronary artery endothelial cells. Circulation. Jul. 7, 1998;98(1):1-5.
Zhang et al., Anti-ICAM-1 antibody reduces ischemic cell damage after transient middle cerebral artery occlusion in the rat. Neurology. Sep. 1994;44(9):1747-51.
Zhang et al., PLGA nanoparticle—peptide conjugate effectively targets intercellular cell-adhesion molecule-1. Bioconjug Chem. Jan. 2008;19(1):145-52.
Manikwar et al., Utilization of I-domain of LFA-1 to Target Drug and Marker Molecules to Leukocytes. Theranostics. 2011;1:277-89. doi: 10.7150/thno/v01p0277. Epub May 10, 2011.
Muro et al., Control of intracellular trafficking of ICAM-1-targeted nanocarriers by endothelial Na+/H+ exchanger proteins. Am J Physiol Lung Cell Mol Physiol. May 2006;290(5):L809-17. doi: 10.1152/ajplung.00311.2005. Epub Nov. 18, 2005.
Muro et al., Lysosomal enzyme delivery by ICAM-1-targeted nanocarriers bypassing glycosylation- and clathrin-dependent endocytosis. Mol Ther. Jan. 2006;13(1):135-41. doi: 10.1016/j.ymthe.2005.07.687. Epub Sep. 8, 2005.
Murphy et al., Targeted nanogels: a versatile platform for drug delivery to tumors. Mol Cancer Ther. Jun. 2011;10(6):972-82. doi: 10.1158/1535-7163.MCT-10-0729. Epub Apr. 25, 2011.
Park et al., Characterization of radioligand binding to a transmembrane receptor reconstituted into Lipobeads. FEBS Lett. Jun. 4, 2004;567(2-3):344-8. doi: 10.1016/j.febslet.2004.03.124.
Wang et al., In Vivo Delivery Systems for Therapeutic Genome Editing. Int J Mol Sci. Apr. 27, 2016;17(5):626. doi: 10.3390/ijms17050626.
EP 18767619.2, Dec. 14, 2020, Extended European Search Report.
EP 18768321.4, Dec. 7, 2020, Extended European Search Report.
PCT/US2015/023078, Dec. 30, 2015, International Search Report and Written Opinion.
Chen et al., Targeted Delivery of CRISPR/Cas9-Mediated Cancer Gene Therapy via Liposome-Templated Hydrogel Nanoparticles. Adv Funct Mater. Dec. 8, 2017;27(46):1703036.
Ding et al., A non-cationic nucleic acid nanogel for the delivery of the CRISPR/Cas9 gene editing tool. Nanoscale. Oct. 7, 2019;11(37):17211-17215.
Pannier et al., Surface- and hydrogel-mediated delivery of nucleic acid nanoparticles. Methods Mol Biol. 2013;948:149-69.

\* cited by examiner

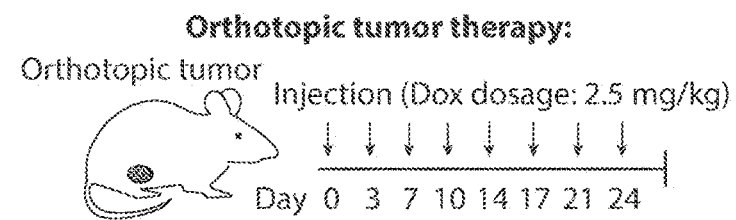
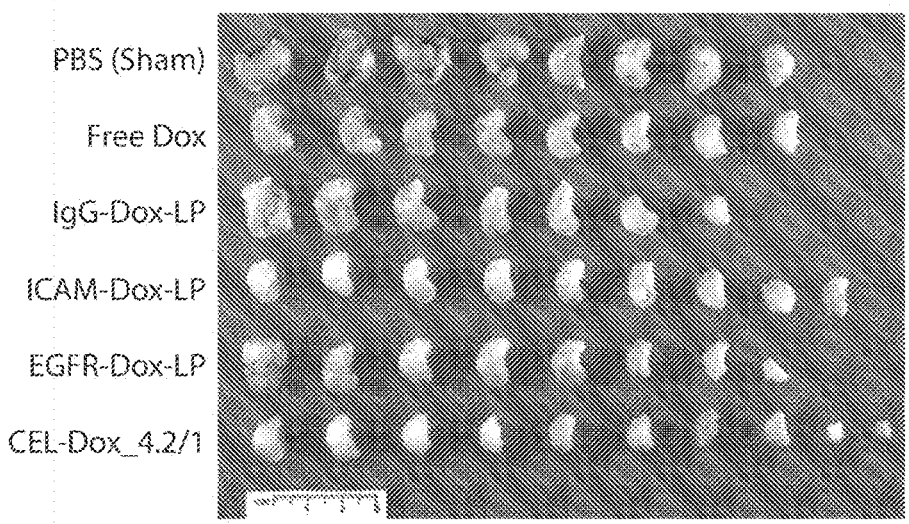
Figure 9A
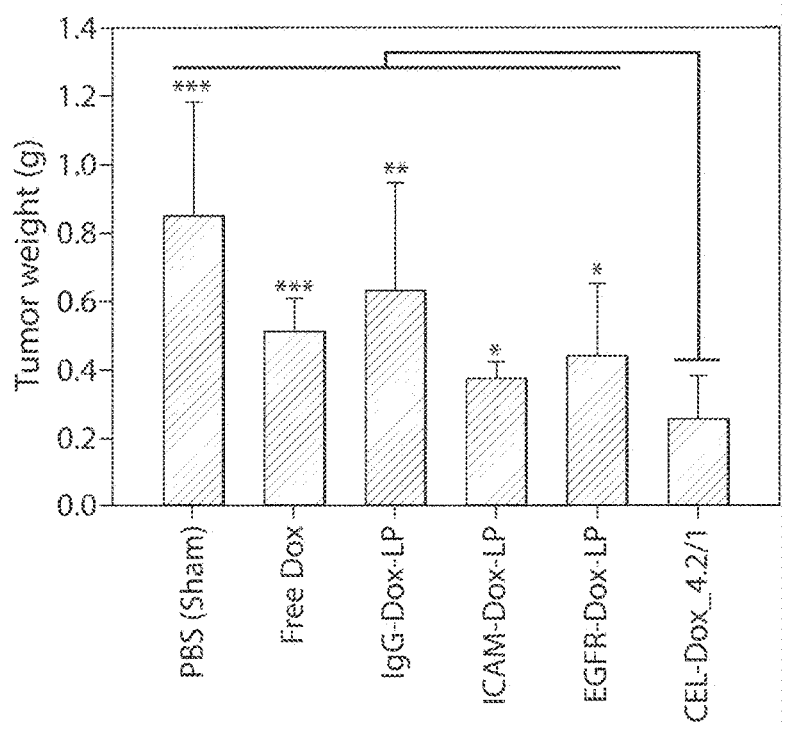
Figure 9B

| | Brain | Heart | Lung | Liver | Spleen | Kidney | Tumor bearing right hind limb | Normal left hind limb | Total |
|---|---|---|---|---|---|---|---|---|---|
| PBS | 0% (0/8) | 0% (0/8) | 12.5% (1/8) | 37.5% (3/8) | 37.5% (3/8) | 0% (0/8) | 75% (6/8) | 12.5% (1/8) | 87.5% (7/8) |
| Free Dox | 0% (0/8) | 0% (0/8) | 0% (0/8) | 0% (0/8) | 0% (0/8) | 0% (0/8) | 100% (8/8) | 0% (0/8) | 100% (8/8) |
| IgG-Dox-LP | 0% (0/8) | 0% (0/8) | 0% (0/8) | 25% (2/8) | 25% (2/8) | 0% (0/8) | 62.5% (5/8) | 0% (0/8) | 75% (6/8) |
| ICAM-Dox-LP | 0% (0/9) | 0% (0/9) | 0% (0/9) | 0% (0/9) | 11.1% (1/9) | 0% (0/8) | 44.4% (4/9) | 22.2% (2/9) | 55.6% (5/9) |
| EGFR-Dox-LP | 0% (0/8) | 0% (0/8) | 12.5% (1/8) | 12.5% (1/8) | 12.5% (1/8) | 0% (0/8) | 62.5% (5/8) | 12.5% (1/8) | 62.5% (5/8) |
| CEL-Dox_4.2/1 | 0% (0/10) | 0% (0/10) | 0% (0/10) | 0% (0/10) | 10% (1/10) | 0% (0/10) | 10% (1/10) | 0% (0/10) | 10% (1/10) |

Figure 9E

| Metastatic site | PBS(sham) | Free Dox | IgG-Dox-LP | ICAM-Dox-LP | EGFR-Dox-LP | CTL-Dox_4.2/1 |
|---|---|---|---|---|---|---|
| Orthotopic Breast Tumor Model | | | | | | |
| Brain | 0/8 | 0/8 | 0/7 | 0/9 | 0/8 | 0/10 |
| Lung | 1/8 | 0/8 | 0/7 | 0/9 | 1/8 | 0/10 |
| Heart | 0/8 | 0/8 | 0/7 | 0/9 | 0/8 | 0/10 |
| Liver | 3/8 | 0/8 | 2/7 | 0/9 | 1/8 | 0/10 |
| Spleen | 3/8 | 0/8 | 2/7 | 1/9 | 1/8 | 1/10 |
| Kidney | 0/8 | 0/8 | 0/7 | 0/9 | 0/8 | 0/10 |
| Right hind limb (tumor bearing) | 6/8 | 8/8 | 5/7 | 4/9 | 5/8 | 1/10 |
| Left hind limb (normal) | 1/8 | 0/8 | 0/7 | 2/9 | 1/8 | 0/10 |
| Total | 7/8 | 8/8 | 6/7 | 5/9 | 5/8 | 1/10 |
| Lung Metastasis Model | | | | | | |
| Brain | 0/8 | 0/8 | 0/8 | 0/8 | 0/8 | 0/8 |
| Lung | 8/8 | 5/8 | 6/8 | 2/8 | 6/8 | 0/8 |
| Heart | 0/8 | 0/8 | 0/8 | 0/8 | 0/8 | 0/8 |
| Liver | 2/8 | 0/8 | 1/8 | 0/8 | 0/8 | 0/8 |
| Spleen | 1/8 | 0/8 | 0/8 | 0/8 | 0/8 | 0/8 |
| Kidney | 0/8 | 0/8 | 0/8 | 0/8 | 0/8 | 0/8 |
| Hind limbs (normal) | 0/8 | 0/8 | 0/8 | 0/8 | 0/8 | 0/8 |
| Total | 8/8 | 5/8 | 6/8 | 2/8 | 6/8 | 0/8 |

Figure 12

ENGINEERED LIPOSOMES AS CANCER-TARGETED THERAPEUTICS

RELATED APPLICATIONS

This application is a national stage filing under 35 U.S.C. § 371 of international PCT application, PCT/US2018/022865 filed Mar. 16, 2018, which claims the benefit of the filing under 35 U.S.C. § 119(e) to U.S. provisional patent application, U.S. Ser. No. 62/472,206 filed Mar. 16, 2017, the entire contents of each of which are incorporated herein by reference.

GOVERNMENT SUPPORT

This invention was made with government support under grants R01CA185530 and 1DP2CA174495 awarded by the National Institutes of Health. The government has certain rights in the invention.

BACKGROUND

Liposomes have been widely used as delivery vehicles for anti-cancer drugs (e.g., a chemotherapeutic drug) for the treatment of cancer. A major challenge in cancer treatment is discriminating malignant cancer cells from normal (e.g., non-neoplastic) cells. "Cancer-targeting" liposomes have been engineered to facilitate the specific recognition of cancer. Nonetheless, previous targeted cancer therapeutics have limited success due to "off-target" effects.

SUMMARY

Provided herein, in some aspects, are multi-targeting (e.g., dual-targeting) liposomes for cancer (e.g., triple negative breast cancer or TNBC) treatment. The expression level of cell surface proteins on cancer cells (e.g., TNBC) are quantified and overexpressed proteins (e.g., EGFR and ICAM-1) are identified as targets for cancer treatment. Complementary engineered liposomes (CELs, also termed herein as "dual complementary liposomes" or "DCLs") that can selectively recognize and complement the molecular density (i.e., ratio) of overexpressed cancer cell surface proteins on cancer cell surface are developed, facilitating targeted delivery of the chemotherapeutic drugs (e.g., doxorubicin). Further, the CELs simultaneously neutralized the signaling cascades triggered by cancer cell surface proteins (e.g., ICAM-1 and EGFR), resulting in significant and synergistic inhibition effects in cancer cell invasion and proliferation. The compositions and methods described herein provide promising personalized therapeutic strategies for cancer (e.g., TNBC) therapy.

Some aspects of the present disclosure provide liposomes containing: (i) a lipid bilayer; (ii) an EGFR ligand conjugated to the liposome surface; (iii) an ICAM-1 ligand conjugated to the liposome surface; and (iv) a therapeutic agent encapsulated in the liposome.

In some embodiments, the lipid bilayer comprises a neutral lipid. In some embodiments, the neutral lipid is 1,2-dioleoyl-sn-glycero-3-phosphocholine (DOPC). In some embodiments, the lipid bilayer comprises an anionic lipid. In some embodiments, the lipid bilayer further comprises a functionalized lipid. In some embodiments, the functionalized lipid is a lipid-polymer conjugate. In some embodiments, the lipid-polymer conjugate is a lipid-polyethylene glycol (PEG) conjugate. In some embodiments, the functionalized lipid comprises a reactive group at the distal end of the lipid. In some embodiments, the functionalized lipid is 1,2-distearoyl-sn-glycero-3-phosphoethanolamine-N-[carboxy(polyethylene glycol)-2000]-COOH (DSPE-PEG-COOH).

In some embodiments, the functionalized lipid is up to 10% of total lipids in the liposome.

In some embodiments, the EGFR ligand or the ICAM-1 ligand is conjugated to the functionalized lipid.

In some embodiments, the lipid bilayer further comprises a pH-responsive lipid. In some embodiments, the pH-responsive lipid comprises 1,2-dioleoyl-3-dimethylammonium-propane (DODAP).

In some embodiments, the EGFR ligand is selected from the group consisting of: antibodies, antibody fragments, synthetic peptides, natural ligands, aptamers. In some embodiments, the EGFR ligand is an EGFR antibody.

In some embodiments, the ICAM-1 ligand is selected from the group consisting of: antibodies, antibody fragments, synthetic peptides, natural ligands, and aptamers. In some embodiments, the ICAM-1 ligand is an ICAM-1 antibody.

In some embodiments, a ratio of ICAM-1 ligand:EGFR ligand is between 0.01-10. In some embodiments, the ratio of ICAM-1 ligand:EGFR ligand is 1.5. In some embodiments, the ratio of ICAM-1 ligand:EGFR ligand is 4.2.

In some embodiments, the therapeutic agent is an anti-cancer agent. In some embodiments, the therapeutic agent is selected from the group consisting of: small molecules, oligonucleotides, polypeptides, and combinations thereof. In some embodiments, the therapeutic agent is a chemotherapeutic agent. In some embodiments, the chemotherapeutic agent is selected from the group consisting of: Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. In some embodiments, the chemotherapeutic agent is Doxorubicin.

Also provided herein are pharmaceutical compositions containing the liposomes described herein. In some embodiments, the pharmaceutical composition further contains a pharmaceutically acceptable carrier.

Other aspects of the present disclosure provide liposome drug delivery systems containing: (i) a lipid bilayer; (ii) a plurality of ligands conjugated to the liposome surface, wherein each ligand targets a different surface protein of a cell, and wherein the ratio of the plurality of ligands complements the ratio of targeted surface proteins; and (iii) a therapeutic agent encapsulated in the liposome. In some embodiments, the plurality of ligands target 2-10 different surface proteins of the cell.

Other aspects of the present disclosure provide methods of treating triple negative breast cancer (TNBC), the method includes administering to a subject in need thereof a therapeutically effective amount of a liposome containing: (i) a lipid bilayer; (ii) an EGFR ligand conjugated to the liposome surface; (iii) an ICAM-1 ligand conjugated to the liposome surface; and (iv) a therapeutic agent encapsulated in the liposome.

In some embodiments, the lipid bilayer comprises a neutral lipid. In some embodiments, the neutral lipid is 1,2-dioleoyl-sn-glycero-3-phosphocholine (DOPC). In some embodiments, the lipid bilayer comprises an anionic lipid. In some embodiments, the lipid bilayer further comprises a functionalized lipid. In some embodiments, the functionalized lipid is a lipid-polymer conjugate. In some embodiments, the lipid-polymer conjugate is a lipid-polyethylene glycol (PEG) conjugate. In some embodiments, the functionalized lipid comprises a carboxylic acid at the distal end of the lipid. In some embodiments, the functionalized lipid is 1,2-distearoyl-sn-glycero-3-phosphoethanolamine-N-[carboxy(polyethylene glycol)-2000]-COOH (DSPE-PEG-COOH). In some embodiments, the functionalized lipid is up to 10% of total lipids in the liposome.

In some embodiments, the EGFR ligand or the ICAM-1 ligand is conjugated to the functionalized lipid.

In some embodiments, the lipid bilayer further comprises a pH-responsive lipid. In some embodiments, the pH-responsive lipid comprises 1,2-dioleoyl-3-dimethylammoniumpropane (DODAP).

In some embodiments, the EGFR ligand is selected from the group consisting of: antibodies, antibodies fragments, synthetic peptides, natural ligands, aptamers. In some embodiments, the EGFR ligand is an EGFR antibody. In some embodiments, the ICAM-1 ligand is selected from the group consisting of: antibodies, antibodies fragments, synthetic peptides, natural ligands, and aptamers.

In some embodiments, the ICAM-1 ligand is an ICAM-1 antibody. In some embodiments, the ratio of ICAM-1 ligand: EGFR ligand is between 0.01-10. In some embodiments, the ratio of ICAM-1 ligand:EGFR ligand is 1.5. In some embodiments, the ratio of ICAM-1 ligand:EGFR ligand is 4.2.

In some embodiments, the therapeutic agent is an anticancer agent. In some embodiments, the therapeutic agent is selected from the group consisting of: small molecules, oligonucleotides, polypeptides, and combinations thereof. In some embodiments, the therapeutic agent is a chemotherapeutic agent. In some embodiments, the chemotherapeutic agent is selected from the group consisting of: Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. In some embodiments, the chemotherapeutic agent is Doxorubicin.

In some embodiments, the liposome is administered orally, parenterally, intramuscularly, intranasally, intratracheal, intracerebroventricularly, intravenously, or intraperitoneally.

In some embodiments, the liposome binds to TNBC cells. In some embodiments, the liposome binds to TNBC cells via binding to EGFR and/or ICAM-1 on TNBC surface. In some embodiments, the binding of the liposome to EGFR or ICAM-1 on TNBC surface inhibits EGFR or ICAM-1 signaling pathway in TNBC cells. In some embodiments, binding of the liposome to EGFR or ICAM-1 on TNBC surface inhibits TNBC proliferation. In some embodiments, the liposome does not bind to normal cells.

In some embodiments, the liposome delivers the therapeutic agent to TNBC cells. In some embodiments, the therapeutic agent kills TNBC cells.

Further provided herein are methods of making a cancer cell targeting liposome, the method includes: (i) determining a ratio of a plurality of cancer-specific cell surface proteins; and (ii) conjugating ligands targeting the plurality of cancer-specific cell surface proteins to the surface of a liposome, wherein the ratio of the ligands on the liposome surface complements the ratio of the plurality of cancer-specific cell surface proteins. Liposomes produced by the methods described are also provided. Such liposomes may be administered to a subject in need thereof in a therapeutically effective amount to treat cancer. In some embodiments, the cancer is selected from the group consisting of: lung cancer, breast cancer, prostate cancer, colorectal cancer, gastric cancer, liver cancer, pancreatic cancer, brain and central nervous system cancer, skin cancer, ovarian cancer, leukemia, endometrial cancers, bone, cartilage and soft tissue sarcomas, lymphoma, neuroblastoma, nephroblastoma, retinoblastoma, and gonadal germ cell tumors.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. The patent or application file contains at least one drawing executed in color. Copies of this patent or patent application publication with color drawing(s) will be provided by the Office upon request and payment of the necessary fee. In the drawings:

DCL improve therapeutic efficacy using synergistic blockade of ICAM1 and EGFR signaling cascades.

(FIG. 5A) Representative microscope images demonstrating that human TNBC MDA-MB-231 and MDA-MB-436 cell invasion evaluated by transwell invasion assay after incubation with PBS (control), non-specific IgG-LP, ICAM-1-LP, EGFR-LP, and CELs at optimal ICAM-1/EGFR antibody ratios (4.2/1 for MDA-MB-231 cells, 1.5/1 for MDA-MB-436 cells). All scale bars are 50 µm. Quantitative analysis of TNBC cell invasion inhibited by CELs: (FIG. 5B) MDA-MB-231 and (FIG. 5C) MDA-MB-436 cells is also shown. (FIG. 5D) In vitro cellular binding and uptake of DCL-FITC and controls in human TNBC and MCF10A cells were determined by flow cytometry in reference to IgG-FITC-LP. (FIG. 5E) Representative fluorescent images showing TNBC-specific cellular binding and uptake of DCL-FITCs in TNBC and MCF10A cells in comparison with IgG-FITC-LP, ICAM-FITC-LP, and EGFR-FITC-LP. Scale bars represent 20 µm. (FIG. 5F) Internalization ratios of DCL-FITC and controls were determined by Trypan Blue quenching assay. (FIG. 5G) Quantified analysis of therapeutic efficacies of DCL (vehicle without Dox) and controls on TNBC cell proliferation. (FIG. 5H) In vitro cytotoxicity of DCL-Dox was evaluated for MDA-MB-231 and MDA-MB-436 cells by Dojindo cell viability assay in reference to DCL (vehicle without Dox). NS, not significant; * $P<0.05$;  $P<0.01$; * $P<0.001$.

(FIG. 8A) Schematic design of orthotopic tumor biodistribution imaging and representative in vivo NIR images of MDA-MB-231 bearing nude mice 4 h, 24 h, and 48 h after injection of IgG-DiR-LP, ICAM-DiR-LP, EGFR-DiR-LP, and CEL-DiR_4.2/1 (n=8 for each group). (FIG. 8B) Quantified fluorescence intensities of in vivo tumor accumulation of IgG-DiR-LP, ICAM-DiR-LP, EGFR-DiR-LP, and CEL-DiR_4.2/1. Six mice were measured per group. * $p<0.05$, * $p<0.001$. (FIG. 8C) Ex vivo NIR fluorescent images of tumors and organs (liver, spleen, lung, kidney, heart, and brain) after 48 h circulation in the body. (FIG. 8D**) Biodistribution of immunoliposome formulations quantified by its fluorescent intensity. (NS non-significant, * $p<0.05$; * $p<0.001$). (FIG. 8E) Quantitative analysis of in vivo tumor accumulation of DCL-DiR_4.2/1 and control liposomes. (FIG. 8F**) Representative ex vivo NIR fluorescent images of organs (liver, spleen, kidney, lung, heart and brain) and excised tumors.

FIGS. 9A-9E show the in vivo therapeutic effect of CEL-Dox_4.2/1. (FIG. 9A) Schematic design of orthotopic tumor therapy model and representative images of TNBC tumors treated with PBS (sham), free Dox, IgG-Dox-LP, ICAM-Dox-LP, EGFR-Dox-LP, or CEL-Dox_4.2/1 (2.5 mg/kg per dose) on day 24. Tumor mass (FIG. 9B) in each group (n=6-9) was quantified. Mouse tumor volume (FIG. 9C) and body weight (FIG. 9D) were monitored during the treatment. (NS, not significant, * $p<0.05$; * $p<0.001$). (FIG. 9E**) Tumor metastasis on different organs determined by IVIS imaging.

(FIG. 10A) Surface protein expression of 68 cancer targets in three human TNBC cell lines and nonneoplastic MCF10A cells. Red and green bars represent maximum and minimum expression, respectively. (FIG. 10B) Summary of surface protein expression analysis. 16 cancer targets were identified as upregulated in all three TNBC cell lines compared to MCF10A cells. (FIG. 10C) Quantified surface densities of 16 target candidates. Red bars represent the 5 top candidates that were overexpressed in TNBC cells. (FIG. 10D) ICAM1 and EGFR gene expression in human TNBC and MCF10A cells as quantified by qRT-PCR. * $P<0.001$. (FIG. 10E) Representative microscopic images of immunofluorescent staining of ICAM1 and EGFR in three human TNBC cell lines and MCF10A cells. Scale bars represent 20 µm. (FIG. 10F) FRET analysis of ICAM1 and EGFR colocalization. NS, not significant;  $P<0.01$. (FIG. 10G) Correlation between overall survival and ICAM1/EGFR mRNA expression levels in basal-like breast cancer patients as shown with Kaplan-Meier analysis (NS, not significant; * $P<0.05$, log-rank test).

(FIG. 11A) Schematic design of TNBC lung metastasis therapy (upper panel) and representative bioluminescence images of lung metastasis at different time points in mice treated with the following agents (lower panel): PBS (sham), free Dox, IgG-Dox-LP, ICAM-Dox-LP, EGFR-Dox-LP, or DCL-Dox_4.2/1 (n=8 for each group). (FIG. 11B) Representative tumor progression curves as depicted from in vivo bioluminescence signal intensity (n=3 for each group). (FIG. 11C) Size and morphology of lungs excised from mice in different treatment groups. (FIG. 11D) Quantification of metastasis node numbers on excised lungs from mice indifferent treatment groups. (FIG. 11E) Metastasis-free survival of mice in DCL-Dox and control groups as displayed by Kaplan-Meier curves (log-rank test). NS, not significant;  $P<0.01$; * $P<0.001$. (FIG. 11F) Schematic design for dosage-dependent therapy (upper panel) and in vivo bioluminescence images of mice in the dosage-dependent study (lower panel). Tumor-bearing mice were treated with DCL-Dox_4.2/1 at different dosages and imaged at day 74 or an earlier sacrifice date (n=5 for each group. * indicates the mouse sacrificed at day 22 due to blindness caused by retro-orbital injection). (FIG. 11G) Quantification of metastasis node numbers on excised lungs in the dosage-dependent study. (FIG. 11H) Metastasis-free survival of mice in the dosage-dependent study as displayed by Kaplan-Meier curves (log-rank test).* $P<0.05$. (FIG. 11I) Serum levels of AST, ALT, Creatinine, and BUN (n=4-5 per group). NS, not significant, * $P<0.05$;  $P<0.01$; * $P<0.001$.

FIG. 12 is a summary of metastasis formation in TNBC orthotopic and lung metastasis models.

(FIG. 13B) Hydrodynamic radius of DCLs as analyzed by dynamic light scattering measurement.

DETAILED DESCRIPTION OF CERTAIN EMBODIMENTS

Figure 1:
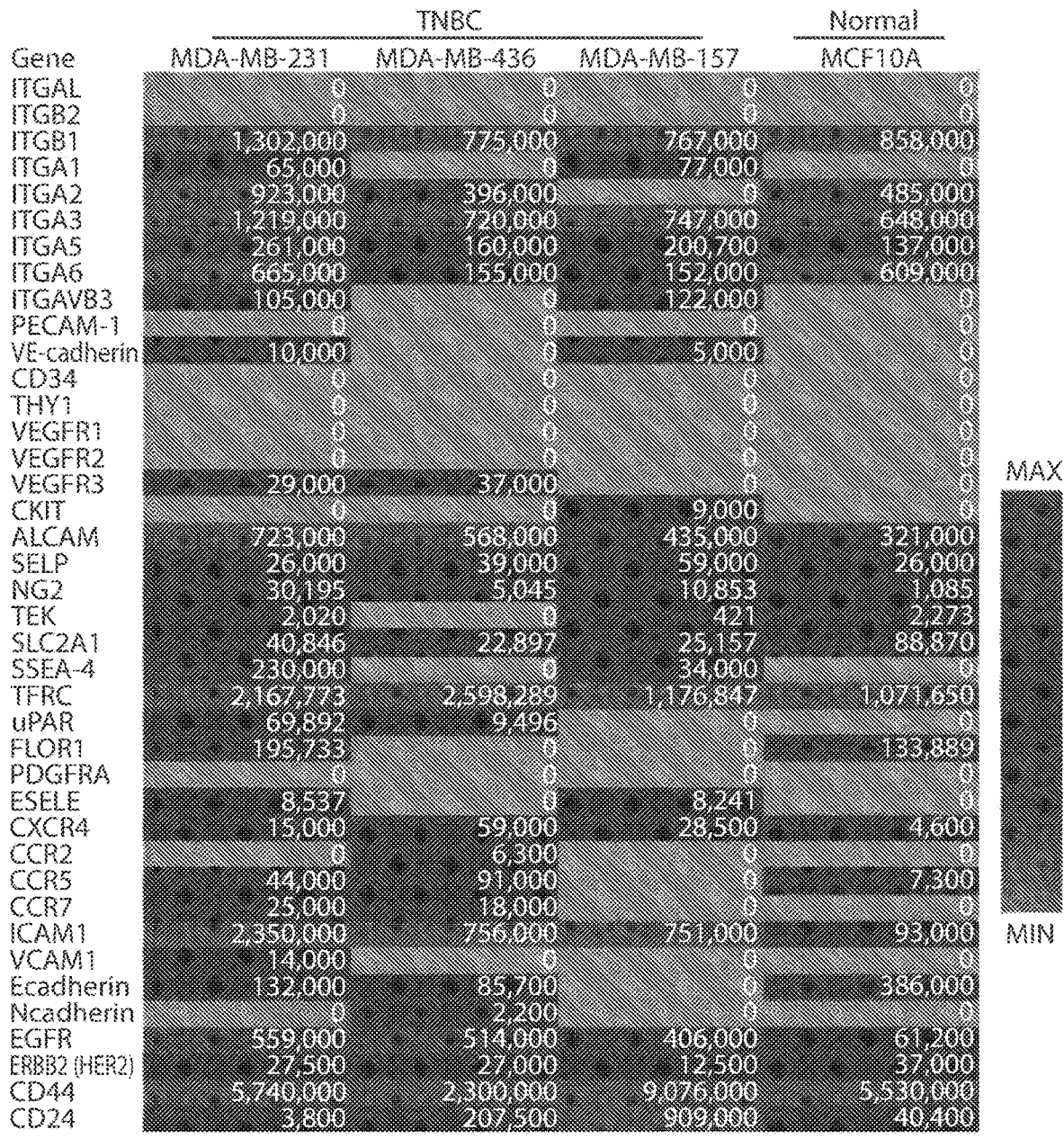
FIG. 1 shows the identification of ICAM-1 and EGFR as TNBC optimized target combination. The surface density of 40 cell membrane proteins was quantified via flow cytometry analysis in MDA-MB-231, MDA-MB-436, and MCF10A cells.

Provided herein are multi-targeting (e.g., dual-targeting) liposomes for cancer (e.g., triple negative breast cancer or TNBC) treatment. The expression level of cell surface proteins on cancer cells (e.g., TNBC) are measured and overexpressed proteins (e.g., EGFR and ICAM-1) are identified as targets for cancer treatment. In some embodiments, the liposomes are complementary engineered liposomes (CELs, also termed interchangeably herein as "dual complementary liposomes" or "DCLs")) that can selectively recognize and complement the molecular density of overexpressed cancer cell surface proteins (e.g., ICAM-1 and EGFR) on TNBC cell membranes are developed, facilitating targeted delivery of the chemotherapeutic drugs (e.g., doxorubicin). Further, the CELs simultaneously neutralized the signaling cascades triggered by cancer cell surface proteins (e.g., ICAM-1 and EGFR), resulting in significant and synergistic inhibition effects in cancer cell invasion and proliferation. The compositions and methods described herein provide promising personalized therapeutic strategies for cancer (e.g., TNBC) therapy.

Some aspects of the present disclosure provide liposomes with multiple ligands (e.g., 2, 3, 4, 5, or more ligands) conjugated to their surfaces. In some embodiments, the liposomes contain encapsulated therapeutic agents (e.g., anti-cancer drugs). The ligands specifically target surface proteins that overexpress on certain cell types (e.g., cancer cells) compare to other cell types (e.g., normal, non-neoplastic cells).

A "liposome" is a microscopic vesicle having at least one concentric lipid bilayers. In some embodiments, a liposome has one lipid bilayer. Structurally, liposomes range in size and shape from long tubes to spheres, with dimensions from a few hundred Angstroms to fractions of a millimeter. In some embodiments, the liposome is a sphere. Typically, liposomes can be divided into three categories based on their overall size and the nature of the lamellar structure. The three classifications, as developed by the New York Academy Sciences Meeting (Liposomes and Their Use in Biology and Medicine, December 1977, incorporated herein by reference), are multi-lamellar vesicles (MLVs), small uni-lamellar vesicles (SUVs) and large uni-lamellar vesicles (LUVs). SUVs range in diameter from approximately 20 to 100 nm and consist of a single lipid bilayer surrounding an aqueous compartment. Large unilamellar vesicles can also be prepared in sizes from about 100 nm to a few micrometers (e.g., 30 μm) in diameter. While unilamellar vesicles are single compartmental vesicles of fairly uniform size, MLVs vary greatly in size up to 10,000 nm, are multi-compartmental in their structure and contain more than one bilayer. The liposomes of the present disclosure are unilamellar vesicles. Unilamella Liposomes comprise a completely closed lipid bilayer with an encapsulated aqueous volume.

Liposomes have typically been prepared using the process of Bangham et al., (1965 J. Mol. Biol., 13: 238-252), whereby lipids suspended in organic solvent are evaporated under reduced pressure to a dry film in a reaction vessel. An appropriate amount of aqueous phase is then added to the vessel and the mixture agitated. The mixture is then allowed to stand, essentially undisturbed for a time sufficient for the multilamellar vesicles to form. The aqueous phase entrapped within the liposomes may contain bioactive agents, for example drugs, hormones, proteins, dyes, vitamins, or imaging agents, among others.

Liposomes may be reproducibly prepared using a number of currently available techniques. The types of liposomes which may be produced using a number of these techniques include small unilamellar vesicles (SUVs) (e.g., as described in Papahadjapoulous and Miller, Biochem. Biophys. Acta., 135, p. 624-638 (1967), incorporated herein by reference), reverse-phase evaporation vesicles (REV) (e.g., U.S. Pat. No. 4,235,871 issued Nov. 25, 1980, incorporated herein by reference), stable plurilamellar vesicles (SPLV) (e.g., U.S. Pat. No. 4,522,803, issued Jun. 11, 1985, incorporated herein by reference), and large unilamellar vesicles produced by an extrusion technique (e.g., as described in U.S. patent application Ser. No. 622,690, filed Jun. 20, 1984, Cullis et. al., entitled "Extrusion Technique for Producing Unilamellar Vesicles", incorporated herein by reference).

A "lipid bilayer" is a structure composed of two layers of lipid molecules organized in two sheets. Biological bilayers are usually composed of amphiphilic phospholipids that have a hydrophilic phosphate head and a hydrophobic tail consisting of two fatty acid chains. Phospholipids are a class of lipids that are a major component of all cell membranes. They can form lipid bilayers because of their amphiphilic characteristic. The structure of the phospholipid molecule generally consists of two hydrophobic fatty acid "tails" and a hydrophilic "head" consisting of a phosphate group. The two components are joined together by a glycerol molecule. The phosphate groups can be modified with simple organic molecules such as choline.

When phospholipids are exposed to water, they self-assemble into a two-layered sheet with the hydrophobic tails pointing toward the center of the sheet, resulting in two "leaflets" that are each a single molecular layer. The center of this bilayer contains almost no water and excludes molecules like sugars or salts that dissolve in water. The assembly process is driven by interactions between hydrophobic molecules (also called the hydrophobic effect). An increase in interactions between hydrophobic molecules (causing clustering of hydrophobic regions) allows water molecules to bond more freely with each other, increasing the entropy of the system. This complex process includes non-covalent interactions such as van der Waals forces, electrostatic and hydrogen bonds. Phospholipids with certain head groups can alter the surface chemistry of a bilayer and can, for example, serve as signals as well as "anchors" for other molecules in the membranes of cells.

The lipid bilayer of a liposome typical contains vesicle-forming lipids. The specified degree of fluidity or rigidity of the final liposome complex depends on the lipid composition of the outer layer. In some embodiments, lipids in the lipid bilayers of liposomes are neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components include, without limitation phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimidomethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol and (DOPG), dicetylphosphate that are able to form vesicles.

In some embodiments, the lipid bilayer of the liposome described herein comprises a neutral lipid. A "neutral lipid" is a lipid molecule (e.g., a phospholipid molecule) lacking charged groups or having an overall neutral charge. Neutral lipids that may be used in accordance with the present disclosure include, without limitation: dioleoylphosphatidylcholine, dioleoylphosphatidylethanolamine, dilinoleoylphosphatidylcholine, distearoylphophatidylethanolamine, distearoylphosphatidylcholine, dipalmitoylphosphatidylcholine, dipalmitoyl phosphatidylethanolamine, egg phosphatidylcholine, dilauryloylphosphatidylcholine, dimyristoylphosphatidylcholine, 1-myristoyl-2-palmitoyl phosphatidylcholine, 1-palmitoyl-2-myristoyl phosphatidylcholine, 1-palmitoyl-2-stearoyl phosphatidylcholine, 1-stearoyl-2-palmitoyl phosphatidylcholine, dimyristyl phosphatidylcholine, 1,2-distearoyl-sn-glycero-3-phosphocholine, 1,2-diarachidoyl-sn-glycero-3-phosphocholine, 1,2-dieicosenoyl-sn-glycero-3-phosphocholine, palmitoyloeoyl phosphatidylcholine, dimyristoyl phosphatidylethanolamine, palmitoyloeoyl phosphatidylethanolamine, cholesterol, 14Z,17Z,20Z,23Z,26Z,29Z-dotriacontahexaenoic acid, N-oleoylglycine, N-arachidonoylglycine, N-palmitoylglycine, 2-hydroxyoleic acid (sodium salt), 5-(palmitoyloxy)octadecanoic acid, 9-(palmitoyloxy)octadecanoic acid, 9-[((13,13,14,14,15,15,16,16,16-d9)palmitoyl)hydroxy]-stearic acid, 5-[((13,13,14,14,15,15,16,16,16-d9)palmitoyl)hydroxy]-stearic acid, Polyprenal, Dolichol, Coenzyme Q8 (E. coli), Coenzyme Q6, Prostaglandin B1, Prostaglandin A1, Prostaglandin F1β, Prostaglandin F1α, Prostaglandin E1, 1,2-diacyl-3-O-(α-D-glucopyranosyl)-sn-glycerol (E. coli), Monogalactosyldiacylglycerol (Plant), Digalactosyldiacylglycerol (Plant), sulfoquinovosyldiacylglycerol, 1-O-hexadecyl-sn-glycerol (HG), 1-O-hexadecyl-2-O-methyl-sn-glycerol (PMG), 1-O-hexadecyl-2-acetyl-sn-glycerol (HAG), Monogalactosyldiacylglycerol (Plant), Digalactosyldiacylglycerol (Plant), sulfoquinovosyldiacylglycerol, 1,2-dipalmitoyl-sn-glycero-3-O-4'-(N,N,N-trimethyl)-homoserine, 1,2-dipalmitoyl-sn-glycero-3-O-4'-[N,N,N-trimethyl(d9)]-homoserine, campest-5-en-3β-ol, campesterol-d6, β-sitostanol, 22,23-dihydrostigmasterol, (24-ethyl)-heptadeuteriostigmast-5-en-3β-ol, stigmasta-5,22-dien-3-ol, 1,2-dipalmitoyl ethylene glycol, 1-2-dioleoyl ethylene glycol, 1-O-hexadecyl-sn-glycerol (HG), 1,2-dioctanoyl-sn-glycerol, 1,2-didecanoyl-sn-glycerol, 1,2-dilauroyl-sn-glycerol, 1,2-dimyristoyl-sn-glycerol, 1,2-dipalmitoyl-sn-glycerol, 1,2-di-O-phytanyl-sn-glycerol, 1-2-dioleoyl-sn-glycerol, 1-palmitoyl-2-oleoyl-sn-glycerol, and 1-stearoyl-2-linoleoyl-sn-glycerol. In some embodiments, the neutral lipid is 1,2-dioleoyl-sn-glycero-3-phosphocholine (DOPC).

In some embodiments, the lipid bilayer comprises an anionic lipid. An "anionic lipid" is a lipid molecule (e.g., a phospholid molecule) with an overall negative charge. In some embodiments, an anionic lipid is a phospholipid with a negatively charged headgroup. Anionic lipids that may be used in accordance with the present disclosure include, without limitation: L-α-phosphatidylglycerol, L-α-phosphatidylserine, L-α-lysophosphatidylserine, L-alpha-lysophosphatidylinositol, L-α-phosphatidylinositol, cyclic phosphatidic acid, and phosphatidic acid.

In some embodiments, the lipid bilayer comprises a cationic lipid. A "cationic lipid" is a lipid molecule (e.g., a phospholid molecule) with an overall positive charge. In some embodiments, the cationic lipid is a phospholipid has a positively charged headgroup. In some embodiments, the cationic lipid may be N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP). 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl] cholesterol (DC-Choi); 2,3-dioleoyloxy-N-(2-(sperrninecarboxamido)-ethyl)-N,N-dimethyl-1-propanam-inium trifluoroacetate (DOSPA), .beta.-alanyl cholesterol, cetyl trimethyl ammonium bromide (CTAB), diC. sub.14-amidine, N-ferf-butyl-N'-tetradecy 1-3-tetradecylamino-propionami dine, N-(alpha-trimethylammonioacetyl)didodecyl-D-glutamate chloride (TMAG), ditetradecanoyl-N-(trimethylarnmonioacetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide. In some embodiments, the cationic lipids may be 1-[2-(acyloxy)ethyl]2-alkyl(alkenyl)-3-(2-hydroxyethyl)-imidazolinium chloride derivatives, for example, without limitation, 1-[2-(9(Z)-octadecenoyloxy) ethyl]-2-(8(Z)-heptadecenyl-3-(2-hydroxy ethyl)-imidazolinium chloride (DOTIM), and 1-[2-(hexadecanoyloxy) ethyl]-2-pentadecyl-3-(2-hydroxyethyl)imidazolinium chloride (DPTIM). In some embodiments, the cationic lipids may be 2,3-dialkyloxypropyl quaternary ammonium compound derivatives containing a hydroxyalkyl moiety on the quaternary amine, for example, without limitation, 1,2-dioleoyl-3-dimethyl-hydroxy ethyl ammonium bromide (DORI), 1,2-dioleyloxypropyl-3-dimethyl-hydroxy ethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxy propyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxy ethyl ammonium bromide (DSRIE). In some embodiments, the cationic lipid may be, without limitation: N1-[2-((1S)-1-[(3-aminopropyl)amino]-4-[di(3-amino-propyl)amino]butylcarboxamido)

ethyl]-3,4-di[oleyloxy]-benzamide, 1,2-di-O-octadecenyl-3-trimethylammonium propane (chloride salt), 1,2-dimyristoleoyl-sn-glycero-3-ethylphosphocholine (Tf salt), 1-palmitoyl-2-oleoyl-sn-glycero-3-ethylphosphocholine (chloride salt), 1,2-dioleoyl-sn-glycero-3-ethylphosphocholine (chloride salt), 1,2-distearoyl-sn-glycero-3-ethylphosphocholine (chloride salt), 1,2-dipalmitoyl-sn-glycero-3-ethylphosphocholine (chloride salt), 1,2-dimyristoyl-sn-glycero-3-ethylphosphocholine (chloride salt), 1,2-dilauroyl-sn-glycero-3-ethylphosphocholine (chloride salt), Dimethyldioctadecylammonium (Bromide Salt), 3β-[N—(N',N'-dimethylaminoethane)-carbamoyl]cholesterol hydrochloride, 1,2-dioleoyl-3-dimethylammonium-propane (DODAP), 1,2-dimyristoyl-3-dimethylammonium-propane, 1,2-dipalmitoyl-3-dimethylammonium-propane, 1,2-distearoyl-3-dimethylammonium-propane, N-(4-carboxybenzyl)-N,N-dimethyl-2,3-bis(oleoyloxy)propan-1-aminium, 1,2-dioleoyl-3-trimethylammonium-propane (methyl sulfate salt), 1,2-dioleoyl-3-trimethylammonium-propane (chloride salt), 1,2-stearoyl-3-trimethylammonium-propane (chloride salt), 1,2-dipalmitoyl-3-trimethylammonium-propane (chloride salt), 1,2-dimyristoyl-3-trimethylammonium-propane (chloride salt), or 1-oleoyl-2-[6-[(7-nitro-2-1,3-benzoxadiazol-4-yl)amino]hexanoyl]-3-trimethylammonium propane (chloride salt).

In some embodiments, the liposome of the present disclosure has an overall neutral charge (a "neutral liposome"). A liposome that has an overall neutral charge may contain neutral lipids, anionic lipids, and/or cationic lipids, so long as the overall charge remains neutral. In some embodiments, a neutral liposome comprises at least 50% neutral lipids (e.g., by molar ratio). In some embodiments, a neutral liposome does not comprise cationic lipids and/or anionic lipids. In some embodiments, a neutral liposome comprises at least 50%, at least 60%, at least 70%, at least 80%, at least 90%, at least 95%, at least 99% or more neutral lipids (e.g., by molar ratio). In some embodiments, a neutral liposome comprises 50%, 60%, 70%, 80%, 90%, 95%, 99% or more neutral lipids (e.g., by molar ratio).

In some embodiments, the liposome of the present disclosure has an overall positive charge (a "cationic liposome"). A cationic liposome and its use for delivering agents into a cell is known in the art. Cationic liposome-based transfection reagents are commercially available (e.g., Lipofectamine® products). In some embodiments, a cationic liposome comprises at least 30% cationic lipids (e.g., by molar ratio). In some embodiments, a cationic liposome comprises at least 30%, at least 40%, at least 50%, at least 60%, at least 70%, at least 80%, at least 90%, at least 95%, at least 99% or more cationic lipids (e.g., by molar ratio). In some embodiments, a cationic liposome comprises 30%, 40%, 50%, 60%, 70%, 80%, 90%, 95%, 99% or more cationic lipids (e.g., by molar ratio). In some embodiments, a cationic liposome comprises neutral lipids. Neutral lipids in a cationic liposome are also referred to as "helper lipids." In some embodiments, 5%-70% of the lipids (by molar ratio) in a cationic liposome are neutral lipids (helper lipids). For example, 5%, 10%, 15%, 20%, 25%, 30%, 35%, 40%, 45%, 50%, 55%, 60%, 65%, or 70% of the lipids (e.g., by molar ratio) in a cationic liposome may be neutral lipids (helper lipids).

In some embodiments, the liposomes of the present disclosure (e.g., the neutral or cationic liposomes) further comprises a pH-responsive lipid. A "pH-responsive lipid" refers to a lipid (e.g., a phospholipid) that contains a moiety that is responsive to pH such that the lipid is neutral at physiological pH (e.g., at a pH of about 7.4) but becomes positively charged when it is in an environment with a pH lower than physiological pH (e.g., at a pH of between 1-7). For example, a lipid having an imidazole moiety, which has a pK of about 6.0, will become predominantly positively charged at pH values less than 6.0. Therefore, in an endosome where the pH is between about 5.0 to about 6.0, the lipid protonates, facilitating uptake and release of the encapsulated cargo into the cytoplasm of the cell (e.g., as described in Xu et al., Biochemistry, 35:5616-5623 (1996)).

Non-limiting, exemplary pH-responsive lipids (e.g., phospholipids) that may be used in accordance with the present disclosure include N-palmitoyl homocysteine, 1,2-dioleoyl-sn-glycero-3-succinate, N-(4-carboxybenzyl)-N,N-dimethyl-2,3-bis(oleoyloxy)propan-1-aminium, 1,2-dioleoyl-3-dimethylammonium-propane (DODAP), 1,2-dimyristoyl-3-dimethylammonium-propane, 1,2-dipalmitoyl-3-dimethylammonium-propane, 1,2-distearoyl-3-dimethylammonium-propane, and N-(4-carboxybenzyl)-N,N-dimethyl-2,3-bis(oleoyloxy)propan-1-aminium. In some embodiments, the liposomes described herein comprises a pH-responsive lipid DODAP.

Liposomes containing pH-responsive lipids (e.g., pH-responsive phospholipids) may be referred to as pH-responsive liposomes. PH-responsive liposomes, when administered to a subject, such as a mammal, for example, a human, are uncharged, which allows for a longer blood circulation time than achieved with charged liposomes. Liposomes that are endocytosed or that reach a specific in vivo region where the pH is lower, become charged as the lipid becomes positively charged. This is due to the liposomes having a pH responsive moiety. This can occur, for example, in a tumor region or in a lysosome.

In some embodiments, the liposomes of the present disclosure further comprises a functionalized lipid. A "functionalized lipid" is a lipid (e.g., a phospholipid) that contains a reactive (i.e., functionalized) group (e.g., chemical group) that may be used to attach (e.g., covalently or non-covalently) a molecule (e.g., a chemical compound or a biological molecular such as a nucleic acid or a polypeptide) to the lipid. Functionalized lipids and methods of producing them are known in the art, e.g., as described in U.S. Pat. No. 5,556,948, incorporated herein by reference. In some embodiments, the functionalized lipid is a lipid-polymer conjugate.

A "lipid-polymer conjugate" refers to a lipid linked to a polymer covalently or non-covalently. A "polymer" is a substance that has a molecular structure consisting mainly or entirely of a large number of similar units bonded together, e.g., many synthetic organic materials used as plastics and resins. The polymer may be homopolymers or copolymers. Homopolymers are polymers which have one monomer in their composition. Copolymers are polymers which have more than one type of monomer in their composition. Copolymers may be block copolymers or random copolymers. Block copolymers contain alternating blocks (segments) of different homopolymers. Random copolymers contain random sequences of two or more monomers. A polymer is "soluble" in water if the polymer (either a homopolymer or copolymer) is soluble to at least 5% by weight at room temperature at a polymer size between about 20-150 subunits. A polymer is "soluble" in a polar organic solvent, which may be chloroform, acetonitrile, dimethylformamide, and/or methylene chloride, if the polymer (either a homopolymer or copolymer) is soluble to at least 0.5% by weight at room temperature, at a polymer size between about 20-150 subunits. Types of polymers that may be used to form lipid-polymer conjugates are known in the art, e.g., as described in U.S. Pat. Nos. 5,395,619 and 5,013,556, incorporated herein by reference.

Non-limiting examples of water soluble polymers include polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl-pyrrolidone)polyethylene glycol, propropylene glycol homopolymers, polypropylene oxide/ethylene oxide copolymers, and polyoxyethylated polyols.

Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation to a polymer can improve serum half-life, among other effects. Methods of conjugation are well known in the art, for example, P. E. Thorpe, et al, 1978, Nature 271, 752-755; Harokopakis E., et al., 1995, Journal of Immunological Methods, 185:31-42; S. F. Atkinson, et al., 2001, J. Biol. Chem., 276:27930-27935; and U.S. Pat. Nos. 5,601,825, 5,180,816, 6,423,685, 6,706,252, 6,884,780, and 7,022,673, incorporated herein by reference.

In some embodiments, the lipid-polymer conjugate described herein comprises a lipid (e.g., phospholipid) linked to a polyethylene glyco (PEG). In some embodiments, the lipid is covalently attached to the polymer (e.g., PEG). The polymer may be of any molecular weight, and may be branched or unbranched. In some embodiments, the PEG used in accordance with the present disclosure is linear, unbranched PEG having a molecular weight of from about 1 kilodaltons (kDa) to about 60 kDa (the term "about" indicating that in preparations of PEG, some molecules will weigh more, and some less, than the stated molecular weight). For example, the PEG may have a molecular weight of 1-60, 1-50, 1-40, 1-30, 1-20, 1-10, 1-5, 5-60, 5-50, 5-40, 5-30, 5-20, 5-10, 10-60, 10-50, 10-40, 10-30, 10-20, 20-60, 20-50, 20-40, 20-30, 30-60, 30-50, 30-40, 40-60, 40-50, or 50-60 kDa. In some embodiments, the PEG has a molecular weight of 1, 2, 3, 4, 5, 10, 15, 20, 25, 30, 35, 40, 45, 50, 55, or 60 kDa.

In some embodiments, the functionalized lipid comprises reactive group or functional group at the distal end of the lipid. In some embodiments, the polymer (e.g., PEG) conjugated to the lipid contains a reactive group of function group at the distal end of the lipid. The "distal end" has the common meaning in the art and refers to the end that is away from the lipid bilayer. The reactive group or functional group is on the surface of the liposome, i.e., exposed and accessible to other molecules.

A "reactive group" or "functional group" refers to specific groups (moieties) of atoms or bonds within molecules that are responsible for the characteristic chemical reactions of those molecules. These terms are used interchangeably herein. One example of such reactive group is a "click chemistry handle." Click chemistry is a chemical approach introduced by Sharpless in 2001 and describes chemistry tailored to generate substances quickly and reliably by joining small units together. See, e.g., Kolb, Finn and Sharpless Angewandte Chemie International Edition (2001) 40: 2004-2021; Evans, Australian Journal of Chemistry (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition). Non-limiting examples of a click chemistry handle include an azide handle, an alkyne handle, or an aziridine handle. Azide is the anion with the formula N3−. It is the conjugate base of hydrazoic acid (HN3). N3− is a linear anion that is isoelectronic with $CO_2$, NCO−, $N_2O$, $NO_2+$ and NCF. Azide can be described by several resonance structures, an important one being —N=N+=N—. An alkyne is an unsaturated hydrocarbon containing at least one carbon-carbon triple bond. The simplest acyclic alkynes with only one triple bond and no other functional groups form a homologous series with the general chemical formula $C_nH_{2n-2}$. Alkynes are traditionally known as acetylenes, although the name acetylene also refers specifically to $C_2H_2$, known formally as ethyne using IUPAC nomenclature. Like other hydrocarbons, alkynes are generally hydrophobic but tend to be more reactive. Aziridines are organic compounds containing the aziridine functional group, a three-membered heterocycle with one amine group (—NH—) and two methylene bridges (—$CH_2$-). The parent compound is aziridine (or ethylene imine), with molecular formula $C_2H_5N$.

Other non-limiting, exemplary reactive groups include: acetals, ketals, hemiacetals, and hemiketals, carboxylic acids, strong non-oxidizing acids, strong oxidizing acids, weak acids, acrylates and acrylic acids, acyl halides, sulfonyl halides, chloroformates, alcohols and polyols, aldehydes, alkynes with or without acetylenic hydrogen amides and imides, amines, aromatic, amines, phosphines, pyridines, anhydrides, aryl halides, azo, diazo, azido, hydrazine, and azide compounds, strong bases, weak bases, carbamates, carbonate salts, chlorosilanes, conjugated dienes, cyanides, inorganic, diazonium salts, epoxides, esters, sulfate esters, phosphate esters, thiophosphate esters borate esters, ethers, soluble fluoride salts, fluorinated organic compounds, halogenated organic compounds, halogenating agents, aliphatic saturated hydrocarbons, aliphatic unsaturated hydrocarbons, hydrocarbons, aromatic, insufficient information for classification, isocyanates and isothiocyanates, ketones, metal hydrides, metal alkyls, metal aryls, and silanes, alkali metals, nitrate and nitrite compounds, inorganic, nitrides, phosphides, carbides, and silicides, nitriles, nitro, nitroso, nitrate, nitrite compounds, organic, non-redox-active inorganic compounds, organometallics, oximes, peroxides, organic, phenolic salts, phenols and cresols, polymerizable compounds, quaternary ammonium and phosphonium salts, strong reducing agents, weak reducing agents, acidic salts, basic salts, siloxanes, inorganic sulfides, organic sulfides, sulfite and thiosulfate salts, sulfonates, phosphonates, organic thiophosphonates, thiocarbamate esters and salts, and dithiocarbamate esters and salts. In some embodiments, the reactive group is a carboxylic acid group.

Non-limiting, exemplary functionalized lipids (e.g., phospholipids) include: 1,2-distearoyl-sn-glycero-3-phosphoethanolamine-N-[amino(polyethylene glycol)], D-lactosyl-β-1,1' N-(6"-azidohexanoyl)-D-erythro-sphingosine, N-(6-azidohexanoyl)-D-erythro-sphingosine, D-galactosyl-β-1,1' N-(6"-azidohexanoyl)-D-erythro-sphingosine, D-gluctosyl- β-1,1' N-(6"-azidohexanoyl)-D-erythro-sphingosine, (2S,3R,E)-2-amino-13-(3-(pent-4-yn-1-yl)-3H-diazirin-3-yl)dodec-4-ene-1,3-diol, Hex-5'-ynyl 3β-hydroxy-6-diazirinyl-5α-cholan-24-oate, 27-norcholest-5-en-25-yn-3β-ol, 27-alkyne cholesterol, 5Z,8Z,11Z,14Z-eicosatetraen-19-ynoic acid, 1,2-distearoyl-sn-glycero-3-phosphoethanolamine-N-[dibenzocyclooctyl(polyethylene glycol)], 1,2-dipalmitoyl-sn-glycero-phosphoethanolamine-N-(5-hexynoyl), 1,2-dipalmitoyl-sn-glycero-3-phosphoethanolamine-N-(6-azidohexanoyl), 1,2-dipalmitoyl-sn-glycero-3-phosphoethanolamine-N-dibenzocyclooctyl, 1,2-dioleoyl-sn-glycero-3-phosphoethanolamine-N-dibenzocyclooctyl, 15-hexadecynoic acid, (Z)-octadec-9-en-17-ynoic acid, 9-(3-pent-4-ynyl-3-H-diazirin-3-yl)-nonanoic acid, N-(9-(3-pent-4-ynyl-3-H-diazirin-3-yl)-nonanoyl)-D-erythro-sphingosine, D-galactosyl-β-1,1' N-(9-(3-pent-4-ynyl-3-H-diazirin-3-yl)-nonanoyl)-D-erythro-sphingosine, D-glucosyl-β-1,1' N-(9-(3-pent-4-ynyl-3-H-diazirin-3-yl)-nonanoyl)-D-erythro-sphingosine, 1-palmitoyl-2-(9-(3-pent-4-ynyl-3-H-diazirin-3-yl)-nonanoyl)-sn-glycero-3-phosphocholine, 1-(9-(3-pent-4-ynyl-3-H-diazirin-3-yl)-nonanoyl)-2-oleoyl-sn-glycero-3-phosphocholine, 1,2-dioleyl-sn-glycero-3-phosphoethanolamine-N-(dabsyl), 1,2-dipalmitoyl-sn-glycero-3-phospho((ethyl-1',2',3'-triazole) triethyleneglycolmannose), 1,2-Dipalmitoyl-sn-Glycero-3-Phosphoethanolamine-N-(hexanoylamine), 1,2-dioleoyl-sn-glycero-3-phosphoethanolamine-N-(hexanoylamine), 1,2-dipalmitoyl-sn-glycero-3-phosphoethanolamine-N-[4-(p-maleimidophenyl)butyramide], 1,2-dioleoyl-sn-glycero-3-phosphoethanolamine-N-[4-(p-maleimidophenyl)butyramide], 1,2-dipalmitoyl-sn-glycero-3-phospho(ethylene glycol), 1,2-Dioleoyl-sn-Glycero-3-Phospho(Ethylene Glycol), 1,2-dipalmitoyl-sn-glycero-3-phosphoethanolamine-N-(6-((folate)amino)hexanoyl), 1,2-dipalmitoyl-sn-glycero-3-phosphoethanolamine-N-(cyanur), 1,2-dipalmitoyl-sn-glycero-3-phosphoethanolamine-N-(biotinyl), 1,2-dioleoyl-sn-glycero-3-phosphoethanolamine-N-(biotinyl), 1,2-dipalmitoyl-sn-glycero-3-phosphoethanolamine-N-(cap biotinyl), 1,2-dipalmitoyl-sn-glycero-3-phosphoethanolamine-N-{6-[(cyanur)amino]hexanoyl}, 1,2-dioleoyl-sn-glycero-3-phosphoethanolamine-N-(cap biotinyl), 1,2-dipalmitoyl-sn-glycero-3-phosphoethanolamine-N-(dodecanoyl), 1,2-dioleoyl-sn-glycero-3-phosphoethanolamine-N-(dodecanyl), 1,2-dipalmitoyl-sn-glycero-3-phosphoethanolamine-N-(glutaryl), 1,2-dioleoyl-sn-glycero-3-phosphoethanolamine-N-(glutaryl), 1,2-dipalmitoyl-sn-glycero-3-phosphoethanolamine-N-(succinyl), 1,2-dioleoyl-sn-glycero-3-phosphoethanolamine-N-(succinyl), 1,2-dipalmitoyl-sn-glycero-3-phosphoethanolamine-N-[3-(2-pyridyldithio)propionate], 1,2-dioleoyl-sn-glycero-3-phosphoethanolamine-N-[3-(2-pyridyldithio)propionate], 1,2-Dipalmitoyl-sn-Glycero-3-Phosphothioethanol, 1,2-dioleoyl-sn-glycero-3-phosphoethanolamine-N-(dodecanylamine), 1,2-dipalmitoyl-sn-glycero-3-phosphoethanolamine-N-(dodecanylamine), 1,2-dipalmitoyl-sn-glycero-3-phosphoethanolamine-N-[4-(p-maleimidomethyl)cyclohexane-carboxamide], 1,2-dioleoyl-sn-glycero-3-phosphoethanolamine-N-[4-(p-maleimidomethyl)cyclohexane-carboxamide], 1,2-dipalmitoyl-sn-glycero-3-phosphoethanolamine-N-(5-hexynoyl), 1,2-dipalmitoyl-sn-glycero-3-phosphoethanolamine-N-(6-azidohexanoyl), 1,2-distearoyl-sn-glycero-3-phosphoethanolamine-N-(maleimide), 1,2-distearoyl-sn-glycero-3-phosphoethanolamine-n-(dibenzocycooctyl), 1,2-distearoyl-sn-glycero-3-phosphoethanolamine-N-[10-(trimethoxysilyl)undecanamide], 1,2-distearoyl-sn-glycero-3-phosphoethanolamine-N—(PDP), 1,2-distearoyl-sn-glycero-3-phosphoethanolamine-N-(carboxy), 1,2-distearoyl-sn-glycero-3-phosphoethanolamine-N-(folate), and N-(4-carboxybenzyl)-N,N-dimethyl-2,3-bis(oleoyloxy)propan-1-aminium. In some embodiments, the functionalized lipid is 1,2-distearoyl-sn-glycero-3-phosphoethanolamine-N-[carboxy(polyethylene glycol)-2000]-COOH (DSPE-PEG-COOH).

In some embodiments, the lipid bilayer of the liposome comprises neutral lipid (e.g., DOPC), a pH-responsive lipid (e.g., DODAP), and a functionalized lipid (DSPE-PEG-COOH). In some embodiments, the neutral lipid is 50%-99% (by molar ratio) of the total lipid composition of the lipid bilayer. For example, the neutral lipid may be 50%-99%, 50%-95%, 50%-90%, 50%-85%, 50%-80%, 50%-75%, 50%-70%, 50%-65%, 50%-60%, 50%-55%, 55%-99%, 55%-95%, 55%-90%, 55%-85%, 55%-80%, 55%-75%, 55%-70%, 55%-65%, 55%-60%, 60%-99%, 60%-95%, 60%-90%, 60%-85%, 60%-80%, 60%-75%, 60%-70%, 60%-65%, 65%-99%, 65%-95%, 65%-90%, 65%-85%, 65%-80%, 65%-75%, 65%-70%, 70%-99%, 70%-95%, 70%-90%, 70%-85%, 70%-80%, 70%-75%, 75%-99%, 75%-95%, 75%-90%, 75%-85%, 75%-80%, 80%-99%, 80%-95%, 80%-90%, 80%-88%, 85%-99%, 85%-95%, 85%-90%, 90%-99%, 90%-95%, or 95%-99% (by molar ratio) of the total lipid composition of the lipid bilayer. In some embodiments, the neutral lipid is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (by molar ratio) of the total lipid composition of the lipid bilayer.

In some embodiments, the pH-responsive lipid is 1%-40% (by molar ratio) of the total lipid composition of the lipid bilayer. For example, the pH-responsive lipid may be 1%-40%, 1%-35%, 1%-30%, 1%-25%, 1%-20%, 1%-15%, 1%-10%, 1%-5%, 5%-40%, 5%-35%, 5%-30%, 5%-25%, 5%-20%, 5%-15%, 5%-10%, 10%-40%, 10%-35%, 10%-30%, 10%-25%, 10%-20%, 10%-15%, 15%-40%, 15%-35%, 15%-30%, 15%-25%, 15%-20%, 20%-40%, 20%-35%, 20%-30%, 20%-25%, 25%-40%, 25%-35%, 25%-30%, 30%-40%, 30%-35%, or 35%-40% (by molar ratio) of the total lipid composition of the lipid bilayer. In some embodiments, the pH-responsive lipid is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% (by molar ratio) of the total lipid composition of the lipid bilayer. In some embodiments, the lipid bilayer of the liposome does not contain a pH-responsive lipid (i.e., 0% by molar ratio).

In some embodiments, the functionalized lipid is 1%-20% (by molar ratio) of the total lipid composition of the lipid bilayer. For example, the functionalized lipid may be 1%-20%, 1%-15%, 1%-10%, 1%-5%, 5%-20%, 5%-15%, 5%-10%, 10%-20%, 10%-15%, or 15%-20% (by molar ratio) of the total lipid composition of the lipid bilayer. In some embodiments, the functionalized lipid is 1%, 2%, 3%, 4%, 5%, 6%, 7%, 8%, 9%, 10%, 11%, 12%, 13%, 14%, 15%, 16%, 17%, 18%, 19%, or 20% (by molar ratio) of the total lipid composition of the lipid bilayer. In some embodiments, higher (e.g., more than 20%) or lower (e.g., less than 1%) percentages of functionalized lipid in the lipid bilayer is also contemplated. The percentage of the functionalized lipid is at least in part related to the amount of ligands needed to be conjugated to the liposome containing the functionalized lipids.

In some embodiments, the molar ratio of the neutral lipid, the pH-responsive lipid, and the functionalized lipid in the lipid bilayer of the liposomes described herein is 65%:30%:5%. In some embodiments, the molar ratio of the neutral lipid, the pH-responsive lipid, and the functionalized lipid in the lipid bilayer of the liposomes described herein is 85%:10%:5%. In some embodiments, the lipid bilayer of the liposomes described herein does not contain a pH-responsive lipid and the molar ratio of the neutral lipid and the functionalized lipid is 95%:5%.

A liposome containing functionalized lipids may be referred to as a functionalized liposome. The functional groups of the functional lipids are arranged on the outer surface of the liposome, allowing attaching or conjugation of a wide range of molecules (e.g., nucleic acids, polypeptides or proteins, organic compounds, etc.) to the surface of the functionalized liposomes. In some embodiments, the molecule is a ligand.

A "ligand," as used herein, refers to a molecule that specifically binds to and forms a complex with another molecule (e.g., a biomolecule such as a protein). The molecule that is bound by the ligand is herein referred as a "target molecule." In some embodiments, the target molecule is a protein, e.g., a receptor protein. In some embodiments, the target molecular is a cell surface receptor protein. The binding of a ligand to its target molecule may be via intermolecular forces, such as ionic bonds, hydrogen bonds and Van der Waals forces. In some embodiments, the binding of a ligand to its target molecule (e.g., a receptor protein) serves a biological purpose. For example, binding of a ligand to a receptor protein alters the chemical conformation by affecting the three-dimensional shape orientation. The conformation of a receptor protein composes its functional state. Ligands include substrates, inhibitors, activators, antibodies, and neurotransmitters. The rate of binding is called affinity ($K_D$), and this measurement typifies a tendency or strength of the effect of binding. Binding affinity is actualized not only by host-guest interactions, but also by solvent effects that can play a dominant, steric role which drives non-covalent binding in solution. The solvent provides a chemical environment for the ligand and receptor to adapt, and thus accept or reject each other as partners.

The term "bind" refers to the association of two entities (e.g., two proteins). Two entities (e.g., two proteins) are considered to bind to each other when the affinity ($K_D$) between them is $<10^{-3}$ M, $<10^{-4}$ M, $<10^{-5}$ M, $<10^{-6}$ M, $<10^{-7}$ M, $<10^{-8}$ M, $<10^{-9}$ M, $<10^{-10}$ M, $<10^{-11}$ M, or $<10^{-12}$ M. One skilled in the art is familiar with how to assess the affinity of two entities (e.g., two proteins).

Any ligands (e.g., a protein ligand) may be conjugated to the surface of the liposomes described herein. The terms conjugating, conjugated, and conjugation refer to an association of two entities, for example, of two molecules (e.g., two proteins), two domains, or a protein and an agent, e.g., a protein and a lipid. The association can be, for example, via a direct or indirect (e.g., via a linker) covalent linkage or via non-covalent interactions. In some embodiments, the association is covalent. For example, in some embodiments, the a protein and a lipid is conjugated via the reactive group on a functionalized lipid, the association between the protein and the lipid is covalent. In some embodiments, two molecules are conjugated via a linker connecting both molecules.

In some embodiments, a ligand (e.g., a protein ligand) may be conjugated to the surface of the liposome via the functional group on the functionalized lipid in the liposome. For example, without limitation, a functionalized lipid containing carboxylic acid group may react with the amine group at the N-terminus of a protein or polypeptide ligand, thereby conjugating the protein or polypeptide ligand to the surface of the liposome. Methods of conjugating a ligand via a reactive or functional group is known to those skilled in the art.

In some embodiments, a liposome may be engineered such that it specifically targets one cell type (e.g., a cancer cell) but not other cell types (e.g., a normal cell). As such, the ligands conjugated to the surface of the liposome are ligands that binds to cell surface proteins that specifically express or overexpress on one cell type cell type (e.g., a cancer cell) but not other cell types (e.g., a normal cell). Surface proteins that specifically express or overexpress on one cell type but not other cell types may be identified by any known methods in the art, e.g., western blotting, immunostaining, flow-cytometry or mass-spectrometry. Exemplified herein are methods of quantifying and/or profiling the expression level of surface proteins on triple-negative breast cancer cells (TNBC) using flow cytometry, for the identification of proteins that specifically express or overexpress on TNBC cells, compared to normal cells. The examples provided herein are not meant to be limiting. Cell-surface protein expression profiles on any cell types may be analyzed using the methods described herein.

A protein (e.g., membrane protein) that specifically expresses on the surface of one cell type but not another refers to a protein that is only detectable on one cell type using any protein detection methods known in the art (e.g., western blotting, immunostaining, flow-cytometry or mass-spectrometry), but is not detectable on any other cell types. A protein that overexpresses on the surface of one cell type compared to another refers to a protein whose surface expression level is higher than that of another cell type. For example, the expression level of an overexpressed protein on the surface of one cell type may be at least 20% higher than its expression level on the surface of another cell type. In some embodiments, the expression level of an overexpressed protein on the surface of one cell type is at least 20%, at least 30%, at least 40%, at least 50%, at least 60%, at least 70%, at least 80%, at least 90%, at least 100%, at least 2-fold, at least 3-fold, at least 4-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, or at least 1000-fold higher than its expression level on the surface of another cell type. In some embodiments, the expression level of an overexpressed protein on the surface of one cell type is 20%, 30%, 40%, 50%, 60%, 70%, 80%, 90%, 100%, 2-fold, 3-fold, 4-fold, 5-fold, 10-fold, 20-fold, 30-fold, 40-fold, 50-fold, 60-fold, 70-fold, 80-fold, 90-fold, 100-fold, or 1000-fold higher than its expression level on the surface of another cell type. In some embodiments, the expression level of an overexpressed protein on the surface of one cell type is more than 1000-fold higher than its expression level on the surface of another cell type. In some embodiments, a protein that overexpresses on the surface of a cell may also be overexpressed in the cell. In some embodiments, a protein that overexpresses on the surface of a cell is not overexpressed in the cell.

Some aspects of the present disclosure provide liposomes with one or more (e.g., 2, 3, 4, 5, 6, 7, 8, 9, 10, or more) ligands conjugated to the liposome surface, wherein the molecular ratio of the ligands complements the ratio of the overexpressed cell surface proteins targeted by the ligands. Quantifying the surface expression level of cell surface proteins (e.g., by the methods described herein) allows calculation of a ratio (also referred to herein as "relative molecular density") of multiple cell surface proteins. A "ratio" or "relative molecular density" of two cell surface proteins is calculated as the surface expression level of one cell surface protein/the surface expression level of the other cell surface protein, and is expressed as X:1, wherein X is the surface expression level of one cell surface protein/the surface expression level of the other cell surface protein. The molecular ratio of the ligands is considered to "complement" the relative molecular density (i.e., ratio) of the cell surface proteins when the molecular ratio of the ligands is within 30% (including 30%) more or less than the relative molecular density (i.e., ratio) of the cell surface proteins. For example, if the relative molecular density (i.e., ratio) of two cell surface proteins is 2:1, the ligands conjugated to the liposome surface is considered to complement the relative molecular density (i.e., ratio) when the molecular ratio of the two ligands is between 1.4:1-2.6:1. In some embodiments, the molecular ratio of the ligands is within 30%, within 25%, within 20%, within 15%, within 10%, within 10%, within 5%, within 1% (inclusive) more or less than the relative molecular density (i.e., ratio) of the cell surface proteins. In some embodiments, the molecular ratio of the ligands is 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% 5%, 4%, 3%, 2%, or 1% more or less than the relative molecular density (i.e., ratio) of the cell surface proteins. In some embodiments, the molecular ratio of the ligands the same as the relative molecular density (i.e., ratio) of the cell surface proteins.

When the molecular ratio of the ligands conjugated to a liposome surface complement the relative molecular density (i.e., ratio) of the cell surface proteins on a cell, the liposome targets the cell with higher specificity and affinity. Such liposomes are referred to herein as "complementary liposomes." In some embodiments, the complementary liposome targets a cell that it is "complementary to" with a specificity that is at least 20% (e.g., at least 20%, at least 30%, at least 40%, at least 50%, at least 60%, at least 70%, at least 80%, at least 90%, at least 100%, at least 2-fold, at least 3-fold, at least 4-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 1000-fold higher than a "non-complementary liposome." In some embodiments, the complementary liposome targets a cell that it is "complementary to" with an affinity that is at least 20% (e.g., at least 20%, at least 30%, at least 40%, at least 50%, at least 60%, at least 70%, at least 80%, at least 90%, at least 100%, at least 2-fold, at least 3-fold, at least 4-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 1000-fold higher than a "non-complementary liposome."

In some embodiments, the overexpressed surface protein of the present disclosure is a protein that specifically expresses or overexpresses on the surface of cancer or tumor cells (e.g., TNBC cells). Such proteins are referred to herein as "cancer-specific cell surface proteins." Proteins that are overexpressed on the surface of cancer or tumor cells are known in the art or may be identified using the methods described herein.

Accordingly, some aspects of the present disclosure provide cancer-targeting liposomes comprising one or more ligands (e.g., 1, 2, 3, 4, 5 or more) conjugated to its surface. The ligands of the cancer-targeting liposome specifically binds or targets. The cancer-targeting liposome comprises a lipid bilayer comprising the lipids (e.g., phospholipids) described herein. In some embodiments, the cancer-targeting liposome comprises one or more ligands that binds to proteins that overexpress on cancer surface. Suitable cancers/tumors that may be targeted by the liposomes described herein include, without limitation, neoplasms, malignant tumors, metastases, or any disease or disorder characterized by uncontrolled cell growth such that it would be considered cancerous. The cancer may be a primary or metastatic cancer. Cancers include, but are not limited to, adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, biliary tract cancer, osteosarcoma, fibrous histiocytoma, brain cancer, brain stem glioma, cerebellar astrocytoma, malignant glioma, glioblastoma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, acute lymphocytic and myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, choriocarcinoma, hematological neoplasm, adult T-cell leukemia, lymphoma, lymphocytic lymphoma, stromal tumors and germ cell tumors, or Wilms tumor. In some embodiments, the cancer is lung cancer, breast cancer, prostate cancer, colorectal cancer, gastric cancer, liver cancer, pancreatic cancer, brain and central nervous system cancer, skin cancer, ovarian cancer, leukemia, endometrial cancer, bone, cartilage and soft tissue sarcoma, lymphoma, neuroblastoma, nephroblastoma, retinoblastoma, or gonadal germ cell tumor. In some embodiments, the cancer is melanoma or ovarian cancer. In some embodiments, the cancer is breast cancer. In some embodiments, the cancer is triple-negative breast cancer (TNBC).

In some embodiments, the ligand conjugated to the surface of the cancer-targeting liposome targets a protein that overexpresses on the surface of TNBC. As such, the cancer-targeting liposome targets TNBC. In some embodiments, the ligands target the epidermal growth factor receptor (EGFR). Such ligands are referred to herein as "EGFR ligands." EGFR is the cell-surface receptor for members of the epidermal growth factor family (EGF family) of extracellular protein ligands. Mutations that lead to EGFR overexpression (also known as upregulation) or overactivity have been associated with a number of cancers, including squamous-cell carcinoma of the lung (about 80% of cases), anal cancers, glioblastoma (about 50%) and epithelial tumors of the head and neck (about 80-100%). These somatic mutations involving EGFR lead to its constant activation, which produces uncontrolled cell division.

The EGFR ligands described herein do not encompass natural EGFR ligands that activate EGFR signaling, e.g., TGF-α and EGF. In some embodiments, an EGFR ligand binds to EGFR on the surface of a cancer/tumor cell. The EGFR ligands of the present disclosure blocks/inhibits the interaction between EGFR and its activating ligands. In some embodiments, the binding of the EGFR ligand to EGFR blocks/inhibits EGFR signaling in the tumor cell, leading to inhibition of tumor growth.

In some embodiments, the ligands target the intercellular adhesion molecule 1 (ICAM-1). Such ligands are referred to herein as "ICAM-1 ligands." ICAM-1 is a member of the super-immunoglobulin family of molecules. Members of this superfamily are characterized by the presence of one or more Ig homology regions, each consisting of a disulfide-bridged loop that has a number of anti-parallel β-pleated strands arranged in two sheets. Three types of homology regions have been defined, each with a typical length and having a consensus sequence of amino acid residues located between the cysteines of the disulfide bond. (Williams, A. F. et al., Ann. Rev. Immunol. 6:381-405 (1988); Hunkapillar, T. et al., Adv. Immunol. 44:1-63 (1989)). ICAM-1 is a cell surface glycoprotein of 97-114 kd. ICAM-1 has 5 Ig-like domains. Its structure is closely related to those of the neural cell adhesion molecule (NCAM) and the myelin-associated glycoprotein (MAG) (e.g., as described Simmons, D. et al., Nature 331:624-627 (1988); Staunton, D. E. et al., Cell 52:925-933 (1988); Staunton, D. E. et al., Cell 61243-254 (1990), herein incorporated by reference). ICAM has previously been shown to overexpression on TNBC cells and has been characterized as a molecular target for TNBC (e.g., as described in Guo et al., PNAS, vol. 111, no. 41, pages 14710-14715, 2014; and Guo et al., Theranostics, Vol. 6, Issue 1, 2016, incorporated herein by reference).

The ICAM-1 ligands described herein bind to ICAM-1 on the surface of a cancer/tumor cell. In some embodiments, the ICAM-1 ligands of the present disclosure blocks/inhibits ICAM-1 signaling in the tumor cell, leading to inhibition of tumor growth.

Suitable EGFR ligands or ICAM-1 ligands that may be conjugated to the cancer-targeting liposomes include, without limitation: antibodies or antibody fragments, inhibitory peptides including peptides derived from natural proteins and synthetic peptides, natural inhibitory ligands, small molecules (e.g., small molecule inhibitors), and aptamers.

"Antibodies" and "antibody fragments" include whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody may be a polyclonal antibody or a monoclonal antibody.

An "antibody fragment" for use in accordance with the present disclosure contains the antigen-binding portion of an antibody (e.g., an EGFR antibody). The antigen-binding portion of an antibody refers to one or more fragments of an antibody that retain the ability to specifically bind to an antigen (e.g., EGFR). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (e.g., as described in Ward et al., (1989) Nature 341:544-546, incorporated herein by reference), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883, incorporated herein by reference). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

EGFR antibodies that inhibit EGFR signaling are known in the art and have been used for treatment of cancer, e.g., without limitation, Erbitux (generic name: cetuximab), Vectibix (generic name: panitumumab), Portrazza (generic name: necitumumab). ICAM-1 antibodies are known to those skilled in the art and are commercially available (e.g., from Santa Cruz or Abcam).

"Inhibitory peptides" refers to peptides that specifically binds to EGFR or ICAM-1 and inhibits EGFR signaling or ICAM-1 signaling, respectively. For example, peptides that are derived from the EGFR-binding portion of proteins that binds to EGFR (e.g., epidermal growth factor or EGF) may be used as an inhibitory peptide in accordance with the present disclosure. An inhibitory peptides may also be synthetic (i.e., synthetic peptides). Similarly, peptides that are derived from the ICAM-1 binding portion of proteins that binds to ICAM-1 (e.g., integrin) may be used as an inhibitory peptide in accordance with the present disclosure. Synthetic peptides may be obtained using methods that are known to those skilled in the art. Synthetic peptides that inhibit EGFR signaling are known in the art, e.g., as described in Ahsan et al., Neoplasia, Volume 16, Issue 2, February 2014, Pages 105-114; and in Sinclair et al., Org Lett. 2014 Sep. 19; 16(18):4916-9, incorporated herein by reference. Synthetic peptides that inhibit ICAM-1 function are known in the art, e.g., as described in Zimmerman et al., Chem Biol Drug Des. 2007 October; 70(4):347-53. Epub 2007, incorporated herein by reference.

An "aptamer" refers to an oligonucleotide or a peptide molecule that binds to a specific target molecule. Aptamers are usually created by selecting them from a large random sequence pool. Aptamers that inhibit EGFR signaling are known to those skilled in the art, e.g., as described in Li et al., PloS ONE, Volume 6, Issue 6, e20299, 2011, Liu et al., Biol Chem. 2009 February; 390(2): 10.1515/BC.2009.022, and US Patent Application Publication US20130177556, incorporated herein by reference.

A "natural ligand" is a ligand that exists in nature. The present disclosure encompass natural ligands for proteins that specifically express or overexpress on the surface of a cell targeted by the nanoparticles described herein (e.g., a cancer cell). The natural ligands of the present disclosure inhibit the signaling of the overexpressed proteins (e.g., EGFR or ICAM-1) on the surface of a cell targeted by the liposomes (e.g., a cancer cell).

A "small molecule," as used herein, refers to a molecule of low molecular weight (e.g., <900 daltons) organic or inorganic compound that may function in regulating a biological process. Nonlimiting examples of a small molecule include lipids, monosaccharides, second messengers, other natural products and metabolites, as well as drugs and other xenobiotics.

A "lipid" refers to a group of naturally occurring molecules that include fats, waxes, sterols, fat-soluble vitamins (such as vitamins A, D, E, and K), monoglycerides, diglycerides, triglycerides, phospholipids, and others. A "monosaccharide" refers to a class of sugars (e.g., glucose) that cannot be hydrolyzed to give a simpler sugar. Non-limiting examples of monosaccharides include glucose (dextrose), fructose (levulose) and galactose. A "second messenger" is a molecule that relay signals received at receptors on the cell surface (e.g., from protein hormones, growth factors, etc.) to target molecules in the cytosol and/or nucleus. Nonlimiting examples of second messenger molecules include cyclic AMP, cyclic GMP, inositol trisphosphate, diacylglycerol, and calcium. A "metabolite" is an molecule that forms as an intermediate produce of metabolism. Non-limiting examples of a metabolite include ethanol, glutamic acid, aspartic acid, 5' guanylic acid, Isoascorbic acid, acetic acid, lactic acid, glycerol, and vitamin B2. A "xenobiotic" is a foreign chemical substance found within an organism that is not normally naturally produced by or expected to be present within. Non-limiting examples of xenobiotics include drugs, antibiotics, carcinogens, environmental pollutants, food additives, hydrocarbons, and pesticides.

Small molecule inhibitors of EGFR and ICAM-1 are also known to those skilled in the art. Non-limiting, exemplary small molecule inhibitors for EGFR include AEE 788, AG 1478 hydrochloride, AG 18, AG 490, AG 494, AG 555, AG 556, AG 825, AG 879, AG 99, AV 412 New product, BIBU 1361 hydrochloride, BIBX 1382 dihydrochloride, BMS 599626 dihydrochloride, Canertinib dihydrochloride, CGP 52411, CP 724714, DIM, Genistein, GW 583340 dihydrochloride, HDS 029, HKI 357, Iressa, JNJ 28871063 hydrochloride, Lavendustin A, Methyl 2,5-dihydroxycinnamate, PD 153035 hydrochloride, PD 158780, PF 6274484, PKI 166 hydrochloride, PP 3, TAK 165, Tyrphostin B44, (−) enantiomer, Tyrphostin B44, (+) enantiomer, and WHI-P 154. Non-limiting, exemplary small molecule inhibitors for EGFR include metadichol, methimazole, and silibinin.

Multiple ligands may be conjugated to the surface of the liposome, each ligand targeting a different cell surface protein. In some embodiments, 2-10 cell surface proteins are targeted by the ligands conjugated to the surface of the liposome. For example, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 cell surface proteins are targeted. In some embodiments, 1, 2, 3, 4, 5, 6, 7, 8, 9, or 10 cell surface proteins are targeted.

In some embodiments, the cancer-targeting liposome is a complementary liposome to a cancer cell (e.g., TNBC). That means, the molecular ratio of ligands conjugated on the liposome surface complements the overexpressed proteins on a cancer cell (e.g., EGFR and ICAM-1). Also provided herein are the relative densities of ICAM-1 and EGFR on the surface of TNBC cells. On a complementary cancer targeting liposome, the molecular ratio of ICAM-1 and EGFR may be 0.01-10. In some embodiments, the molecular ratio of ICAM-1 and EGFR is 0.01-10, 0.01-9, 0.01-8, 0.01-7, 0.01-6, 0.01-5, 0.01-4, 0.01-3, 0.01-2, 0.01-1, 0.01-0.5, 0.01-0.1, 0.01-0.05, 0.05-10, 0.05-9, 0.05-8, 0.05-7, 0.05-6, 0.05-5, 0.05-4, 0.05-3, 0.05-2, 0.05-1, 0.05-0.5, 0.05-0.1, 0.1-10, 0.1-9, 0.1-8, 0.1-7, 0.1-6, 0.1-5, 0.1-4, 0.1-3, 0.1-2, 0.1-1, 0.1-0.5, 0.5-10, 0.5-9, 0.5-8, 0.5-7, 0.5-6, 0.5-5, 0.5-4, 0.5-3, 0.5-2, 0.5-1, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, the molecular ratio of ICAM-1 and EGFR is 1-6. In some embodiments, the molecular ratio of ICAM-1 and EGFR is 0.1, 0.2, 0.3, 0.4, 0.5, 0.6, 0.7, 0.7, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.7, 6.9, 7, 7.1, 7.2, 7.3, 7.4, 7.5, 7.6, 7.7, 7.7, 7.9, 8, 8.1, 8.2, 8.3, 8.4, 8.5, 8.6, 8.7, 8.7, 8.9, 9.1, 9.2, 9.3, 9.4, 9.5, 9.6, 9.7, 9.7, 9.9, or 10. In some embodiments, the molecular ratio of ICAM-1 and EGFR is 4.2. In some embodiments, the molecular ratio of ICAM-1 and EGFR is 1.5.

By conjugating the ligands of proteins that specifically express or overexpress on the surface of a cancer cell (e.g., EGFR ligands and ICAM-1 ligands) to a liposome, the liposome is specifically directed to and bind to the cancer cell. In some embodiments, the liposome does not bind to normal cells. A "normal cell," as used herein, refers to a non-cancerous cell, or a healthy cell. The liposome "does not bind to a normal cell" means the liposome does not associate with a normal cell, or that the affinity between the liposome and the normal cell is $>10^{-3}$ M (e.g., $10^{-2}$, $10^{-1}$ M, 1 M, or higher). Binding of the ligands to the cancer surface proteins block the signaling of the cancer surface proteins, leading to inhibition of cancer proliferation and growth. In some embodiments, the cancer-targeting liposome of the present disclosure may be used to specifically deliver agents (e.g., anticancer agents) into cancer cells but not to normal cells, thus enhancing specificity of the anticancer agents and reducing adverse effects of the anticancer agents on normal cells.

Thus, some aspects of the present disclosure provide liposome drug delivery systems comprising the any of the liposomes described herein, and a therapeutic agent encapsulated in the liposome. "Encapsulated" means the therapeutic agent is enclosed in the aqueous volume created by the completely closed lipid bilayer of the liposome. The liposome drug delivery system may be designed to target any cell where delivery of the therapeutic agent is desired. One skilled in the art is able to ascertain the cell type and choose appropriate pharmaceutically compositions.

The "agent" encapsulated in the non-cationic liposome may be a physiologically or pharmacologically active substance that acts locally and/or systemically in the body. The agent may be used for the treatment (e.g., therapeutic agent), prevention (e.g., prophylactic agent), or diagnosis (e.g., diagnostic agent) of a disease or disorder. A "therapeutic agent" is an agent that has therapeutic effects on a disease or condition, and may be used to treat a diseases or condition. A therapeutic agent may be a small molecule, an oligonucleotide, a polypeptide or a protein, and combinations thereof.

In some embodiments, the therapeutic agent of the liposome drug delivery system is an anti-cancer agent. An "anti-cancer agent" is any agent that is able to inhibit growth of and/or kills cancer cells, and/or prevent metastasis. In some embodiments, an anti-cancer agent is a chemotherapeutic agent. A "chemotherapeutic agent" is a chemical agent or drugs that are selectively destructive to malignant cells and tissues. Non-limiting, exemplary chemopharmaceutically compositions that may be used in the liposome drug delivery systems of the present disclosure include, Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. In some embodiments, the chemotherapeutic agent is Doxorubicin.

In some embodiments, the anticancer agent is an oligonucleotide (e.g., an siRNA, shRNA, or miRNA targeting an oncogene). An "oncogene" is a gene that in certain circumstances can transform a cell into a tumor cell. An oncogene may be a gene encoding a growth factor or mitogen (e.g., c-Sis), a receptor tysosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPase (e.g., Ras), or a transcription factor (e.g., Myc). In some embodiments, the oligonucleotide targets Lipocalin (Lcn2) (e.g., a Lcn2 siRNA). One skilled in the art is familiar with genes that may be targeted for the treatment of cancer.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. In some embodiments, the anticancer agent is a protein or polypeptide-based anti-cancer agent, e.g., an antibody. Anti-cancer antibodies are known to those skilled in the art.

Non-limiting, exemplary protein or polypeptide-based therapeutic agents include enzymes, regulatory proteins (e.g., immuno-regulatory proteins), antigens, antibodies or antibody fragments, and structural proteins. In some embodiments, the protein or polypeptide-based therapeutic agents are for cancer therapy.

Suitable enzymes for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases.

Non-limiting, exemplary antibodies and fragments thereof include: bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®) and Gliomab-H (indicated for brain cancer, melanoma). Other antibodies and antibody fragments are contemplated and may be used in accordance with the disclosure.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1.

As used herein, an immunoregulatory protein is a protein that regulates an immune response. Non-limiting examples of immunoregulatory include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunostimulatory proteins are contemplated and may be used in accordance with the disclosure.

As used herein, an antigen is a molecule or part of a molecule that is bound by the antigen-binding site of an antibody. In some embodiments, an antigen is a molecule or moiety that, when administered to or expression in the cells of a subject, activates or increases the production of antibodies that specifically bind the antigen. Antigens of pathogens are well known to those of skill in the art and include, but are not limited to parts (coats, capsules, cell walls, flagella, fimbriae, and toxins) of bacteria, viruses, and other microorganisms. Examples of antigens that may be used in accordance with the disclosure include, without limitation, cancer antigens, self-antigens, microbial antigens, allergens and environmental antigens.

In some embodiments, the antigen of the present disclosure is a cancer antigen. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-05. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2. Other cancer antigens are contemplated and may be used in accordance with the disclosure.

The liposomes or liposome drug delivery systems of the present disclosure may be formulated in pharmaceutical compositions. In some embodiments, the pharmaceutical composition further comprises a pharmaceutically acceptable carrier. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the pharmaceutical composition may dependent upon the route of administration. Injectable preparations suitable for parenteral administration or intra-tumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

For topical administration, the pharmaceutical composition can be formulated into ointments, salves, gels, or creams, as is generally known in the art. Topical administration can utilize transdermal delivery systems well known in the art. An example is a dermal patch.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The cyclic Psap peptide and/or the pharmaceutical composition ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

Other aspects of the present disclosure provide methods of treating cancer (e.g., TNBC), the methods comprising administering to a subject in need thereof a therapeutically effective amount of a liposome or a liposome drug delivery system described herein. In some embodiments, the liposome or the drug delivery system targets TNBC. In some embodiments, the liposome or the drug delivery system comprises an EGFR ligand and a ICAM-1 ligand conjugated to the liposome surface. In some embodiments, the molecular ratio of the EGFR ligand and the ICAM-1 ligand complements the density of EGFR and ICAM-1 on TNBC surface. In some embodiments, the liposome of the drug delivery system inhibits EGFR and/or ICAM-1 signaling. "Inhibits signaling" means any measurable signaling intensity triggered by activation of EGFR or ICAM-1 is reduced (e.g., by at least 10%, at least 20%, at least 30%, at least 40%, at least 50%, at least 60%, at least 70%, at least 80%, at least 90%, at least 95%, at least 99%, or 100%). In some embodiments, inhibiting EGFR and/or ICAM-1 signaling inhibits tumor growth and/or proliferation. In some embodiments, the therapeutic agent encapsulated in the liposome is delivered specifically to cancer cells and inhibits tumor cell growth and/or proliferation, reduce tumor size, or kills cancer cells.

In some embodiments, the cancer-targeting liposomes or the liposome drug delivery systems described herein are effective in reducing tumor size, slowing rate of tumor growth, reducing cell proliferation of the tumor, promoting cancer cell death, inhibiting angiogenesis, inhibiting metastasis, or otherwise improving overall clinical condition, without necessarily eradicating the cancer. In some embodiments, the cancer-targeting liposomes or the liposome drug delivery systems described herein are effective in eradicating the cancer.

In some embodiments, the compositions and methods of the present disclosure, when administered to the subject, prevents metastasis of the cancer. The term "metastasis" refers to the spread of a primary tumor from one organ or part of the body to another not directly connected with it. A "primary tumor" refers to a tumor growing at the anatomical site where tumor progression began and proceeded to yield a cancerous mass. Most cancers develop at their primary site but then go on to spread to other parts of the body, i.e., metastasis. These further tumors are secondary tumors. Metastasis results from several interconnected processes including cell proliferation, angiogenesis, cell adhesion, migration, and invasion into the surrounding tissue. The term "prevent metastasis" means the process of a primary to spread to other parts of the body that is not directly connected is inhibited, or that the development of the secondary tumor is prevented.

The term "inhibits growth and/or proliferation" (e.g., referring to cancer or tumor cells) is intended to include any measurable decrease in the growth of a cell when contacted with a cancer-targeting liposome as compared to the growth of the same cell not in contact with the cancer-targeting liposome, e.g., the inhibition of growth of a cell by at least about 10%, 20%, 30%, 40%, 50%, 60%, 70%, 80%, 90%, 99%, or 100%).

The term "reduce tumor size," as used herein, refers to the decrease in tumor size compared to before the subject was treated using the methods and the compositions of the present disclosure. In some embodiments, the tumor size is reduced by at least 10%, at least 20%, at least 30%, at least 50%, at least 60%, at least 70%, at least 80%, at least 90%, at least 99%. In some embodiments, the tumor size is reduced by 100%, i.e., the tumor disappears. In some embodiments, the tumor is reduced to no more that 80%, no more than 70%, no more than 60%, no more than 40%, no more than 30%, no more than 20%, no more than 10% no more than 5%, no more than 1%, or no more than 0.1% of its original size. The term "kills cancer cells" means causing death to cancer cells, e.g., via apoptosis or necrosis.

In its broadest sense, the terms "treatment" or "to treat" refer to both therapeutic and prophylactic treatments. If the subject in need of treatment has cancer, then "treating the condition" refers to ameliorating, reducing or eliminating one or more symptoms associated with the cancer or the severity of cancer or preventing any further progression of cancer. If the subject in need of treatment is one who is at risk of having cancer, then treating the subject refers to reducing the risk of the subject having cancer or preventing the subject from developing cancer.

A subject shall mean a human or vertebrate animal or mammal including but not limited to a rodent, e.g., a rat or a mouse, dog, cat, horse, cow, pig, sheep, goat, turkey, chicken, and primate, e.g., monkey. The methods of the present disclosure are useful for treating a subject in need thereof. A subject in need thereof can be a subject who has a risk of developing cancer (i.e., via a genetic test) or a subject who has cancer.

Pharmaceutically compositions, e.g., cancer-targeting liposomes or liposome drug delivery systems, that may be used in accordance with the present disclosure may be directly administered to the subject or may be administered to a subject in need thereof in a therapeutically effective amount. The term "therapeutically effective amount" refers to the amount necessary or sufficient to realize a desired biologic effect. For example, a therapeutically effective amount of a cancer-target liposome associated with the present disclosure may be that amount sufficient to ameliorate one or more symptoms of cancer. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular pharmaceutically compositions being administered the size of the subject, or the severity of the disease or condition. One of ordinary skill in the art can empirically determine the effective amount of a particular therapeutic compound associated with the present disclosure without necessitating undue experimentation.

Subject doses of the cancer-targeting liposomes or liposome drug delivery systems described herein for delivery typically range from about 0.1 µg to 10 mg per administration, which depending on the application could be given daily, weekly, or monthly and any other amount of time there between. In some embodiments a single dose is administered during the critical consolidation or reconsolidation period. The doses for these purposes may range from about 10 µg to 5 mg per administration, and most typically from about 100 µg to 1 mg, with 2-4 administrations being spaced, for example, days or weeks apart, or more. In some embodiments, however, parenteral doses for these purposes may be used in a range of 5 to 10,000 times higher than the typical doses described above.

In some embodiments, a cancer-targeting liposome or liposome drug delivery system of the present disclosure is administered at a dosage of between about 1 and 10 mg/kg of body weight of the mammal. In other embodiments a cancer-targeting liposome or liposome drug delivery system of the present disclosure is administered at a dosage of between about 0.001 and 1 mg/kg of body weight of the mammal. In yet other embodiments, a cancer-targeting liposome or liposome drug delivery system of the present disclosure is administered at a dosage of between about 10-100 ng/kg, 100-500 ng/kg, 500 ng/kg-1 mg/kg, or 1-5 mg/kg of body weight of the mammal, or any individual dosage therein.

The formulations of the present disclosure are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the therapeutic compound associated with the present disclosure can be administered to a subject by any mode that delivers the therapeutic agent or compound to the desired surface, e.g., mucosal, injection to cancer, systemic, etc. Administering the pharmaceutical composition of the present disclosure may be accomplished by any means known to the skilled artisan. Preferred routes of administration include but are not limited to oral, parenteral, intravenous, intramuscular, intranasal, sublingual, intratracheal, inhalation, ocular, vaginal, rectal and intracerebroventricular.

For oral administration, the pharmaceutically compositions of the present disclosure can be formulated readily by combining the active compound(s) with pharmaceutically acceptable carriers well known in the art. Such carriers enable the compounds of the present disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The pharmaceutical compositions can be included in the formulation as fine multi particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The pharmaceutical compositions of the present disclosure, when desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The pharmaceutical compositions of the present disclosure and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the present disclosure contain an effective amount of a therapeutic compound of the present disclosure optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

The pharmaceutical compositions may be delivered to the brain using a formulation capable of delivering a therapeutic agent across the blood brain barrier. One obstacle to delivering therapeutics to the brain is the physiology and structure of the brain. The blood-brain barrier is made up of specialized capillaries lined with a single layer of endothelial cells. The region between cells are sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipophilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. Others are known to those of skill in the art.

The pharmaceutical compositions of the present disclosure may be delivered with other therapeutics for treating cancer.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Further provided herein are methods of making cancer-targeting liposomes (e.g., complementary cancer targeting liposomes). The expression level of cell surface proteins of a cancer cell may be qualified and profiled, allowing selection of overexpressed surface proteins (e.g., membrane proteins) as targets of the cancer-targeting liposome. Further, the relative molecule density (i.e., ratio) of the selected targets may be calculated, allowing engineering of complementary cancer-targeting liposomes by conjugating ligands targeting the surface proteins to the surface of the liposome at molecular ratios that complement the relative molecular density (i.e., ratio) of the targets.

Different cancer/tumor cells can show distinct morphological and phenotypic profiles, including cellular morphology, gene expression, metabolism, motility, proliferation, and metastatic potential. This phenomenon occurs both between tumor (inter-tumor heterogeneity) and within tumors (intra-tumor heterogeneity). The heterogeneity of cancer cells introduces significant challenges in designing effective treatment strategies. The methods provided herein may be utilized for personalized cancer therapy. Cancer cells from each patient, or each tumor site from one patient, may be profiled for their unique relative molecular density (i.e., ratio) on the cell surfaces. Complementary liposomes may be designed to for each relative molecular density (i.e., ratio), thereby allowing highly specific and potent targeting of different types of cancers.

The present disclosure is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1 Complementary Engineered Liposomes (CELs)

Triple negative breast cancer (TNBC), an aggressive form of breast cancer, is defined by the absence of estrogen receptor (ER), progesterone receptor (PR), and human epidermal growth factor receptor type 2 (HER2). The current prognosis for TNBC patients remains poor due to unresectable metastases and lack of effective targeted therapeutics. A number of TNBC molecular targets have been discovered over the past decades, including EGFR, CD44, Integrin $\alpha v\beta 3$ and ICAM-1. EGFR-targeted liposomes and nanoparticles demonstrated 1.5-4 fold enhanced uptake by TNBC cells relative to the control, which results in 1.3-2 fold increased tumor accumulation. Similarly, CD44-targeted liposomes exhibited 1.5 and 2-fold increased affinity to TNBC cell lines (in vitro) and tumors (in vivo) relative to the control. Integrin $\alpha v\beta 3$-targeted liposomes and nanoparticles exhibited 2 and 2.2-fold increases compared to the control. ICAM-1 antibody conjugated iron oxide nanoparticles demonstrated 2.4 to 4-fold higher binding with various TNBC cells in comparison with non-neoplastic controls, and result in a 2.6-fold increase in TNBC tumor accumulation. Nevertheless, targeted therapeutics based on these TNBC molecular targets have had limited success in clinical trials due to "off-target" effects.

To overcome this obstacle, a "dual-ligand targeting" approach has been developed to enhance tumor specificity and reduce non-specific binding by simultaneously targeting two overexpressing molecular targets on the cancer cell's surface. This approach is well adapted by nanoscale drug delivery systems (nanoDDSs) due to their large surface area with abundant active functional groups. Several dual-ligand targeting nanoDDSS have been reported to enhance drug delivery efficacy via targeting Integrin $\alpha v\beta 3$/Interleukin-13 receptor (glioblastoma), Folate receptor/EGFR (cervical cancer), and carcinoembryonic antigen/neurotensin receptor (colorectal cancer). However, the mechanism of dual-ligand targeting is still not well elucidated, and the role of molecular target density and organization on cancer cell surface in interacting with dual targeting ligands need further investigation.

In this study, a novel dual targeting strategy that precisely complements the relative molecular density of two highly overexpressed membrane proteins was developed. Unlike conventional therapeutics that present a single-targeting ligand on the surface of a drug delivery nanocarrier, complementary engineered liposomes (CELs) present two targeting ligands at an optimal molecular density based on measurements of a specific TNBC cell line. This method may provide more specific and cooperative adhesion of liposomal vehicles to TNBC cells. This personalized approach to targeting TNBC cells via CELs may provide an opportunity for developing more precise and effective TNBC-targeted therapeutics.

Results and Discussion
Screen and Identify ICAM-1 and EGFR as the TNBC Dual-Targeting Combination Although precise mechanisms of TNBC tumorigenesis remain to be clarified, a number of biomolecules were found as critical factors involving in TNBC tumor growth, angiogenesis, and metastasis, such as EGFR, ICAM-1, CXCR4 and CD44. The feasibility of these biomolecules as potential targets for TNBC-specific drug delivery are often lacking quantitative surface protein characterization. Ideally, a TNBC molecular target should overexpress exclusively on TNBC cells with no or minimum expression on non-neoplastic cells. Thus, flow cytometry analysis was used to measure the overexpression profiles of 12 potential TNBC molecular targets including CXCR4, CCR2, CCR5, CCR7, ICAM-1, VCAM-1, E-Cadherin, N-Cadherin, EGFR, HER2, CD44, and CD24 in human TNBC MDA-MB-231 and MDA-MB-436 cells and non-neoplastic MCF10A cells. As shown in FIG. 1, amongst these 12 proteins, ICAM-1 and EGFR consistently demonstrated the highest elevated expression levels in both MDA-MB-231 and MDA-MB-436 cells with significantly lower expression levels in non-neoplastic MCF10A cells, which made them ideal as a dual target combination. It was also observed that CD44, a cancer stem cell biomarker and widely used nanomedicine target, was highly overexpressed in non-neoplastic MCF10A cells, which may result in "off-target" binding. Molecular densities of ICAM-1 and EGFR on TNBC cell membranes were also compared. As shown in Table 1, the expression levels of both ICAM-1 and EGFR on TNBC cells are significantly higher than those on MCF10As, and the optimal ratio between two proteins (ICAM-1:EGFR, mol/mol) was 4.2:1 for MDA-MB-231 cells and 1.5:1 for MDA-MB-436 and MCF10A cells. The ICAM-1/EGFR ratios of 198 human TNBC patients were quantified based on their gene expression levels using R2:Genomics Analysis and Visualization Platform (hgserver1.amc.nl), which ranges from 0.027 to 8.92 (Table 2).

TABLE 1

Collection of human TNBC and normal cell lines with their ICAM-1 and EGFR surface protein densities measured by flow cytometry.

| Cell line | ER | PR | HER2 | Invasiveness | ICAM1 (molecules/cell) | EGFR (molecules/cell) | Ratio (ICAM1:EGFR) |
|---|---|---|---|---|---|---|---|
| MDA-MB-231 | — | — | — | High | 2,350,000 ± 25,000 | 559,000 ± 1,200 | 4.2:1 |
| MDA-MB-436 | — | — | — | Medium | 756,000 ± 7,600 | 514,000 ± 2,200 | 1.5:1 |
| MCF10A | — | — | — | Low | 93,000 ± 2,300 | 61,200 ± 740 | 1.5:1 |

TABLE 2

ICAM-1/EGFR ratios of 198 human TNBC patients (gene expression)

| Patient number | Relative ratio of ICAM-1/EGFR (gene expression) |
|---|---|
| gsm1974566 | 1.20821727 |
| gsm1974567 | 2.827765405 |
| gsm1974568 | 0.222703063 |
| gsm1974569 | 0.145675765 |
| gsm1974570 | 0.213500785 |
| gsm1974571 | 0.509664293 |
| gsm1974572 | 0.308065494 |
| gsm1974573 | 0.097282948 |
| gsm1974574 | 0.986099755 |
| gsm1974575 | 1.23231441 |
| gsm1974576 | 0.265207715 |
| gsm1974577 | 0.338688086 |
| gsm1974578 | 0.912970711 |
| gsm1974579 | 0.69379845 |
| gsm1974580 | 0.848484848 |
| gsm1974581 | 0.106336489 |
| gsm1974582 | 1.116846105 |
| gsm1974583 | 0.602102102 |
| gsm1974584 | 0.094094488 |
| gsm1974585 | 0.145211931 |
| gsm1974586 | 2.919035314 |
| gsm1974587 | 0.244680851 |
| gsm1974588 | 0.68614196 |
| gsm1974589 | 1.041328413 |
| gsm1974590 | 5.116957105 |
| gsm1974591 | 1.012494794 |
| gsm1974592 | 1.105433186 |
| gsm1974593 | 2.412206855 |
| gsm1974594 | 0.549898443 |
| gsm1974595 | 1.130693069 |
| gsm1974596 | 0.468515572 |
| gsm1974597 | 0.43803056 |
| gsm1974598 | 0.118170267 |
| gsm1974599 | 0.67308574 |
| gsm1974600 | 0.820647419 |
| gsm1974601 | 0.370057752 |
| gsm1974602 | 0.248878924 |
| gsm1974603 | 0.168153981 |
| gsm1974604 | 8.920444033 |
| gsm1974605 | 7.291044776 |
| gsm1974606 | 0.625493291 |
| gsm1974607 | 0.091489657 |
| gsm1974608 | 5.130699088 |
| gsm1974609 | 0.961603614 |
| gsm1974610 | 0.195699595 |
| gsm1974611 | 1.397149461 |
| gsm1974612 | 0.85966634 |
| gsm1974613 | 1.883273165 |
| gsm1974614 | 0.9661087 |
| gsm1974615 | 4.494054054 |
| gsm1974616 | 1.926470588 |
| gsm1974617 | 0.87322695 |
| gsm1974618 | 0.962655602 |
| gsm1974619 | 0.625308135 |
| gsm1974620 | 0.10203125 |
| gsm1974621 | 0.299448385 |
| gsm1974622 | 0.251046025 |
| gsm1974623 | 0.189655172 |
| gsm1974624 | 0.194954128 |
| gsm1974625 | 0.866666667 |
| gsm1974626 | 0.299084519 |
| gsm1974627 | 0.322376009 |
| gsm1974628 | 1.326086957 |
| gsm1974629 | 0.280373832 |
| gsm1974630 | 1.016 |
| gsm1974631 | 3.221633086 |
| gsm1974632 | 0.451851852 |
| gsm1974633 | 0.541910331 |
| gsm1974634 | 0.174487472 |
| gsm1974635 | 1.057950192 |
| gsm1974636 | 0.060518135 |
| gsm1974637 | 5.689655172 |
| gsm1974638 | 0.75 |
| gsm1974639 | 0.387244898 |
| gsm1974640 | 0.178825841 |
| gsm1974641 | 1.670454545 |
| gsm1974642 | 0.075746406 |
| gsm1974643 | 0.218994064 |
| gsm1974644 | 0.275302183 |
| gsm1974645 | 0.843987823 |
| gsm1974646 | 0.469846985 |
| gsm1974647 | 1.163069544 |
| gsm1974648 | 0.899253731 |
| gsm1974649 | 0.420439845 |
| gsm1974650 | 0.182437746 |
| gsm1974651 | 0.026671168 |
| gsm1974652 | 0.2699603 |
| gsm1974653 | 0.550290568 |
| gsm1974654 | 1.124590164 |
| gsm1974655 | 0.699047619 |

TABLE 2-continued

ICAM-1/EGFR ratios of 198 human TNBC patients (gene expression)

| Patient number | Relative ratio of ICAM-1/EGFR (gene expression) |
|---|---|
| gsm1974656 | 2.076 |
| gsm1974657 | 1 |
| gsm1974658 | 1.710497238 |
| gsm1974659 | 7.818756586 |
| gsm1974660 | 0.588015717 |
| gsm1974661 | 0.072087759 |
| gsm1974662 | 0.076040782 |
| gsm1974663 | 0.35745752 |
| gsm1974664 | 1.801843318 |
| gsm1974665 | 0.332643559 |
| gsm1974666 | 0.707992895 |
| gsm1974667 | 0.389342295 |
| gsm1974668 | 0.966898955 |
| gsm1974669 | 0.182654402 |
| gsm1974670 | 2.886765747 |
| gsm1974671 | 0.724091521 |
| gsm1974672 | 0.547377327 |
| gsm1974673 | 1.020168067 |
| gsm1974674 | 0.529505582 |
| gsm1974675 | 0.488457987 |
| gsm1974676 | 0.141445046 |
| gsm1974677 | 0.428685897 |
| gsm1974678 | 0.464972527 |
| gsm1974679 | 0.409529942 |
| gsm1974680 | 0.304835924 |
| gsm1974681 | 1.092573754 |
| gsm1974682 | 0.229647965 |
| gsm1974683 | 0.188361094 |
| gsm1974684 | 0.290626131 |
| gsm1974685 | 0.528862479 |
| gsm1974686 | 0.131143776 |
| gsm1974687 | 0.415936953 |
| gsm1974688 | 0.885429639 |
| gsm1974689 | 0.791989664 |
| gsm1974690 | 0.14295025 |
| gsm1974691 | 0.599925844 |
| gsm1974692 | 1.1264 |
| gsm1974693 | 0.126601743 |
| gsm1974694 | 0.18655303 |
| gsm1974695 | 0.438484252 |
| gsm1974696 | 1.351162791 |
| gsm1974697 | 1.179012346 |
| gsm1974698 | 1.960987654 |
| gsm1974699 | 0.288637968 |
| gsm1974700 | 0.600244002 |
| gsm1974701 | 0.705839593 |
| gsm1974702 | 0.190265487 |
| gsm1974703 | 0.202497367 |
| gsm1974704 | 0.44165247 |
| gsm1974705 | 0.072292895 |
| gsm1974706 | 0.538028169 |
| gsm1974707 | 0.380848749 |
| gsm1974708 | 0.101091992 |
| gsm1974709 | 0.228691197 |
| gsm1974710 | 1.06681191 |
| gsm1974711 | 0.814488636 |
| gsm1974712 | 0.37816625 |
| gsm1974713 | 0.38997949 |
| gsm1974714 | 0.357263718 |
| gsm1974715 | 0.108675799 |
| gsm1974716 | 0.274605817 |
| gsm1974717 | 0.289240506 |
| gsm1974718 | 1.073929961 |
| gsm1974719 | 0.093116806 |
| gsm1974720 | 0.963592233 |
| gsm1974721 | 1.079826464 |
| gsm1974722 | 0.638918919 |
| gsm1974723 | 0.102491772 |
| gsm1974724 | 2.468473896 |
| gsm1974725 | 0.317283431 |
| gsm1974726 | 0.33639901 |
| gsm1974727 | 0.45473251 |
| gsm1974728 | 3.408906883 |
| gsm1974729 | 0.499378882 |
| gsm1974730 | 1.077795786 |
| gsm1974731 | 0.597923277 |
| gsm1974732 | 0.907027818 |
| gsm1974733 | 0.245983254 |
| gsm1974734 | 0.386771911 |
| gsm1974735 | 0.940464178 |
| gsm1974736 | 3.387375415 |
| gsm1974737 | 0.150097466 |
| gsm1974738 | 0.309976992 |
| gsm1974739 | 0.525456292 |
| gsm1974740 | 1.488259109 |
| gsm1974741 | 0.237994847 |
| gsm1974742 | 1.6 |
| gsm1974743 | 0.833543506 |
| gsm1974744 | 0.552263374 |
| gsm1974745 | 0.202085581 |
| gsm1974746 | 0.324298161 |
| gsm1974747 | 0.461179762 |
| gsm1974748 | 0.04777138 |
| gsm1974749 | 0.388432703 |
| gsm1974750 | 0.283960588 |
| gsm1974751 | 0.143002804 |
| gsm1974752 | 0.420816733 |
| gsm1974753 | 0.153866667 |
| gsm1974754 | 0.56254093 |
| gsm1974755 | 0.706733609 |
| gsm1974756 | 0.678717599 |
| gsm1974757 | 0.223839854 |
| gsm1974758 | 0.905998209 |
| gsm1974759 | 2.302017654 |
| gsm1974760 | 0.167188478 |
| gsm1974761 | 3.931034483 |
| gsm1974762 | 0.230306249 |
| gsm1974763 | 0.435661765 |

Figure 2A:
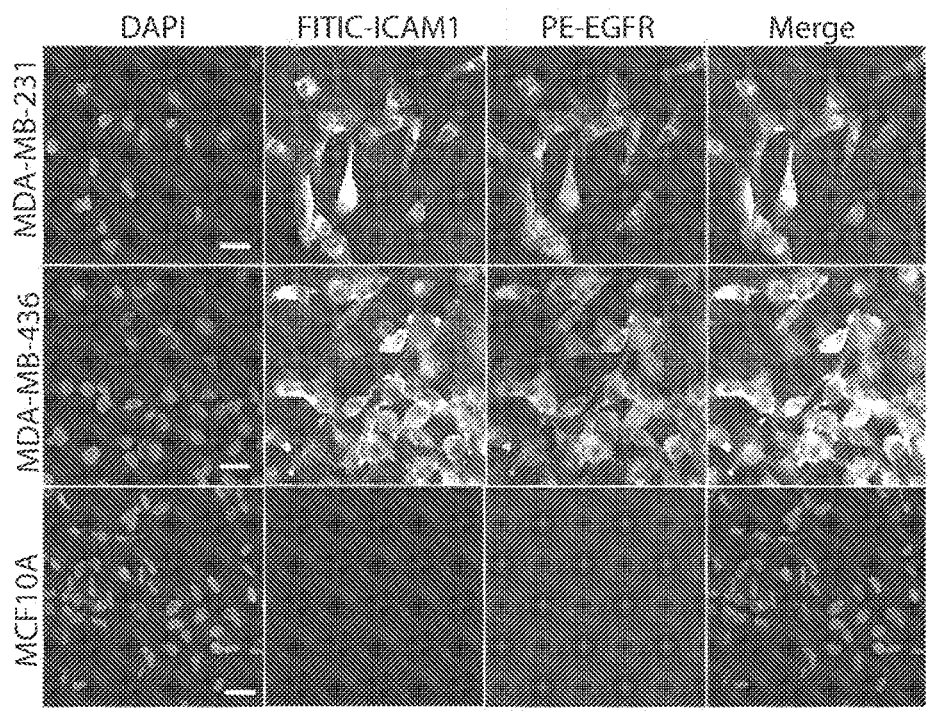
FIGS. 2A-2C show representative fluorescence microscope images (FIG. 2A) of ICAM-1 and EGFR immunofluorescent co-staining in MDA-MB-231, MDA-MB-436, and MCF10A (control) cells. DAPI was used to stain the cell nuclei; FITC-conjugated rat anti-human ICAM-1 antibody was used to stain ICAM-1; PE-conjugated mouse anti-human EGFR antibody was used to EGFR. Scale bars represent 20 μm. ICAM-1 (FIG. 2B) and EGFR (FIG. 2C) gene expression in human TNBC and normal cells quantified by qRT-PCR. ICAM-1 and EGFR fold changes are relative to GAPDH. *** $P<0.001$

The organization of ICAM-1 and EGFR on TNBC cell surface was measured by immunofluorescent staining. As shown in FIG. 2A, both proteins were overexpressed relative to MCF-10A and were co-localized in two TNBC cell lines, indicating they may be simultaneously recognized and accessed by CELs via a dual-targeting approach. The overlapped expression of ICAM-1 and EGFR increase the total local molecular density of targeting proteins for both MDA-MB-231 and MDA-MB-436 cells, which were 1.2 to 2.4-fold higher than the individual protein density.

Figure 2B:
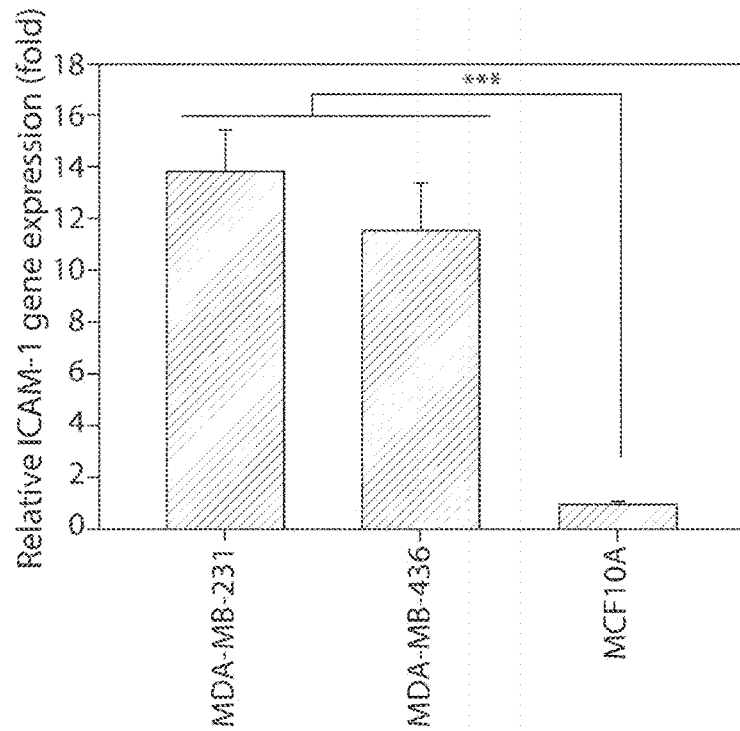
Figure 2C:
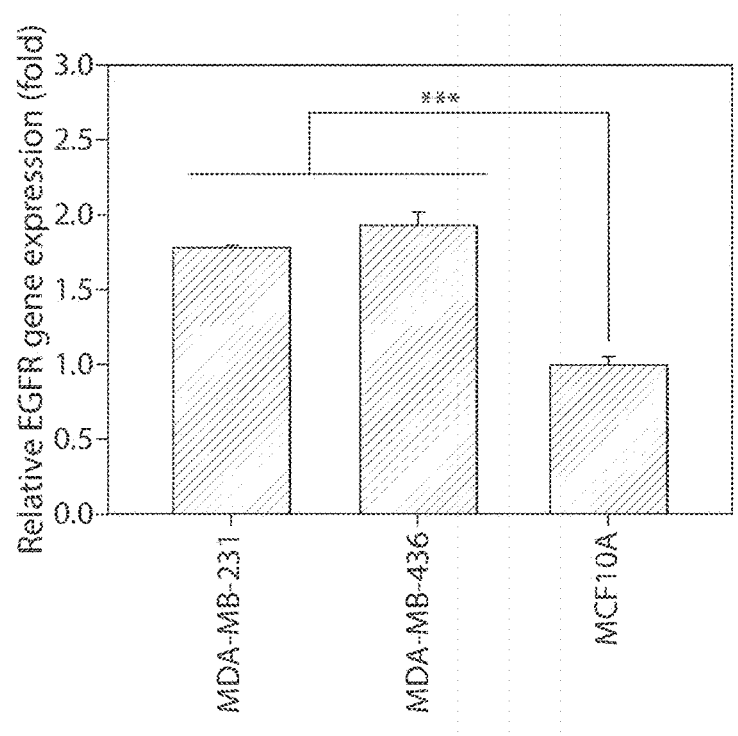

Gene expression levels of ICAM-1 and EGFR in TNBC cells were also quantified by qRT-PCR. The mRNA levels of ICAM-1 and EGFR were significantly elevated in both TNBC cell lines (FIGS. 2B and 2C), which correlated well with surface protein levels. Thus, based on the quantitative analysis, ICAM-1 and EGFR were selected as the target combination for the complementary, dual-targeting study.

Prepare and Characterize CEL-Dox

Figure 3:
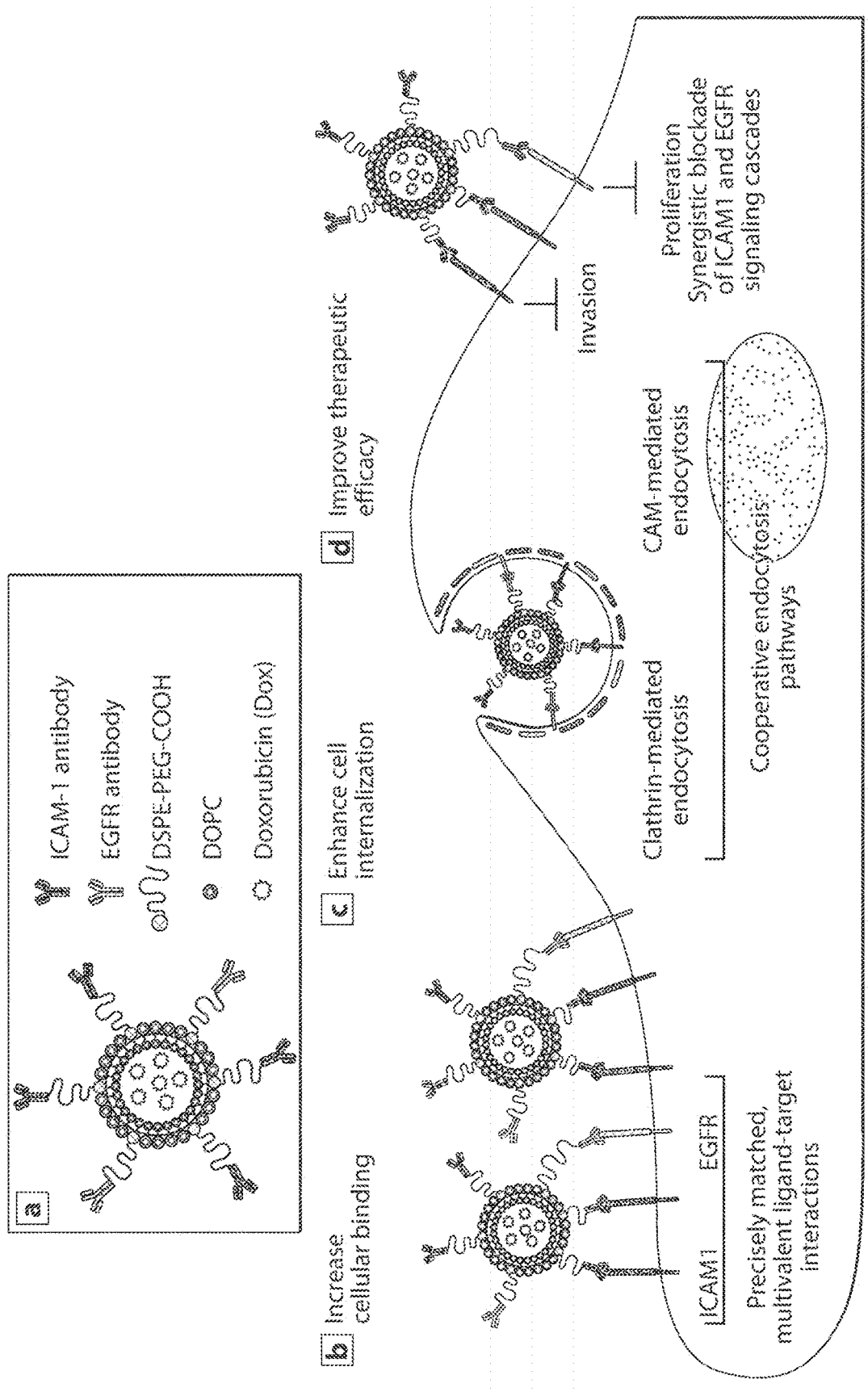
FIG. 3 is a schematic illustration of dual complementary liposome (DCL) structure and biomechanisms of complementary targeting strategy. (a) The design of the proof-of-principle binary DCL for TNBC. (b) DCL increases cellular binding using precisely matched, multivalent ligand-receptor interactions. (c) DCL enhances internalization using cooperative ICAM1 and EGFR endocytosis pathways. (d)

In order to evaluate the effectiveness of dual-targeting, the CEL-Dox was engineered to simultaneously complement the molecular density and organization of ICAM-1 and EGFR on TNBC cell membranes (as shown in FIG. 3). Dox was actively loaded into liposomes via a transmembrane gradient. ICAM-1 and EGFR antibodies in optimal molar ratios were covalently conjugated on the liposome surface via EDC/NHS chemistry. Non-specific IgG conjugated liposomal doxorubicin (IgG-Dox-LP), ICAM-1 antibody conjugated liposomal doxorubicin (ICAM-1-Dox-LP), EGFR antibody conjugated liposomal doxorubicin (EGFR-Dox-LP) and CEL-Dox at ICAM-1:EGFR antibody ratios (4.2:1, 1.5:1, or 1:1) were constructed. As-synthesized CELs were characterized by dynamic light scattering measurements and demonstrated a number-averaged hydrodynamic diameter of 120 nm with a narrow size distribution (Table 3). Surface charges of CELs were negative, similar to the control IgG, ICAM-1, and EGFR conjugated liposomes. The Dox encapsulation efficiency of the different CEL formulations were approximately 97%, which correlates with previous reports.

The ICAM-1:EGFR antibody ratio presented on CELs plays a pivotal role in the targeting process. The ICAM-1 and EGFR antibody densities and ratios were quantitatively characterized on different CELs via microbead assay. As shown in Table 4, all CELs demonstrated a total antibody density of approximately 4,500 molecules per um$^2$, equivalent to 130 antibodies per liposome. The experimental ICAM-1:EGFR ratios after EDC/NHS conjugation closely correlated with theoretical values, indicating the successful conjugation of ICAM-1 and EGFR antibodies on the surface of CELs at optimal ratios. ICAM-1 and EGFR antibodies conjugated on CEL surfaces (4:1 for CEL_4.2/1 and 1.2:1 for CEL_1.5/1) can closely complement the ICAM-1 and EGFR molecular density on TNBC cells (4.2:1 for MDA-MB-231 cells and 1.5:1 for MDA-MB-436 cells), which facilitates the synergistic dual-ligand targeting. Meanwhile, these CELs are expected to have less binding with non-neoplastic MCF10A cells than ICAM-1/EGFR single-targeting liposomes, because these CELs exhibited 1.2-4.8-fold decreased ICAM-1/EGFR antibody densities in comparison with ICAM-1/EGFR single targeting liposomes.

TABLE 3

Hydrodynamic diameter, size distribution, zeta potential, and dox encapsulation ratio of as synthesized immunoliposomes.

| Sample | Size (nm) | PDI | Zeta-potential (mV) | Dox Encapsulation Efficiency (%) |
|---|---|---|---|---|
| IgG-Dox-LP | 128 ± 32 | 0.050 | −10.8 ± 0.7 | 98.1 ± 2.2 |
| ICAM1-Dox-LP | 123 ± 21 | 0.022 | −8.2 ± 1.9 | 97.8 ± 0.7 |
| EGFR-Dox-LP | 125 ± 25 | 0.026 | −8.0 ± 0.6 | 97.6 ± 2.3 |
| CEL-Dox_4.2/1 | 132 ± 20 | 0.015 | −6.3 ± 1.6 | 98.6 ± 2.2 |
| CEL-Dox_1.5/1 | 133 ± 26 | 0.022 | −5.6 ± 0.7 | 98.5 ± 0.4 |
| CEL-Dox_1/1 | 132 ± 13 | 0.009 | −6.2 ± 0.9 | 97.9 ± 2.9 | single targeting liposomes and the IgG control (2.6-fold vs. IgG-RD-LPs). Similarly, CELs with an ICAM-1:EGFR antibody ratio of 1.5:1 (CEL 1.5:1) complemented the protein expression on MDA-MB-436 cells and demonstrated the greatest liposome binding with MDA-MB-436 cells relative to single targeting liposomes and the IgG control (2.3-fold vs. IgG-RD-LP). No significant difference in binding was observed between CELs and single targeting liposomes to non-neoplastic MCF10A cells. These quantitative flow cytometry measurements validate that CELs that match the TNBC protein expression can significantly increase TNBC specificity via dual-targeting, in comparison with single targeting liposomes or CELs at non-optimal antibody ratios.

ICAM-1 Antibodies on CEL Inhibit TNBC Cell Invasion

Figure 5A:
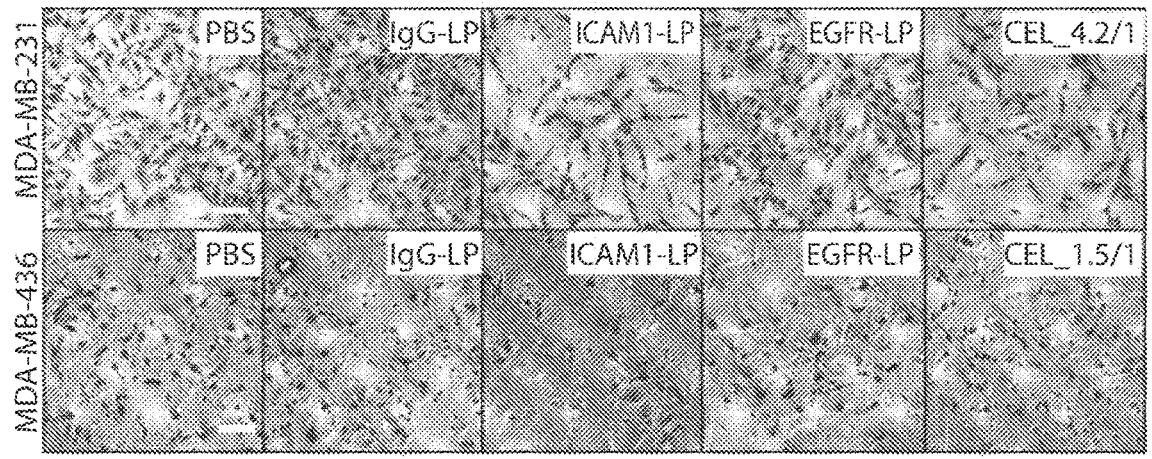
FIGS. 5A-5H show that ICAM-1 antibody presented on CELs serves as both targeting ligand and pharmaceutically compositions for inhibiting TNBC cell invasion.
Figure 5B:
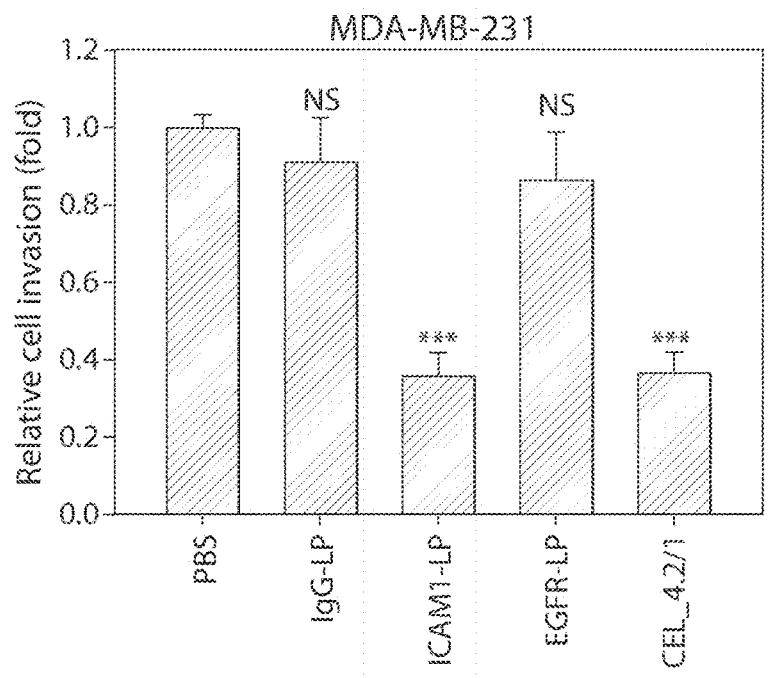
Figure 5C:
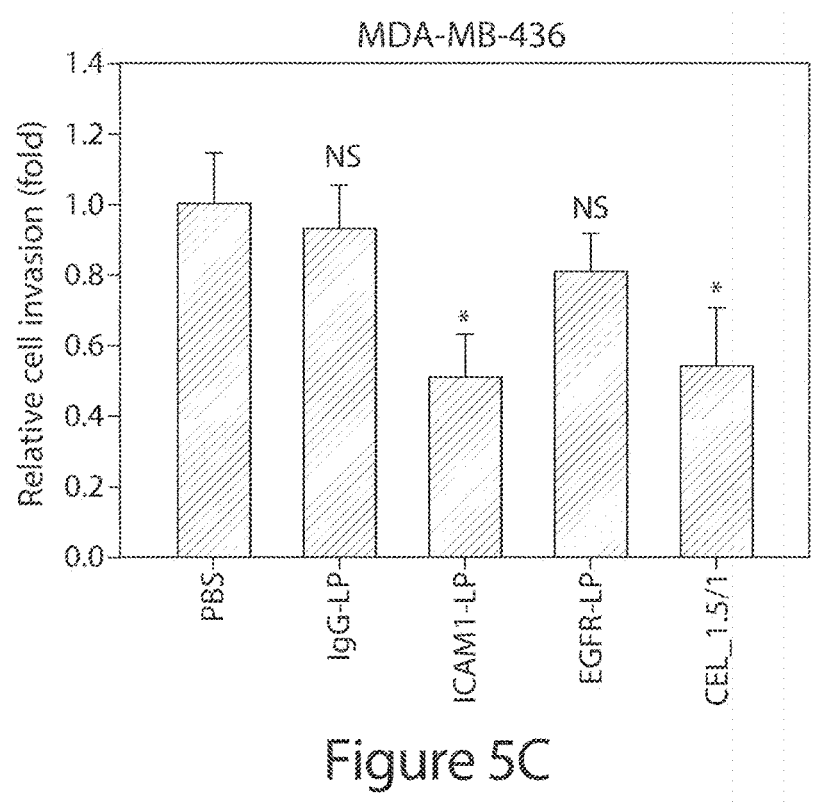

ICAM-1 was previously found to play a role in TNBC metastasis. Free ICAM-1 antibodies exhibited potent activity in inhibiting breast cancer cell invasion via blocking the ICAM-1 signaling cascade. This prompted an examination of the therapeutic potential of ICAM-1 antibodies conjugated on CELs in inhibiting TNBC metastasis. The inhibitory effect of CELs on TNBC cell invasion was assessed. Empty CELs without Dox were used in this study to exclude interference with cytotoxicity. Human TNBC MDA-MB-231 and MDA-MB-436 cells were pre-incubated with IgG-LP, ICAM-1-LP, EGFR-LP, or CELs at optimal antibody ratios (CEL_4.2:1 for MDA-MB-231 cells, and CEL_1.5:1 for MDA-MB-436 cells) for 24 hours and then transferred to matrigel coated transwell membranes. As shown in FIGS. 5A-5C, the TNBC cells treated with the (ICAM-1-LP and CELs had remarkably reduced number of invading cells than TNBC cells treated with either IgG-LP or EGFR-LP. CELs can efficiently inhibit MDA-MB-231 and MDA-MB-436 cell invasion cell by 64% and 73%, respectively, relative to IgG-LPs. The inhibitory effect of CELs was slightly lower than the ICAM-1-LPs, probably due to the decreased ICAM-1 antibody density on the CEL surface in comparison with that of the ICAM-1-LPs. The CELs of the present disclosure exhibit a secondary therapeutic effect by inhibiting TNBC cell invasion, in addition to the TNBC-specific delivery of Dox. These CELs may represent a multifunctional and synergistic therapeutic platform for TNBC treatment.

TABLE 4

Quantitative analysis of antibody density of as-synthesized immunoliposomes.

| Sample | ICAM1:EGFR Ratio (Theoretical) | ICAM1 Density (molecules/μm$^2$) | EGFR Density (molecules/μm$^2$) | IgG Density (molecules/μm$^2$) | Total Antibody density (molecules/μm$^2$) | ICAM1:EGFR Ratio (Experimental) |
|---|---|---|---|---|---|---|
| IgG-Dox-LP | NA | 0 | 0 | 4,236 ± 180 | 4,236 ± 180 | NA |
| ICAM1-Dox-LP | 1:0 | 4,527 ± 316 | 0 | 0 | 4,527 ± 315 | 1:0 |
| EGFR-Dox-LP | 0:1 | 0 | 4,455 ± 43 | 0 | 4,455 ± 43 | 0:1 |
| CEL-Dox_4.2/1 | 4.2:1 | 3,547 ± 93 | 925 ± 88 | 0 | 4,572 ± 181 | 4.0:1 |
| CEL-Dox_1.5/1 | 1.5:1 | 2,609 ± 42 | 2,230 ± 43 | 0 | 4,840 ± 6 | 1.2:1 |
| CEL-Dox_1/1 | 1:1 | 2,406 ± 88 | 2,364 ± 132 | 0 | 4,770 ± 173 | 1.02:1 |

CELs at Optimal Antibody Ratio Specifically Bind TNBC Cells

Figure 4A:
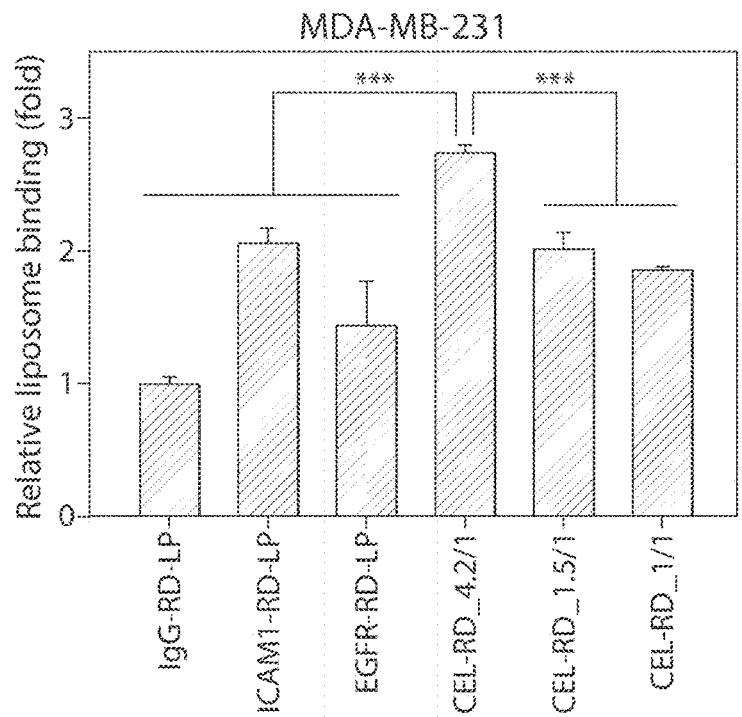
FIGS. 4A-4C show TNBC-specific binding of CEL-RDs at different antibody ratios in MDA-MB-231 (FIG. 4A), MDA-MB-436 (FIG. 4B), and MCF10A cells (FIG. 4C) by flow cytometry analysis.
Figure 4B:
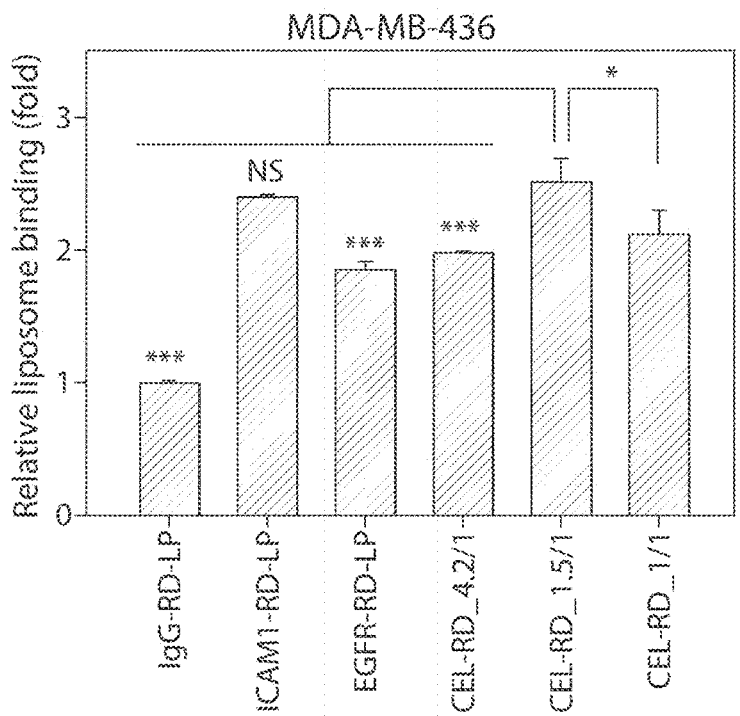
Figure 4C:
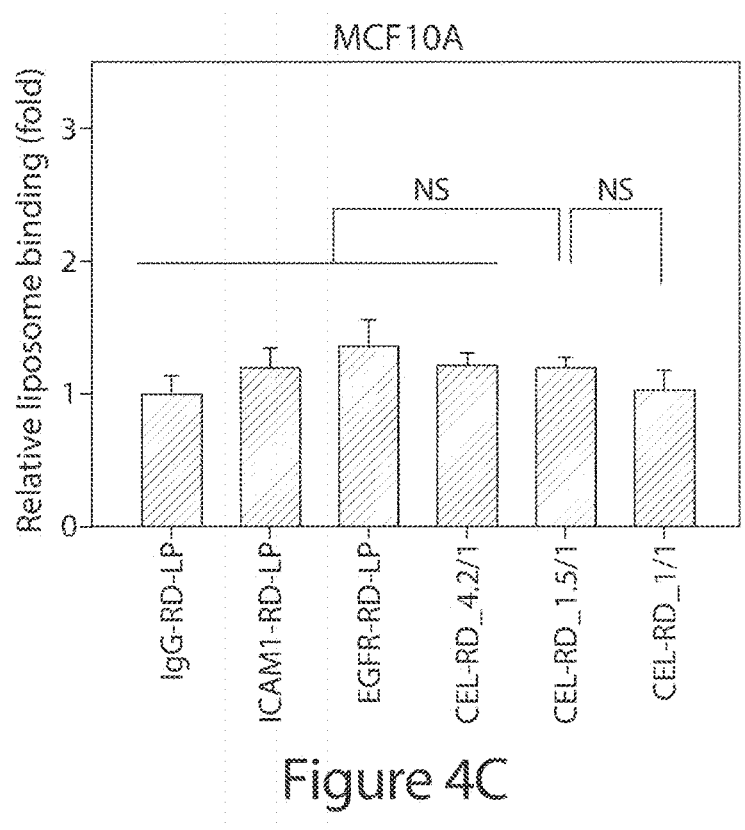
Figure 6A:
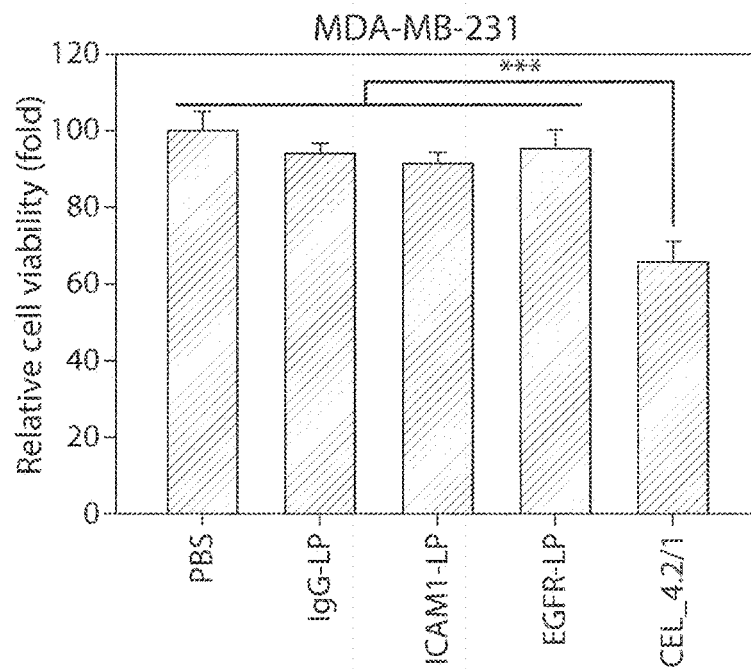
FIGS. 6A-6B demonstrate that EGFR antibody presented on CELs serves as both targeting ligand and pharmaceutically compositions for inhibiting TNBC cell proliferation measured by Dojindo assay. Cellular proliferation of TNBC cells treated with PBS (control), non-specific IgG-LP, ICAM-1-LP, EGFR-LP, and CELs at optimal ICAM-1/EGFR antibody ratios (4.2/1 for MDA-MB-231 cells (FIG. 6A), and 1.5/1 for MDA-MB-436 cells (FIG. 6B)).
Figure 6B:
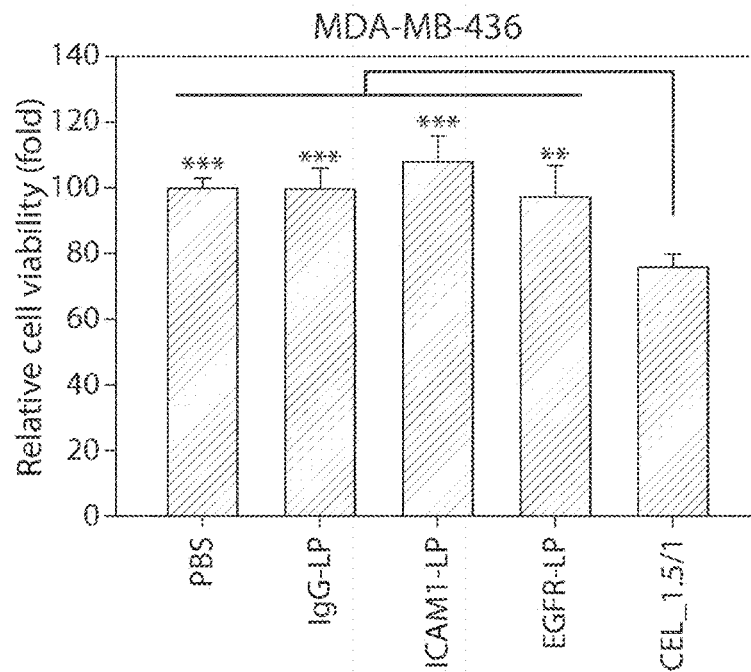

The dual-targeting of CELs to TNBC cells was assessed via flow cytometry analysis. Because Dox is highly cytotoxic to TNBC cells, it was replaced with a non-toxic, fluorescent molecule, rhodamine-dextran (RD, 10 kDa). Binding of RD encapsulating CELs at different antibody ratios was compared to single antibody and IgG controls. As shown in FIG. 4, CELs with the ICAM-1:EGFR antibody ratio of 4.2/1 (CEL_4.2:1) complemented the surface protein expression of MDA-MB-231 cells and exhibited the highest liposome binding with MDA-MB-231 cells compared with EGFR Antibodies on CEL Inhibit TNBC Cell Proliferation EGFR is known for its role in promoting tumor growth. Small molecular inhibitors of EGFR (Erlotinib and Afatinib) are approved by the U.S. FDA to treat a number of solid tumors, including lung and pancreatic cancers. Thus, the inhibitory role of EGFR antibodies conjugated on CELs on proliferation was also evaluated. As shown in FIG. 6, human TNBC cells were incubated with IgG-LP, ICAM-LP, EGFR-LP and CELs. Surprisingly, CELs at optimal ICAM-1:EGFR antibody ratios demonstrated a significantly lower TNBC cell proliferation than other liposomes, even lower than EGFR-LPs in two TNBC cell lines. This may indicate that simultaneous blocking of ICAM-1 and EGFR on TNBCs may synergistically inhibit TNBC proliferation. Although the antibody blockade of CELs is not as powerful as the CEL-Dox combination, it may contribute to TNBC cell cytotoxicity.

TNBC-Specific Dox Delivery by CEL-Dox

Figure 7A:
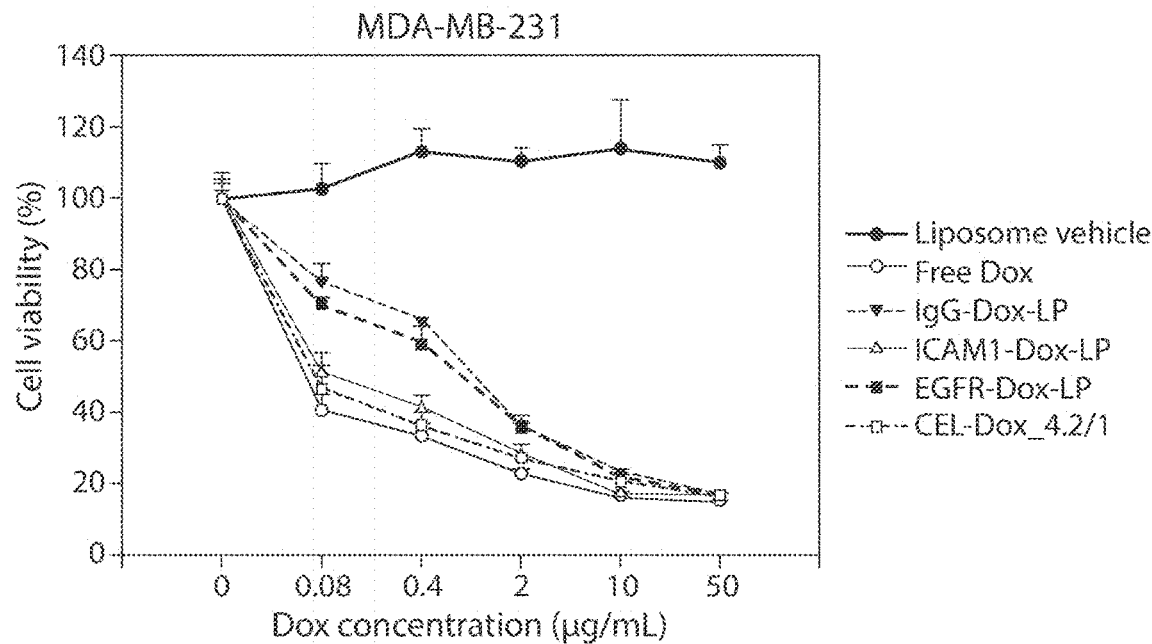
FIGS. 7A-7B shows the cytotoxicity of CEL-Dox at optimal ICAM-1/EGFR antibody ratios was evaluated for MDA-MB-231 (FIG. 7A) and MDA-MB-436 (FIG. 7B) cells by Dojindo cell viability assay.
Figure 7B:
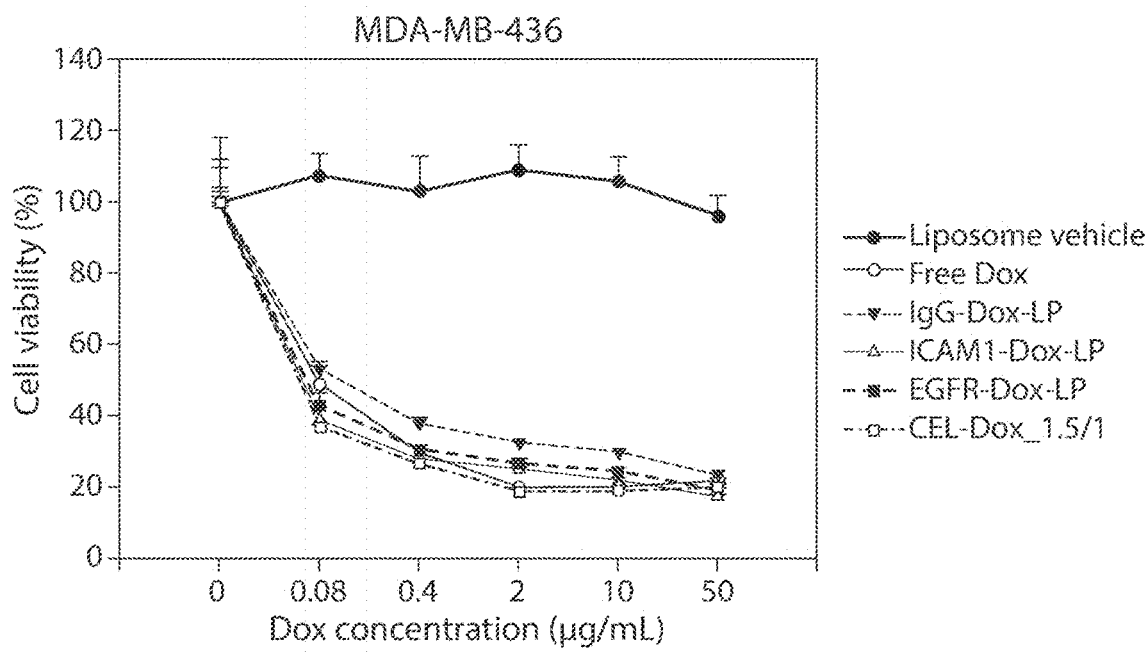

The cytotoxicity of CEL-Dox was evaluated by measuring TNBC cell proliferation. A dose-dependent cytotoxicity study was performed for MDA-MB-231 and MDA-MB-436 cells. As seen in FIGS. 7A and 7B, ICAM-1 or EGFR single-targeting liposomes, and CELs showed superior cytotoxicity over non-specific IgG-Dox-LP in both TNBC cell lines. Liposome vehicles without Dox and antibodies do not induce any significant cytotoxicity in TNBC cells, indicating the liposome itself is not cytotoxic. The half maximal inhibitory concentrations (IC50s) for free Dox, IgG-Dox-LP, ICAM-1-Dox-LP, EGFR-Dox-LP, and CEL-Dox (4.2:1 for MDA-MB-231, and 1.5:1 for MDA-MB-436) were calculated as 0.12, 1.22, 0.14, 0.92, and 0.05 µg/mL for MDA-MB-231 and 35.5, 41.1, 11.5, 19.3, and 7.0 ng/mL for MDA-MB-436, respectively. Thus, CEL-Dox effectively killed TNBC cells via enhanced delivery of Dox to TNBC cells. This was achieved via the specific adhesion and inhibitory action between proteins expressed on the TNBC cell membrane and ICAM-1 and EGFR antibodies conjugated to CELs at optimal ratios.

In Vivo Tumor Accumulation and Efficacy of ICAM-1 Targeted Immunoliposomes

Figure 8A:
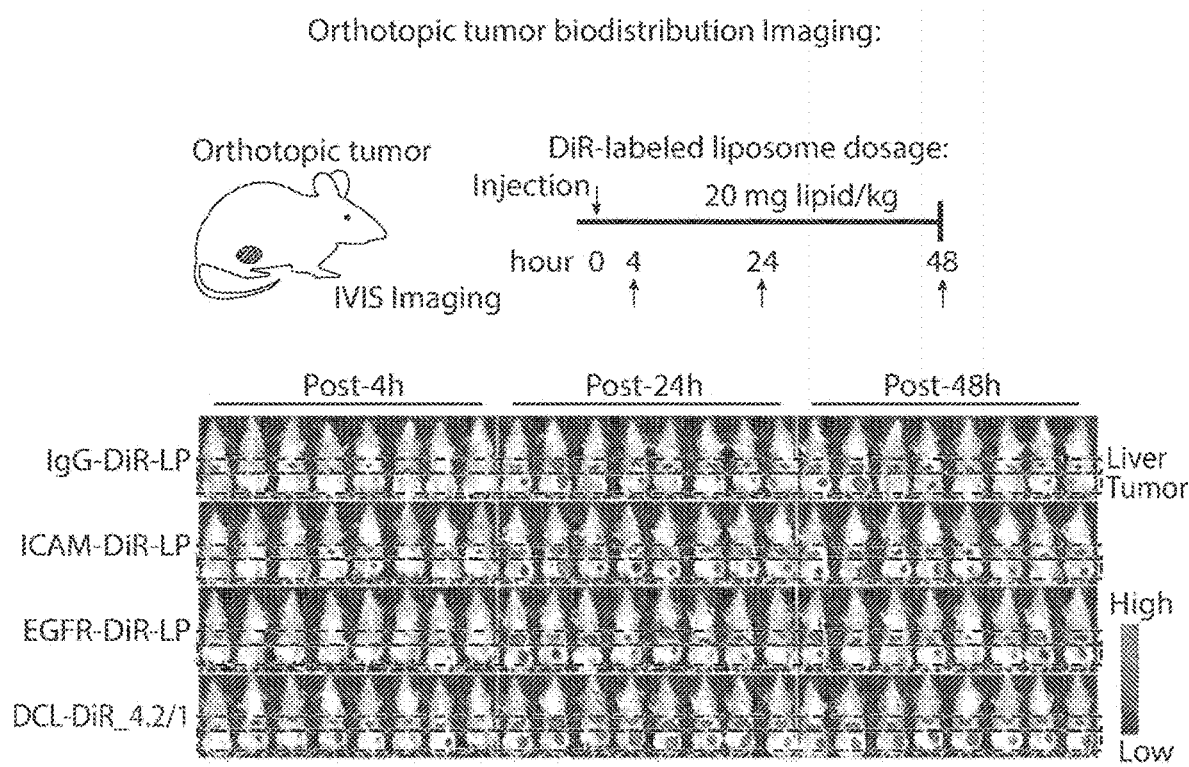
FIGS. 8A-8F show an in vivo evaluation of TNBC specificity of ICAM-1/EGFR dual-targeting CEL in comparison with non-specific IgG and ICAM-1/EGFR single-targeting liposomes.
Figure 8B:
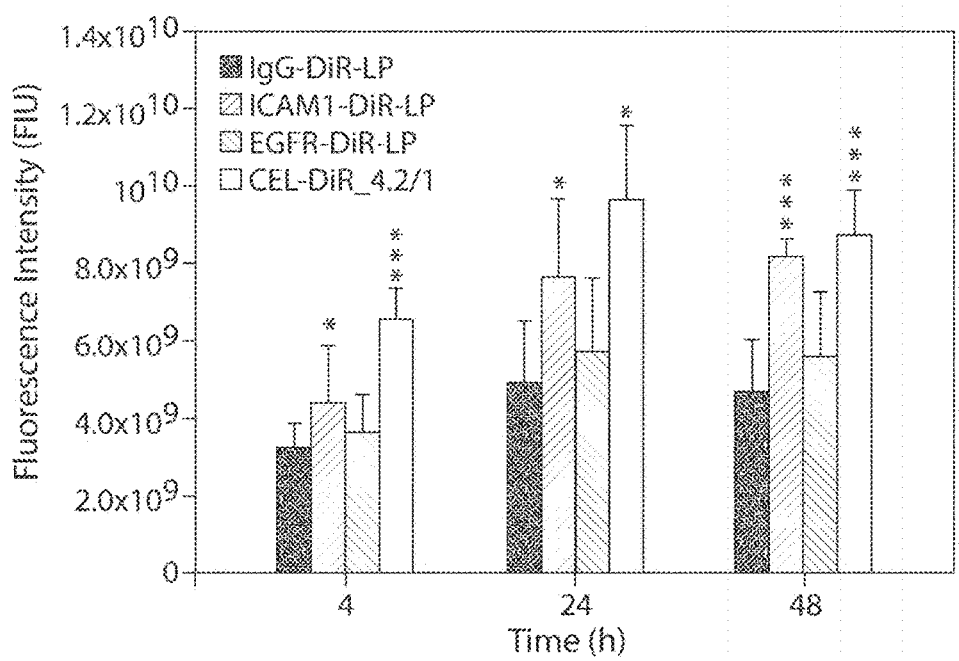
Figure 8C:
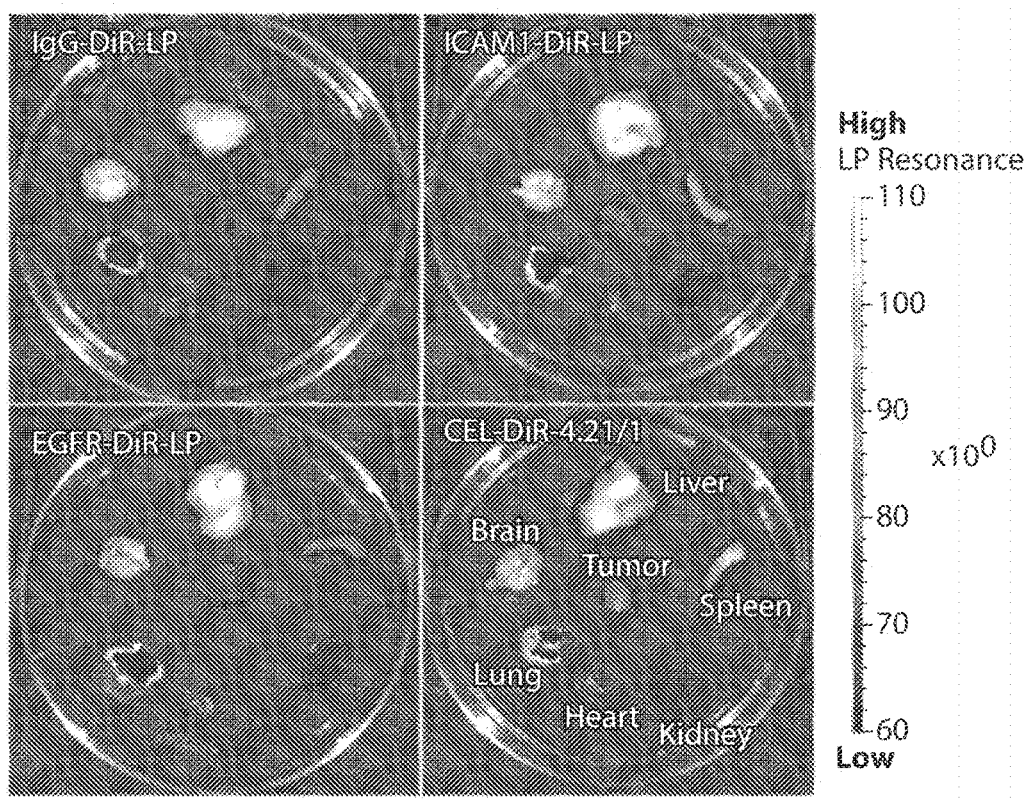
Figure 8D:
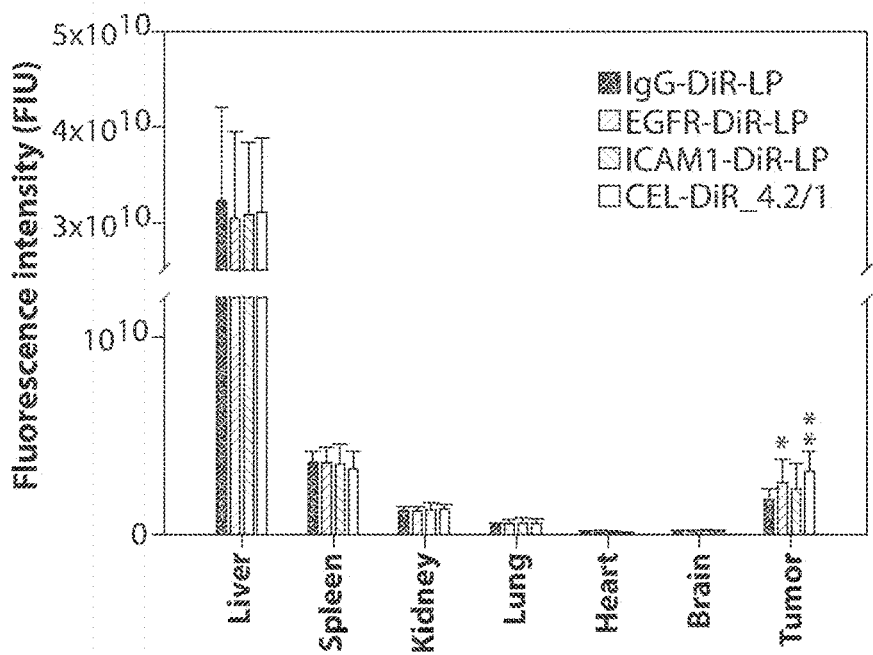

To determine if the specific affinity of CEL on TNBC cells can result liposomes (~100 nm in diameter) in tumor accumulation in vivo, the distribution of ICAM-1/EGFR targeted immunoliposomes was examined by near-infrared (NIR) fluorescent imaging in a mouse breast cancer model. MDA-MB-231 cells were orthotopically implanted in immunodeficient nude mice. Near-infrared fluorescent imaging was performed on four groups of tumor-bearing mice injected with (1) IgG conjugated immunoliposomes labeled with a NIR dye DiR (IgG-DiR-LPs), (2) ICAM-1 antibody conjugated immunoliposomes labeled with DiR (ICAM-DiR-LPs), (3) EGFR antibody conjugated immunoliposomes labeled with DiR (ICAM-DiR-LPs), and CEL labeled with DiR (CEL-DiR_4.2/1). Each group was scanned at 4, 24, and 48 hours post injection. The representative images in FIG. 8A show that CEL-DiR_4.2/1 were significantly increased at TNBC tumor sites relative to non-specific IgG-DiR-LPs, which exhibited an approximately 2-fold increase in fluorescence compared to IgG-DiR-LPs, suggesting that CEL-DiR_4.2/1 significantly improved TNBC tumor accumulation by actively targeting the TNBC tumor via ICAM-1 binding (FIG. 8B). The biodistribution of CEL-DiR_4.2/1 were evaluated by quantifying ex vivo NIR fluorescent signals in collected organs and tumors. FIGS. 8C and 8D show comparative immunoliposome accumulation in six normal organs (liver, spleen, lung, kidney, brain, and heart) and one TNBC tumor harvested from mice at 48 hours after a single tail vein administration. Correlating with the in vivo imaging results, the immunoliposome accumulation of CEL-DiR_4.2/1 in TNBC tumors is approximately 2-fold higher than that of IgG-DiR-LPs. For six normal organs, there was no significant difference observed between ICAM-DiR-LP and EGFR-DiR-LP groups.

Figure 9C:
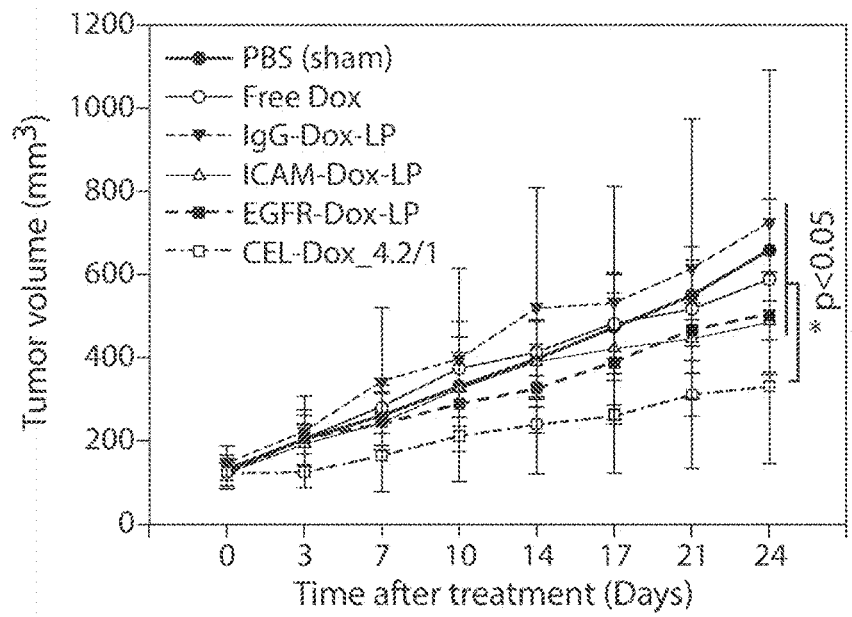
Figure 9D:
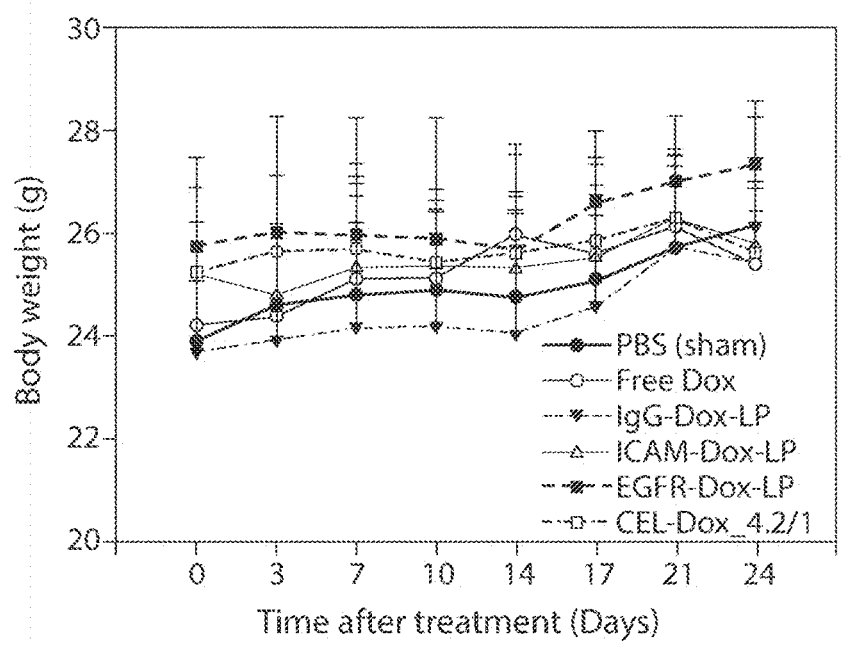

Whether CEL-DiR_4.2/1 was able to convert its in vivo TNBC tumor-targeting activity into improved therapeutic efficacy was also examined. ICAM-1/EGFR-targeted, doxorubicin-encapsulating immunoliposomes (CEL-Dox_4.2/1) were engineered and injected i.v. to nude mice bearing orthotopic TNBC tumors (MDA-MB-231 cells). PBS and non-targeted IgG-Dox-LPs were also tested as controls. After a 24-day treatment regimen, the administration of CEL-Dox_4.2/1 efficiently inhibited TNBC tumor growth in comparison with PBS and IgG-Dox-LPs (FIG. 9A). Quantified tumor mass results (FIG. 9B) further reveal that CEL-Dox_4.2/1 could significantly inhibit TNBC tumor growth by over 70% relative to control groups (PBS). All groups of mice maintained their body weight without significant loss during these treatment periods (FIG. 9C). TNBC tumor sections were stained with hematoxylin and eosin (H&E) and ICAM-1 antibody; histological staining (FIG. 9D) also confirmed that there is a high expression level of ICAM-1 present in TNBC tumors. These results indicate that ICAM-Dox-LPs can inhibit in vivo growth of ICAM-1-overexpressing TNBC tumors via ICAM-1 antibody-mediated TNBC tumor recognition and targeting in vivo.

Discussion

A key challenge in the development of cancer (e.g., TNBC)-targeted therapeutics is how to discriminate cancer cells from non-neoplastic cells. The recognition of cancer cells primarily relies on the identification of molecular targets that are overexpressed on cancer (e.g., TNBC) cells with minimum or no expression on non-neoplastic cells. Several TNBC molecular targets, such as EGFR, ICAM-1, CD44, and transferrin receptor, have been examined as nanomedicine targeting moieties for TNBC treatment. However, their clinical application is limited by their tumor specificity relative to normal tissue. These critical issues can be addressed by exploiting novel TNBC-specific molecular targets and associated targeting strategies.

In this study, a dual-ligand targeting strategy that functions by complementing the molecular density and organization of proteins overexpressed exclusively on TNBC cell membranes was developed. The overexpression levels of 12 potential TNBC molecular targets were quantitatively characterized, and ICAM-1 and EGFR were identified as a TNBC dual-targeting combination according to the following criteria: (1) overexpression level, both ICAM-1 and EGFR have been found highly overexpressed on TNBC cells at both surface protein (FIG. 1) and mRNA (FIGS. 2B and 2C) levels; (2) TNBC specificity, according to the Human Protein Atlas Database (www.proteinatlas.org), ICAM-1 and EGFR protein expression were detected in 14 and 22 out of over 80 normal tissue cell types, which are similar or less than other existing TNBC targets such as Integrin αvβ3 and CD44; and (3) accessibility. ICAM-1 and EGFR were confirmed to be colocalized on both MDA-MB-231 and MDA-MB-436 cell membranes using immunofluorescent imaging (FIG. 2A), suggesting that they can be recognized and bound by multivalent liposomes. Therefore, the unique ratio of ICAM-1 and EGFR surface densities on TNBC cells was defined as their "fingerprint" combination for dual-ligand targeting.

ICAM-1 is a cell membrane glycoprotein that participates in cell trafficking, adhesion, and inflammation. It acts as a receptor for leukocyte function associated antigen-1 (LFA-1) present on the surface of T-lymphocytes, lymphokine-activated killer cells, and nature killer cells. ICAM-1 is implicated in the metastasis of several advanced cancers, including human TNBC tumors. ICAM-1 levels in tumor tissues and serum have been found to strongly correlate with the risk of metastasis, indicating ICAM-1 has an important role in tumor metastasis. EGFR is a cell surface receptor for epidermal growth factor (EGF) that is upregulated in a variety of tumor cells, including breast cancer. EGFR is widely used as a target for the development of nanomedicine with specific affinity. In 2009, Acharya et al. reported that anti-EGFR antibody-conjugated, Rapamycin encapsulating poly(lactic-co-glycolic acid) nanoparticles can efficiently deliver anticancer drugs specifically to breast cancer cells and inhibit breast cancer cell proliferation.

Dox-encapsulating CELs target TNBC cells by using ICAM-1 and EGFR overexpression as a "fingerprint" to facilitate TNBC-specific Dox delivery. The CELs of the present disclosure achieved over 2.3-fold higher TNBC binding compared with non-specific IgG conjugated liposomes, which is significantly more precise than ICAM-1 or EGFR single-targeting liposomes and CELs at non-optimal antibody ratios. The increased TNBC specificity is attributed to the cooperative adhesion of ICAM-1 and EGFR antibodies on CELs. When antibodies on CELs interact with their binding partner, they form a complex in which the collective binding is a product of multiple discrete interactions. The local molecular density of target proteins at the liposome-cell membrane contact interface is increased. Once the first binding contact is made, subsequent interactions become more favorable due to the complementary nature of CELs. CELs, at an optimal antibody ratio, reorganize their binding sites for TNBC cells. The formation of multiple interactions with cooperatively increases the enthalpic stability of each interaction. Thus, dual-targeting can yield an overall strong adhesion, which is unique in tumor targeting therapeutics. It was also noted that the antibodies conjugated on CELs are not only targeting ligands, but also function as effective inhibitors of TNBC cell invasion and proliferation by blocking the ICAM-1 and EGFR signaling cascades.

Conclusion

The collective studies demonstrate that dual-targeting is a highly precise and effective strategy for TNBC targeted therapy. It was also found that ICAM-1 and EGFR antibodies conjugated to CELs, did, in fact, synergistically inhibit TNBC cell proliferation and invasion. Given the long-standing interest in identifying and evaluating cancer targets and biomarkers for nanomedicine, it is believed that the complementary dual-targeting method can be extended to other nanoscale drug delivery systems including solid lipid nanoparticles, polymeric nanoparticles, and antibody drug conjugates.

Experimental Methods

Materials

Dulbecco's phosphate buffered saline (PBS), 4',6-diamidino-2-phenylindole (DAPI), 0.25% trypsin/2.6 mM ethylenediaminetetraacetic acid (EDTA) solution, Gibco® Dulbecco's Modified Eagle Medium (DMEM), and Gibco®DMEM/F12(1:1) were purchased from Invitrogen (Carlsbad, Calif., USA). Quantum Simply Cellular microbeads were purchased from Bangs Laboratory (Fishers, Ind., USA). Mouse anti-human ICAM-1 monoclonal antibody, mouse anti-human EGFR monoclonal antibody, immunoglobulin G (IgG) isotype control were purchased from R&D Systems (Minneapolis, Minn., USA). Fluorescein isothiocyanate (FITC) or Phycoerythrin (PE)-conjugated mouse/rat anti-human antibodies against 12 proteins (CXCR4, CCR2, CCR5, CCR7, ICAM-1, VCAM-1, E-Cadherin, N-Cadherin, EGFR, HER2, CD44, and CD24), FITC and PE-conjugated mouse/rat IgG isotype were purchased from BioLegend (San Diego, Calif., USA). 1-Ethyl-3-(3-dimethylaminopropyl) carbodiimide hydrochloride (EDC), N-hydroxysuccinimide (NHS), bovine serum albumin (BSA), anhydrous dimethyl sulfoxide (DMSO) were purchased from Sigma-Aldrich (St. Louis, Mo., USA). Matrigel coated cell invasion chambers and Lab-Tek II Chamber Slide System were obtained from Thermo Fisher Scientific (Pittsburgh, Pa., USA). Fluorogel with tris buffer was purchased from Electron Microscopy Sciences (Hatfield, Pa., USA). Activation Buffer and Coupling Buffer were purchased from Ocean Nanotech (Springdale, Ark., USA).

Cell Culture

Two human TNBC cell lines (MDA-MB-231 and MDA-MB-436) and one human non-neoplastic mammary epithelial cell line (MCF10A) were used in the presented study. All three cell lines are available through American Type Culture Collection (ATCC, Manassas, Va., USA). MDA-MB-231 and MDA-MB-436 cells were cultured in DMEM, MCF10A in DMEM/F12 (1:1) Medium, with all recommended supplements, respectively. All cells were maintained at 37° C. in a humidified incubator with 5% $CO_2$.

Quantification of Cell Membrane Protein Expression

The cell membrane expressions of 12 potential target proteins (CXCR4, CCR2, CCR5, CCR7, ICAM-1, VCAM-1, E-Cadherin, N-Cadherin, EGFR, HER2, CD44, and CD24) were evaluated by a BD FACSCalibur Flow Cytometer (BD Biosciences, San Jose, Calif., USA) as described previously. Quantification of the ICAM-1 density on the cell surface was determined with reference to Quantum Simply Cellular microbeads, using the protocol as provided by the manufacturer. Briefly, $10^6$ cells were collected and rinsed twice through suspension-spin cycles. Cells were blocked by 1% bovine serum albumin (BSA) in PBS for 30 min in an ice bath. After BSA blockage, cells were incubated with PE-conjugated antibodies against CXCR4, CCR2, CCR5, CCR7, ICAM-1, VCAM-1, E-Cadherin, N-Cadherin, EGFR, HER2, CD44, and CD24, separately for 1 hour at RT. Cells were rinsed with 1% BSA in PBS three times, resuspended in PBS, and evaluated by flow cytometry.

Immunofluorescent Staining of Dual-Targeting Proteins

MDA-MB-231, MDA-MB-436, and MCF10A ($2\times10^5$ cells) were seeded in a Lab-Tek II Chamber Slide System separately with 2 mL media overnight at 37° C. After media was removed, cells were rinsed with PBS three times and fixed with 4% formaldehyde in PBS at RT for 10 min, and followed by washing with PBS. Samples were blocked with 1% BSA in PBS for 30 min in an ice bath. After BSA blocking, samples were co-stained with FITC-conjugated ICAM-1 antibody and PE-conjugated EGFR antibody for 1 hour and rinsed with PBS. DAPI was used to stain the cell nucleus. Immunofluorescent stained samples were dried overnight in the dark and used for fluorescent microscope imaging. Samples were examined under a Leica TCS SP5 confocal fluorescent microscope (Leica Microsystems, Buffalo Grove, Ill., USA). Digital images were captured with AxioVision digital image processing software.

Quantification of Gene Expression

The gene expression levels of ICAM-1 and EGFR in TNBC cells were characterized using qRT-PCR. MDA-MB-231, MDA-MB-436, and MCF10A cells were cultured at $3\times10^5$ cells/well in 6-well cell culture plate overnight. Cells were then removed from each well by incubating with a trypsin/EDTA solution for 3 min. The cells were washed with PBS for three times. RNA was extracted, purified using the Qiagen RNeasy minikit, and quantified using a SpectraMaxPlus 384 UV-Visible Spectrophotometer (Molecular Devices Corp, Sunnyvale, Calif., USA). Reverse transcription was conducted using the Applied Biosystems Taqman RT protocol. Detection and quantification of mRNA was performed by the StepOnePlus Real-Time PCR System (Applied Biosystems, Carlsbad, Calif., USA). All PCR samples were referenced to the gene expression of Glyceraldehyde 3-phosphate dehydrogenase (GAPDH).

Preparation of CEL-Dox

The Dox-encapsulating CEL (CEL-Dox) was prepared by the transmembrane gradient assay as described previously. Briefly, a lipid formulation consisting of DOPC:DSPE-PEG-COOH (95:5, mol:mol) was used to prepare liposomes. 50 mmol lipid mixture was solubilized in chloroform and dried under a dry nitrogen stream. The resulting lipid film was dissolved in 1 mL DMSO:EtOH (7:3, v:v). The lipid solution was injected in 9 mL of 240 mM sodium sulfate in phosphate buffered saline (PBS, pH 7.4) while being rigorously agitated to yield a 5 mM lipid solution. After 10 freeze-thaw cycles, lipid solution was extruded via a NorthernLipids Extruder with a 100 nm polycarbonate nanoporous membrane. After extrusion, the liposome solution was dialyzed in PBS (pH 7.4) using a Slide-A-Lyzer dialysis cassette (MWCO 20 kDa) overnight at room temperature (RT). Then Dox was added to liposome solution to reach a final concentration of 200 µg/mL, and incubated for 6 h to facilitate active loading. The resulting Dox-encapsulating liposome solution was dialyzed in PBS (pH 7.4) using a Slide-A-Lyzer dialysis cassette (MWCO 20 kDa) overnight at RT.

The surface of Dox-encapsulating liposomes was modified with the antibodies against TNBC dual-targeting proteins (ICAM-1 and EGFR) at optimal ratios via the DSPE-PEG-COOH anchor. EDC (2 mg) and NHS (3 mg) were mixed with 1 mmol of lipid (liposomes) in PBS (pH 7.4) and incubated for 6 hours at RT. A Slide-A-Lyzer dialysis cassette (MWCO 10 kDa) was used to remove unreacted EDC and NHS. Next, ICAM-1 and EGFR antibodies at different molecular ratios (1/0, 0/1, 1/1, 4.2/1, and 1.5/1) or the IgG isotype was added to EDC-modified liposomes at a molar ratio of 1:1000 (antibody:phospholipid) and incubated overnight at RT. Unreacted antibodies were removed by using a FLOAT-A-LYZER G2 dialysis tubing (MWCO 300 kDa). In liposome binding experiments, non-cytotoxic rhodamine-dextran encapsulating liposomes (CEL-RDs) were prepared and tested to replace the cytotoxic CEL-Dox. The preparation process was similar as CEL-Dox with the exception being that the 1 mL lipid solution was added to a 9 mL rhodamine-dextran solution (1 mg/mL).

The density of ICAM-1 and EGFR antibodies conjugated on liposomes was quantified via microbead assay as described previously. Liposomes cannot be detected by flow cytometry because of their size, therefore, 2 µm borosilicate beads were encapsulated within DOPC:DSPE-PEG-COOH (95:5, mol:mol) liposomes by sonicating small unilamellar liposomes with microbeads in PBS for 6 h. Microbeads were rinsed three times in PBS via suspension-spin cycles to separate free liposomes. Conjugation of FITC-ICAM-1 antibody, PE-EGFR antibody or PE-IgG (nonspecific binding) to microbead encapsulating liposomes was performed using EDC/NHS chemistry. The surface densities and ratios of ICAM-1 and EGFR antibody conjugated to each microbead was determined with reference to Quantum Simply Cellular microbeads, which have defined numbers of antibody binding sites per bead. Liposome size and zeta potential were measured by dynamic light scattering on a Zeta-PALS analyzer (Brookhaven Instruments, Holtsville, N.Y.) in PBS (pH 7.4).

TNBC Cellular Binding of CELs

Quantitative analysis of liposome binding to TNBC cells was studied by flow cytometry analysis. $10^6$ cells were placed in each well of a 6-well cell culture plate and incubated for 4 hours at 37° C. with (1) rhodamine-dextran (RD)-encapsulating, nonspecific IgG conjugated liposome (IgG-RD-LP), (2) RD-encapsulating ICAM-1 antibody conjugated liposome (ICAM-RD-LP), (3) RD-encapsulating EGFR antibody conjugated liposome (EGFR-RD-LP), (4) RD-encapsulating CEL at ICAM-1/EGFR antibody ratio of 4.2/1 (CEL-RD_4.2/1), (5) RD-encapsulating CEL at ICAM-1/EGFR antibody ratio of 1.5/1 (CEL-RD_1.5/1), and (6) RD-encapsulating CEL at ICAM-1/EGFR antibody ratio of 1/1 (CEL-RD_1/1) at a final concentration of 1 µM lipids per $10^6$ cells. All liposome-treated cells were washed with PBS, harvested using a 0.25% trypsin/2.6 mM EDTA solution, and washed with PBS (pH 7.4) three times. Binding data were acquired using a BD FACSCalibur flow cytometer and analyzed using FlowJo software. The specific cell uptake of CELs at different ratios with reference to non-specific IgG-RD-LPs was calculated by dividing the mean fluorescence intensity of CEL-RD stained cells by that of the IgG-RD-LP stained cells.

TNBC Cell Invasion

Human TNBC cells (MDA-MB-231 and MDA-MB-436, $10^5$ cell per well) were pre-treated with following samples: (1) PBS, (2) IgG-LP, (3) ICAM-LP, (4) EGFR-LP, (5) CELs at optimal ICAM-1/EGFR antibody ratios (4.2/1 for MDA-MB-231 cells, and 1.5/1 for MDA-MB-436 cells) at the final liposome concentration of 1 µM lipids per $10^6$ cells for 24 h, and then seeded onto COSTAR matrigel coated invasion inserts with permeable support polycarbonate membrane and an 8 µm pore size in a 24-well plate at a cell density of $10^5$ cell per well. DMEM without fetal bovine serum (FBS) and DMEM with 10% FBS were added to the upper and lower wells, respectively. The cells were incubated and allowed to invade for 20 hours. The cells on the reverse side of transwell membrane facing the lower chamber after transmigrating through the 8-µm pores of transwell membrane were stained with Diff-Quik Stain Set. Four fields were counted for each sample.

TNBC Cell Proliferation $5\times10^3$ human TNBC cells (MDA-MB-231 or MDA-MB-436) were plated in each well of a 96-well plate and treated for 48 h with CM harvested from MDA-MB-231 treated with (1) PBS, (2) IgG-LP, (3) ICAM-LP, (4) EGFR-LP, (5) CELs at optimal ICAM-1/EGFR antibody ratios (4.2/1 for MDA-MB-231 cells, and 1.5/1 for MDA-MB-436 cells) at the final liposome concentration of 1 µM lipids per $10^6$ cells for 48 hours. The human TNBC cell proliferation was analyzed using a Dojindo cell counting kit using the protocol from the Dojindo Molecular Technologies (Rockville, Md., USA).

CEL-Dox Cytotoxicity

The cytotoxicity of CEL-Dox on TNBC cells were evaluated using a cell viability assay. $5\times10^3$ cells (MDA-MB-231 and MDA-MB-436) were seeded in each well of a 96 well plate and incubated for 24 h. Cells were treated with (1) PBS, (2) Free Dox, (3) non-specific IgG-conjugated, Dox-encapsulating liposomes (IgG-Dox-LPs), (4) ICAM-1 antibody-conjugated, Dox-encapsulating liposomes (ICAM-1-Dox-LP), (5) EGFR antibody-conjugated, Dox-encapsulating liposomes (EGFR-Dox-LP), and (6) Dox-encapsulating CELs at optimal ICAM-1/EGFR antibody ratios (4.2/1 for MDA-MB-231 cells, and 1.5/1 for MDA-MB-436 cells) at the final liposome concentration of 1 µM lipids per $10^6$ cells for 6 hours. Cells were rinsed three times with PBS and grown for 48 hours. Cell viability was determined by a Dojindo cell counting kit using the protocol from the manufacturer (Rockville, Md.).

Orthotopic TNBC Mouse Models and Treatments

Animal experiments were performed according to the protocols approved by the Institutional Animal Care and Use Committees of City College of New York, Boston Children's Hospital and Harvard Medical School. Breast tumors were orthotopically planted by injecting $5\times10^6$ MDA-MB-231 cells into the fourth mammary fat pad of female nude mice (Charles River). Mice were randomized into the various tested groups (n=8-10 for each group). For in vivo fluorescent imaging experiments, tumors were developed for 5-7 weeks until they were at least 1 cm$^3$ in volume. In vivo fluorescent imaging was performed on the tumor bearing mice in four groups, which were injected i.v. with different immunoliposome formulations (at dosage of 20 mg lipids/kg mouse weight), respectively. At 4, 24, and 48 hours after the injection, in vivo fluorescence imaging was performed with an IVIS Spectrum system (Caliper, Hopkington, Mass.). At 48 hours post injection, the mice were sacrificed after heart perfusion with saline and 4% paraformaldehyde. The fluorescence intensity of various organs (brain, heart, liver, lung, kidney, spleen, and tumor) was measured by IVIS system. For in vivo therapeutic efficacy experiments, tumors were developed for 1-2 weeks until they reached 100 mm$^3$ in volume. Then each group of mice started treatment by administrating PBS (sham), IgG-Dox-LP, ICAM-Dox-LP, EGFR-Dox-LP, and CEL-Dox_4.2/1 (2.5 mg/kg per dosage, twice a week). All injection for treatments was performed intravenously (retro orbital) in 50 µL PBS. 24 days after treatment, orthotopic tumors were excised to measure their mass.

Statistical Analysis

All of the experimental data were obtained in triplicate unless otherwise mentioned and are presented as mean±standard deviation. Statistical comparison by analysis of variance was performed at a significance level of $p<0.05$ based on a Student's t-test.

Example 2 Dual Complementary Liposome (DCL)

Triple negative breast cancer (TNBC) is a heterogeneous disease, defined by the lack of estrogen receptor (ER), progesterone receptor (PR), and human epidermal growth factor receptor type 2 (HER2). TNBC, which represents 15-20% of all breast cancers, occurs more frequently in women under 50 years of age, in African American women, and in individuals carrying a breast cancer early onset 1 (BRCA1) gene mutation. Due to the lack of therapeutic targets and limited treatment options, the prognosis for TNBC patients remains the poorest among all breast cancer patients.

Nanotherapeutics were developed to improve the safety and efficacy of anti-tumor drugs, which bring measurable clinical benefits to the treatment of several metastatic cancers. However, none of the clinically used nanotherapeutics (e.g., Onivyde and Abraxane) are tumor-specific. Importantly, these drugs depend solely on the enhanced permeability and retention (EPR) effect to enter the tumor, which can be severely hindered by tumor complexity and heterogeneity. To overcome this obstacle, "next-generation" nanotherapeutics (e.g., MM302) utilize tumor-targeting ligands to improve their tumor accumulation. Unfortunately these therapeutics failed to meet therapeutic expectations in clinical trials due to their limited targeting activity and significant "off-target" effects. Recent extensive studies of extracellular vesicles (e.g., exosomes) have shed light on the biomechanisms of naturally occurring drug delivery nanocarriers. For instance, tumor-derived exosomes utilize multivalent ligand-receptor interactions between vesicles and targeted cells to mediate intercellular communication. These exosomes deliver secreted proteins, mRNAs and DNAs substantially more efficiently than their synthetic counterparts. Cells employ a complex array of molecular interactions to deliver molecules that in turn govern cell functions.

Described herein is a complementary targeting strategy that imparts precisely matched, multivalent ligand-receptor interactions to efficiently recognize and target TNBC tumors and metastases. Unlike conventional targeted drug delivery systems that present a single ligand, the surface of a liposome was functionalized to precisely complement the molecular ratio and organization of multiple cancer receptors overexpressed on TNBC cell membranes. It is believed that this precisely matched, multivalent ligand-receptor interaction between complementary targeting drug delivery systems and TNBC cells would increase cellular adhesion and accumulation at TNBC tumors and metastases in vivo, which, in turn, would improve the therapeutic efficacy of nanotherapeutics.

To test this, an unbiased and quantitative screening approach was developed to select optimal targets for complementary targeting. Based on the screening data, a proof-of-principle, dual complementary liposome (DCL) composed of antibodies against ICAM1 and EGFR, which are molecular targets of FDA-approved drugs, and liposomal doxorubicin, a clinically used breast cancer nanotherapeutic, was then engineered. In vitro mechanistic studies further revealed that DCLs exhibited three major advantages over conventional "single" and "dual-targeting" liposomes: (1) cellular binding was significantly increased via precisely matched, multivalent ligand-receptor interactions, (2) internalization was enhanced via cooperative endocytosis pathways, and (3) therapeutic efficacy was improved via simultaneous blockade of ICAM1 and EGFR pathways. Finally, using in vivo orthotopic tumor and lung metastasis models, it was demonstrated that the potent tumor-targeting and anti-tumor activities of DCLs can be effectively translated into therapeutic and survival benefits by inhibiting TNBC tumor progression and metastasis. Taken together, these data demonstrate that complementary targeting is a promising and translational platform for the design of tumor-targeting nanomedicines.

Selection of TNBC Targets for Complementary Targeting

Figure 10A:
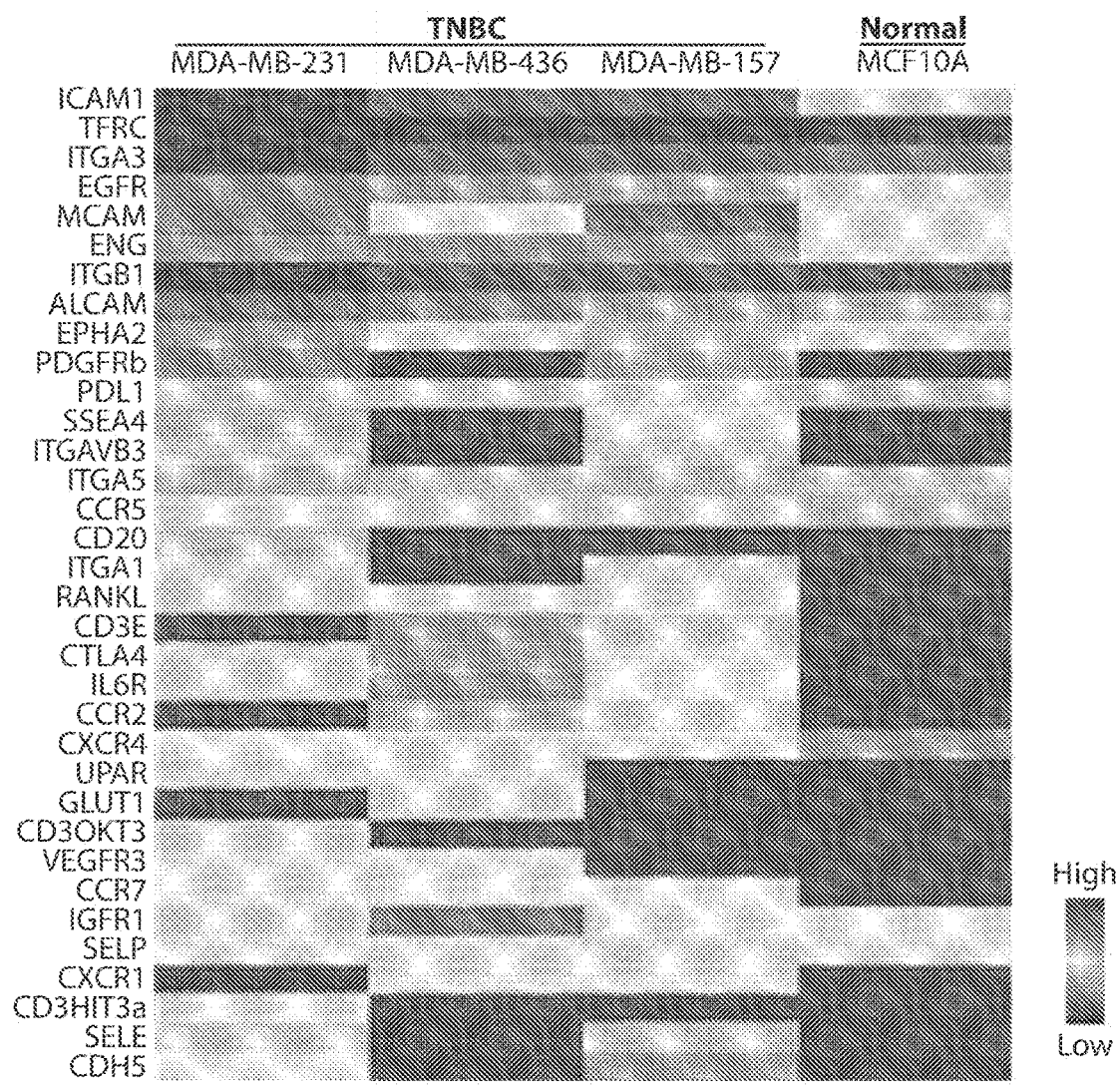
FIGS. 10A-10G show the identification of ICAM1 and EGFR as candidates for TNBC complementary targeting.
Figure 10A:
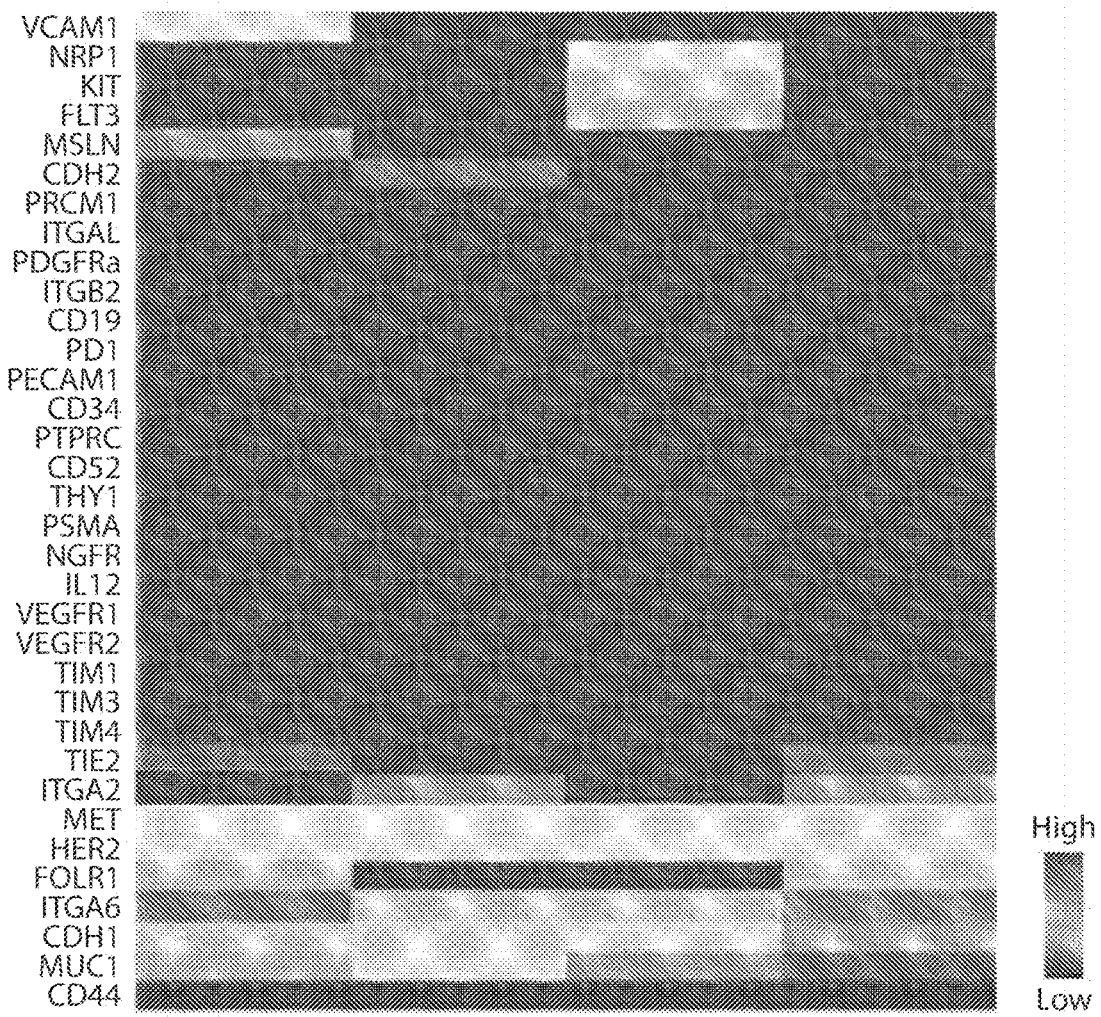
Figure 10B:
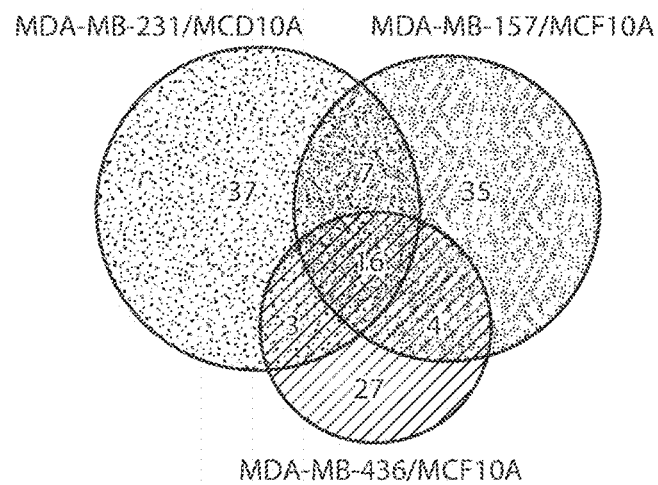
Figure 10C:
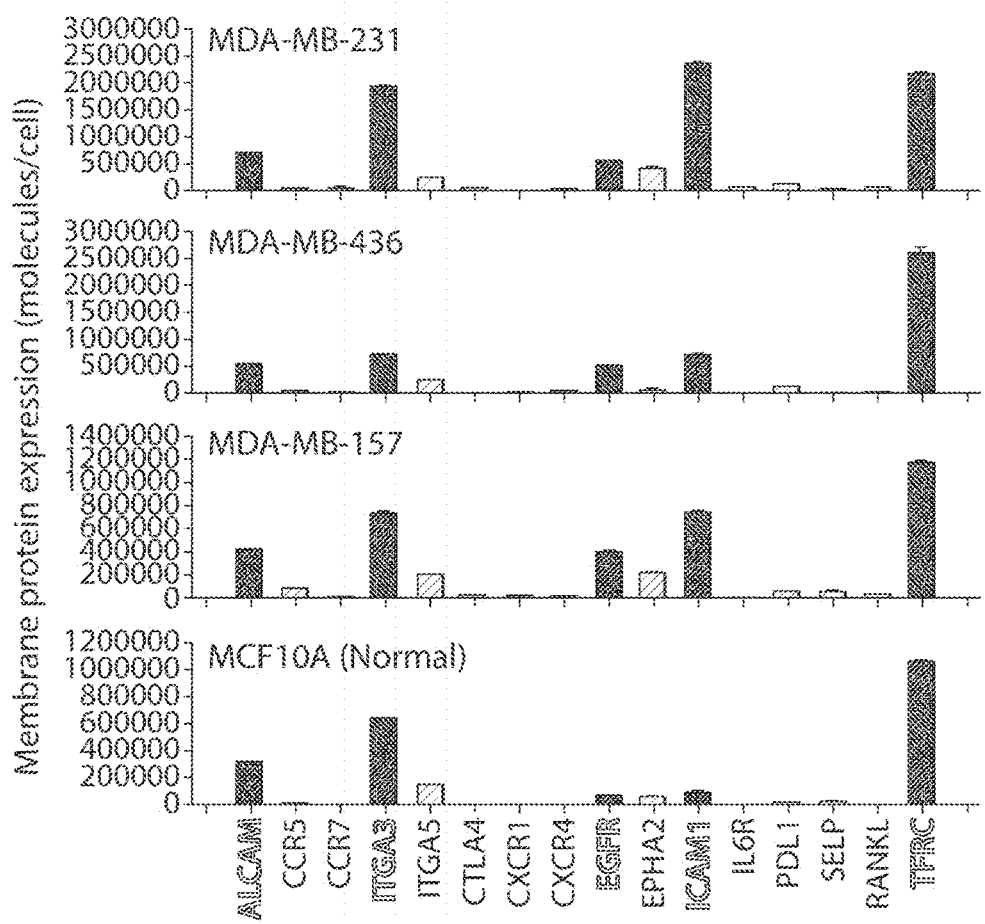

While several studies have shown that "dual-ligand targeting" can enhance the delivery of nanotherapeutics to certain tumor types, little has been done to develop rationally designed target selection. To address this issue, an unbiased and quantitative method was designed to select and identify optimal target combinations for complementary targeting that could be generally applicable to many cancer types or other diseases. A panel of 68 common cancer targets in human TNBC cells was screened using comparative flow cytometric analyses. In FIG. 10A and Table 5, the surface protein expression of cancer targets in three human TNBC cell lines (MDA-MB-231, MDA-MB-436, and MDA-MB-157) was quantified in comparison with normal human mammary epithelial MCF10A cells. Of the 68 screened targets, 16 candidates were found to be commonly overexpressed in all three TNBC cell lines, and were selected for further evaluation (FIG. 10B). As shown in FIG. 10C, ALCAM, ITGA3, EGFR, ICAM1, and TFRC emerged as the most overexpressed TNBC targets relative to IgG controls among the 16 candidates. However, ALCAM, ITGA3, TFRC were also found to be highly expressed in normal MCF10A cells which, if targeted, may cause off-target effects in normal mammary tissues (FIG. 10C). For these reasons, ALCAM, ITGA3 and TFRC were excluded and ICAM1 and EGFR were selected as the optimal targets for TNBC complementary targeting due to their high expression in TNBC cells and very low expression in normal cells relative to the other candidates. It was recently reported that ICAM1 is a novel TNBC target; EGFR was also studied as a therapeutic target for TNBC. Both ICAM1 and EGFR are molecular targets for FDA-approved drugs. However, to date, ICAM1 and EGFR have not been investigated as a target combination for TNBC-specific drug delivery.

Figure 10D:
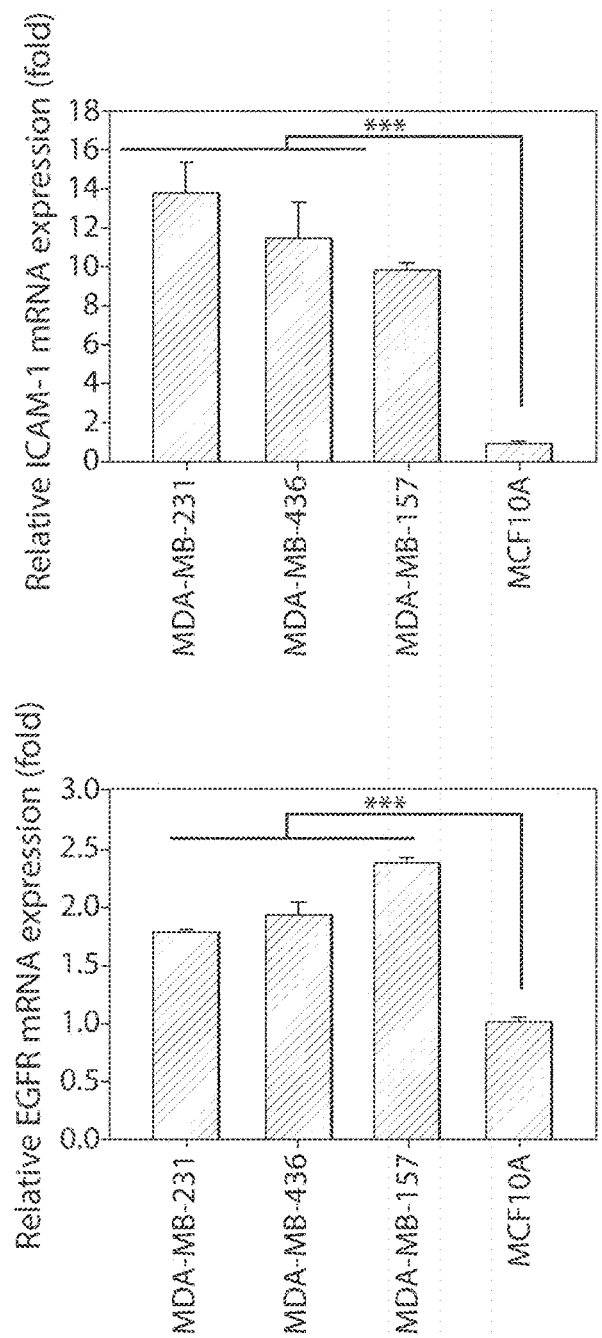

Next the molecular ratio and organization of ICAM1 and EGFR on TNBC cell surfaces were measured. As shown in Table 6, the surface protein densities of ICAM1 and EGFR on TNBC cells and normal mammary epithelial cells were quantified. The overexpression of ICAM1 and EGFR in TNBC cells was validated at the gene expression level using qRT-PCR (FIG. 10D). Results were consistent with their protein levels on both TNBC and normal cells. The ICAM1/EGFR surface density ratio for each type of TNBC cell: 4.2/1 for MDA-MB-231, 1.5/1 for MDA-MB-436, and 1.8/1 for MDA-MB-157 (Table 6) was calculated. MDA-MB-231 and MDA-MB-436 were selected for further investigation as they exhibited the highest and lowest ratio of ICAM1/EGFR. These ICAM1/EGFR surface densities and molecular ratios represent critical design parameters for engineering TNBC-specific DCLs, given that they are the bases for determining the amount and ratio of ICAM1 and EGFR antibodies to be conjugated on the surface of DCLs. This, in turn, facilitates precisely matched, multivalent ligand-receptor interactions with TNBC cells.

Figure 10E:
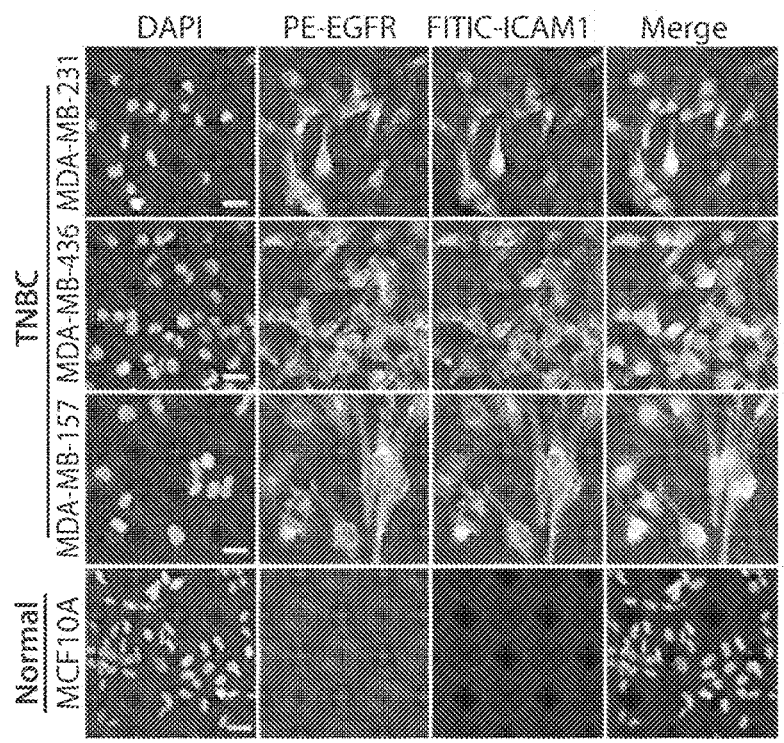
Figure 10F:
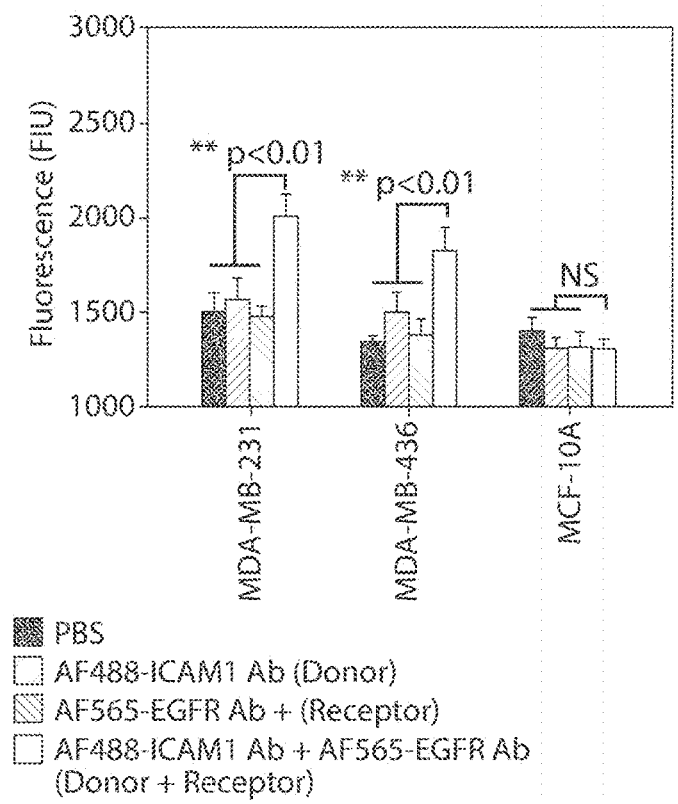

Notably, immunofluorescent staining of ICAM1 and EGFR on TNBC cells revealed the overlapped staining of ICAM1 and EGFR (merged fluorescent images in FIG. 10E), indicating that ICAM1 and EGFR are co-localized in close spatial proximity on the cell membrane. The colocalization of two receptors is another key design parameter in the engineering of DCLs because complementary targeting requires ICAM1 and EGFR antibodies on the DCL surface to be in contact with both target receptors on the TNBC cell membrane at the same time. Therefore, ICAM1 and EGFR must spatially reside within the distance of the DCL diameter (approximately 130 nm). The co-localization of ICAM1 and EGFR on TNBC cells was also confirmed using a fluorescence resonance energy transfer (FRET) assay. As demonstrated in FIG. 10F MDA-MB-231, MDA-MB-436, and MCF10A cells were co-stained with Alexa Fluor 488-ICAM1 antibody (FRET donor, excitation/emission, 495/515 nm) and Alexa Fluor 555-EGFR antibody (FRET receptor, excitation/emission, 519/565 nm). FRET signals from the donor-receptor pair were observed on both TNBC cells but were absent in normal MCF10A cells, indicating that ICAM1 and EGFR are present within the Förster radius of 10 nm (the maximum distance for FRET events) on TNBC cell membranes.

Figure 10G:
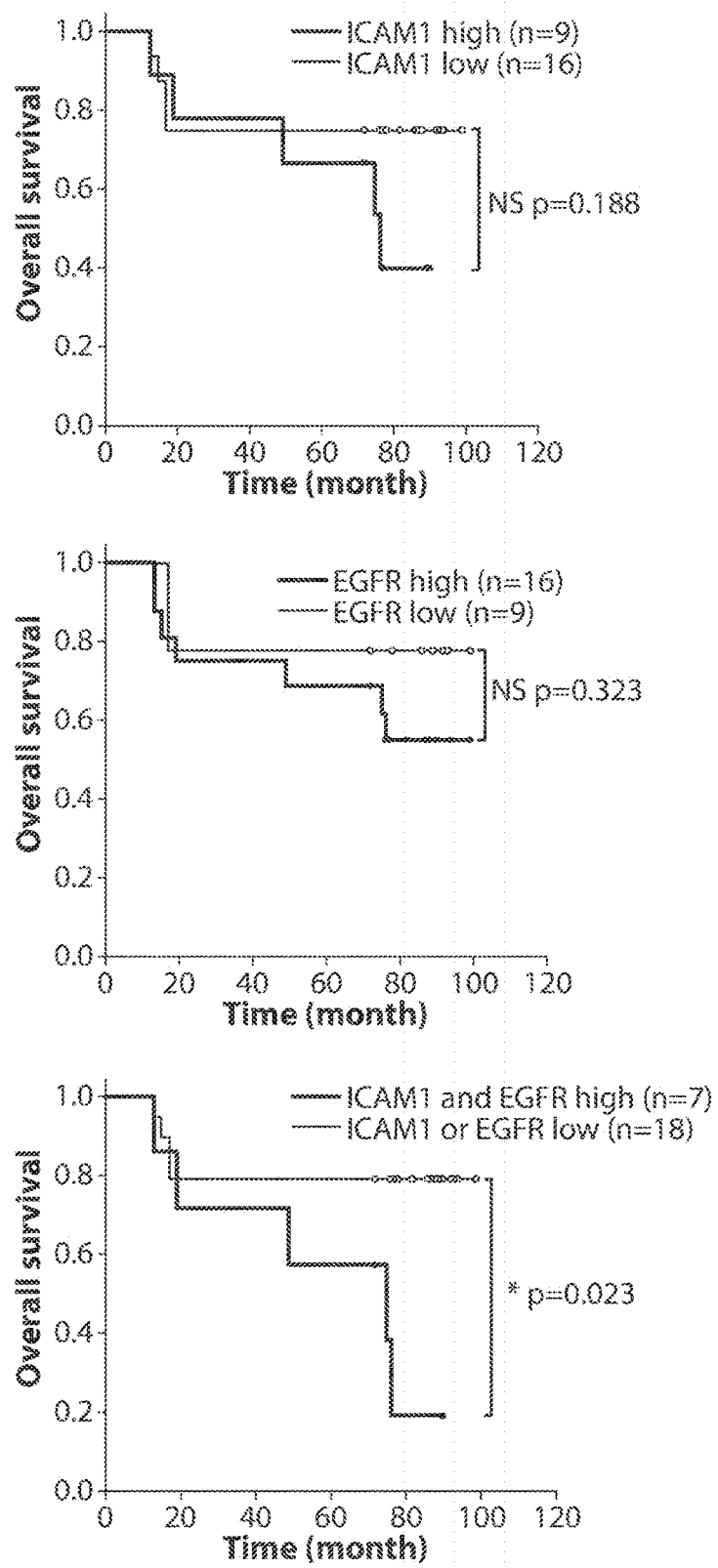

Importantly, the potential impact of ICAM1 and EGFR overexpression on the overall survival of basal-like breast cancer patients (majority are TNBC cases) in a cohort of 25 specimens was analyzed using the R2: Genomics Analysis and Visualization Platform (https://hgserver1.amc.nl/, Datasheet: Tumor Breast—Bergh—159—MAS5.0—u133a). Basal-like breast cancer patients with high expression of both ICAM1 and EGFR demonstrated the worst prognosis (FIG. 10G, P=0.023, Log-rank test) relative to overexpression of ICAM1 and EGFR alone. These findings suggest that high expression of ICAM1 in combination with high expression of EGFR may serve as an important clinical biomarker of poor prognosis in basal-like breast cancer patients.

Engineering Complementary Targeting Liposomes (DCLs)

Figure 13A:
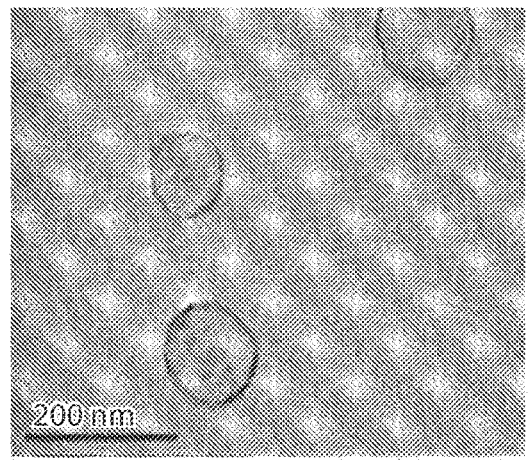
FIGS. 13A-13B (FIG. 13A) Transmission electron microscopy image of dual complementary liposomes (DCL without payload). Scale bar represents 200 nm.
Figure 13B:
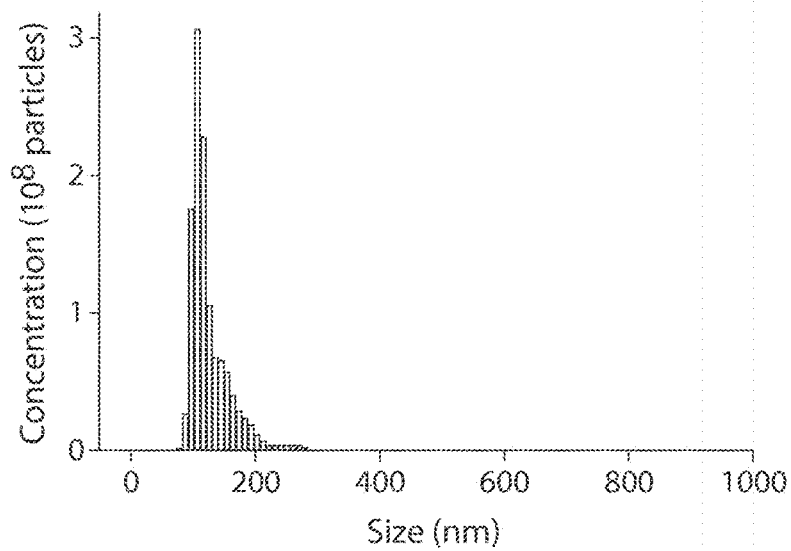

Non-targeting liposomal doxorubicin (e.g., Doxil and Myocet) is FDA-approved; these breast cancer nanomedicines exhibit fewer adverse effects and better safety profiles than conventional chemotherapeutics. Unfortunately, these non-targeting liposomes failed to exhibit significantly improved clinical benefits against TNBC due to their limited tumor delivery. It was reasoned that combining the novel complementary targeting strategy described herein with clinically used liposomal doxorubicin would enable a nanotherapeutic to specifically recognize and target TNBC tumors and spare healthy organs and tissues. This approach increases the drug delivery to, and dosage in, tumors, reduces non-specific uptake, and attenuates adverse side-effects. To test this, a proof-of-principle DCL was designed by covalently conjugating both ICAM1 and EGFR neutralizing antibodies on the surface of liposomal doxorubicin at optimal antibody ratios for different types of TNBC cells (FIGS. 5A-5H). For example, 4.2/1 (ICAM1/EGFR antibody) for MDA-MB-231 and 1.5/1 for MDA-MB-436 cells. The size and monodispersity of synthesized DCLs were characterized by dynamic light scattering measurements (Table 7 and FIG. 13). All DCLs and control liposomes exhibited uniform hydrodynamic radii of approximately 130±30 nm and zeta potentials between −6 to −10 mV. The ICAM1/EGFR antibody ratios conjugated on DCL surfaces were also measured and are close to their theoretical values (Table 4).

Complementary Targeting Specifically Enhances Liposome Binding to TNBC Cells

Figure 5D:
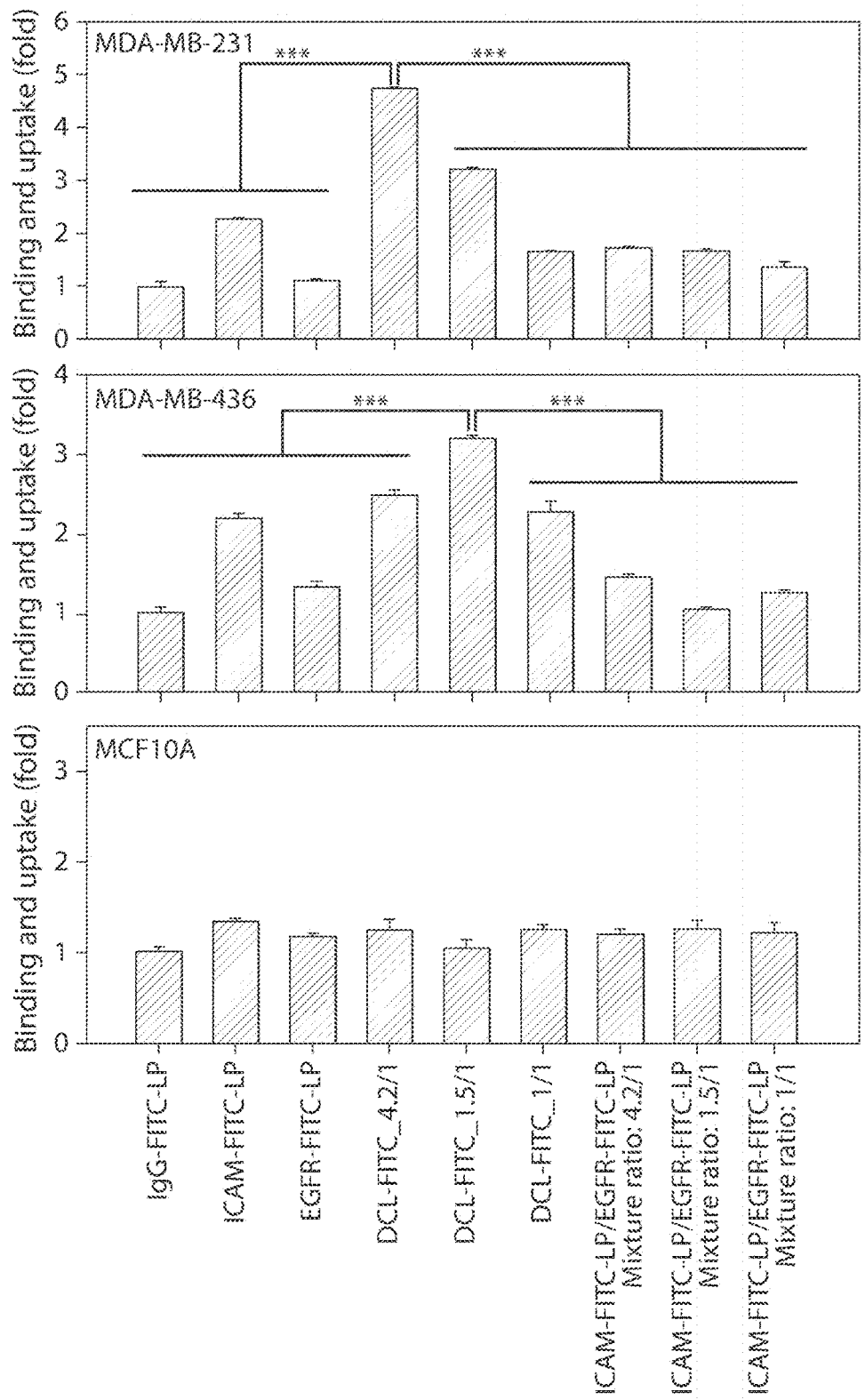
Figure 5E:
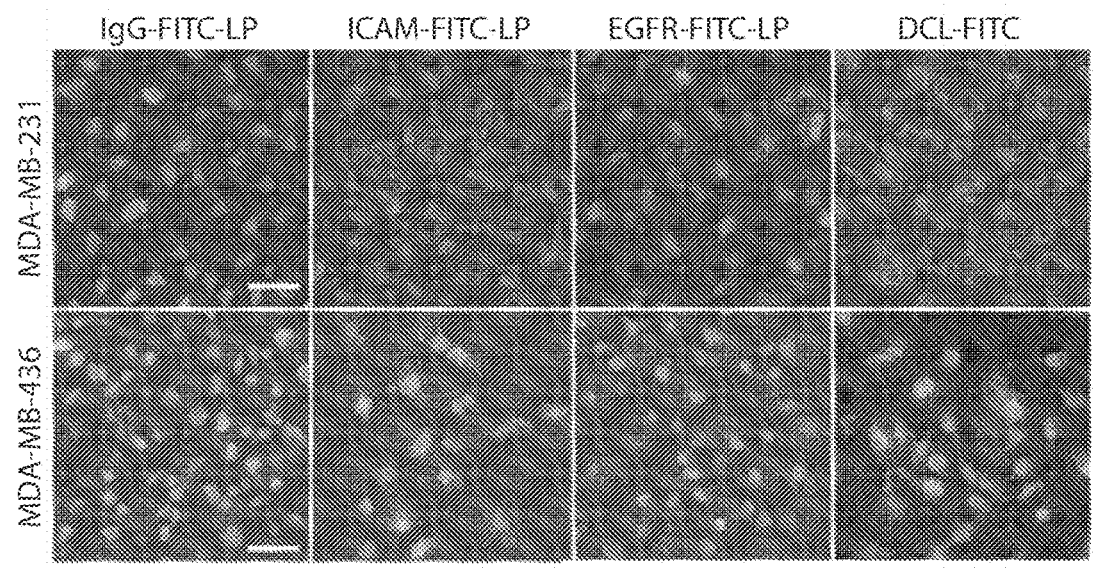

TNBC binding and uptake of DCLs were determined by both flow cytometry and immunofluorescent staining. As demonstrated in FIG. 5D, MDA-MB-231 and MDA-MB-436 cells were treated with FITC-labeled DCLs with different ICAM1/EGFR antibody ratios (DCL-FITC_4.2/1, _1.5/1, _1/1), FITC-labeled ICAM1 or EGFR single targeting liposomes (ICAM-FITC-LP or EGFR-FITC-LP), or non-targeting IgG-FITC-LP in the presence of serum (10% FBS). Cells were also treated with single targeting liposomes mixed at different ratios. DCL-FITC_4.2/1 (ICAM1/EGFR antibody ratio 4.2/1, optimized for MDA-MB-231 cells) exhibited a 4.7-fold increase in binding with MDA-MB-231 cells as compared to IgG-FITC-LP, significantly higher than other tested DCLs and ICAM1 or EGFR single targeting liposomes. It is very important to note that simply mixing ICAM1 and EGFR single targeting liposomes at certain molecular ratios (e.g., 4.2/1, 1.5/1, and 1/1) did not improve their cellular binding in comparison with DCLs (FIG. 5D). This is due to the fact that the mixture of single targeting liposomes alone lacks the multivalent ligand-receptor interaction towards TNBC cells and also causes steric hindrance as both ICAM-FITC-LP and EGFR-FITC-LP compete to bind co-localized ICAM1 and EGFR in the same cell surface regions. Consistently, DCL-FITC_1.5/1 (ICAM1/EGFR antibody ratio 1.5/1, optimized for MDA-MB-436 cells) also exhibited the highest cellular binding with MDA-MB-436 cells (FIG. 5D). Meanwhile, no obvious changes in cellular binding were observed in normal MCF10A cells treated with DCLs or control liposomes due to their lack of either ICAM1 or EGFR expression. Increased cellular binding with DCL-FITC was also observed with immunofluorescent staining (FIG. 5E). These results demonstrated that the ICAM1/EGFR antibody ratio plays a critical role in regulating multivalent ligand-receptor interactions between DCLs and TNBC cells. As illustrated in FIG. 3, only when the ICAM1/EGFR antibody ratio on DCLs precisely complements the ICAM1/EGFR expression ratio on TNBC cells, does the multivalent ligand-receptor interaction reach its maximum efficiency and generate the strongest cooperative adhesion specifically toward TNBC cells, thereby significantly promoting TNBC cellular binding.

Complementary Targeting Significantly Enhances Liposome Internalization in TNBC Cells The advantages of complementary targeting are not limited to the increased TNBC cellular binding. It was observed that this strategy substantially enhanced TNBC cell internalization of liposomes via cooperative endocytosis pathways (FIG. 3). It is known that EGFR internalization mainly depends on clathrin-mediated endocytosis, while ICAM1 internalization relies on an alternative cell adhesion molecule (CAM)-mediated pathway. It is likely that DCLs may simultaneously bind and activate both ICAM1 and EGFR internalization pathways and enter TNBC cells via a synergy of clathrin- and CAM-mediated endocytosis. To test this Trypan Blue quenching assays were performed on DCL-FITC-treated TNBC cells to block the extracellular fluorescence from bound and non-internalized DCL-FITCs and the internalization ratio of DCL-FITCs was calculated by dividing the cellular fluorescence of internalized DCL-FITCs by the total cellular fluorescence composed of both extracellular and internalized DCL-FITCs (FIG. 5E). Surprisingly, ICAM1 or EGFR single targeting liposomes, which exhibited increased cellular binding (FIGS. 5D and 5E), bound to TNBC cell surfaces via ICAM1 or EGFR antibody-antigen interactions and were not effectively internalized by TNBC cells. This may be due to the limited efficacy of the ICAM1 or EGFR single endocytosis pathway. In contrast, DCL-FITCs significantly restored the internalization ratio back to 42.7% for MDA-MB-231 cells and 60.9% for MDA-MB-436 cells while maintaining their highly specific TNBC cellular binding (FIG. 5E). The IgG group demonstrated a high internalization ratio (40-60%) due to its low affinity for the cell surface compared to other groups. These results demonstrated that the complementary targeting strategy enables liposomes to enter TNBC cells more efficiently via cooperative endocytosis pathways. Though naturally occurring proteins (e.g., LRP1) have been reported to harness cooperative endocytosis pathways, it is demonstrated herein for the first time that synthetic nanocarriers can exploit multiple endocytosis pathways to improve cell internalization. The detailed biomechanism(s) of this synergy between clathrin and CAM-mediated endocytosis pathways merits further investigation.

Complementary Targeting Cooperatively Blocks ICAM1 and EGFR Signaling Cascades

Figure 5F:
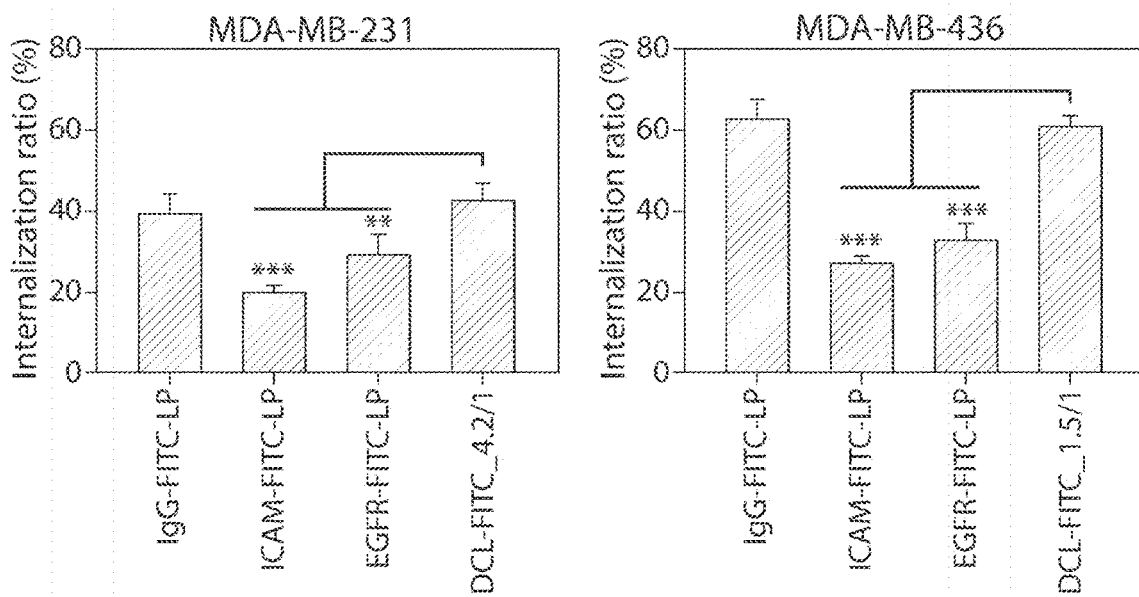
Figure 5G:
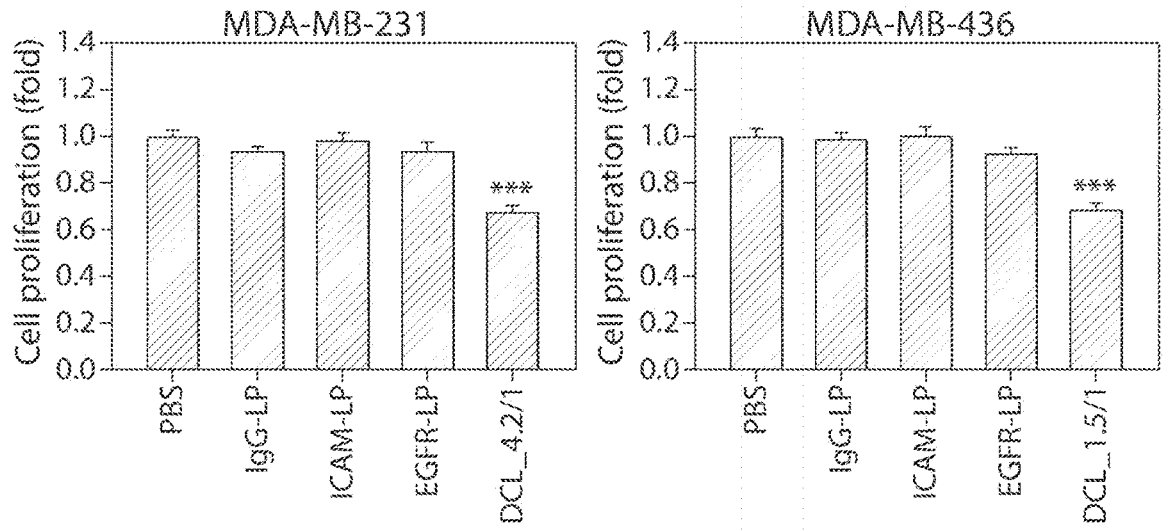

The DCLs described herein were engineered with ICAM1 and EGFR neutralizing antibodies that could simultaneously block ICAM1 and EGFR signaling cascades in TNBC cells (FIG. 3). The EGFR neutralizing antibody Cetuximab is a FDA-approved anti-tumor agent for treating a variety of metastatic tumors. ICAM1 neutralizing antibodies, Enlimomab and BI-505, have shown promising anti-tumor activities against many cancers. It was reasoned that the DCL is not only a drug delivery nanocarrier but also a TNBC-targeted therapeutic agent that synergistically inhibits both ICAM1 and EGFR pathways in TNBC cells and therefore blocks multiple processes during cancer progression. Therefore, the impact of the DCL vehicle (without Dox) on both TNBC cell proliferation and invasion was investigated. DCLs exhibited a 30-40% inhibitory effect on TNBC cell proliferation in vitro in both MDA-MB-231 and MDA-MB-436 cells (FIG. 5F). Moreover, as presented in FIGS. 5A-5C, DCLs exhibited potent inhibitory activity against TNBC cell invasion. The number of invaded MDA-MB-231 and MDA-MB-436 cells was significantly reduced by 64% and 46%, respectively, by DCL treatment in comparison with PBS controls. Notably, a similar inhibitory effect was observed with ICAM-LP but not with EGFR-LP, indicating that the inhibitory function of DCLs against cell invasion may be attributed to the blockade of the ICAM1 pathway rather than the EGFR pathway. This inhibitory effect was consistent with previous studies using free ICAM1 neutralizing antibodies. Based on these data, it was believed that ICAM1 and EGFR neutralizing antibodies of DCLs may work as bioactive therapeutic agents against TNBC progression and metastasis via synergistically blocking ICAM1 and EGFR pathways.

Figure 5H:
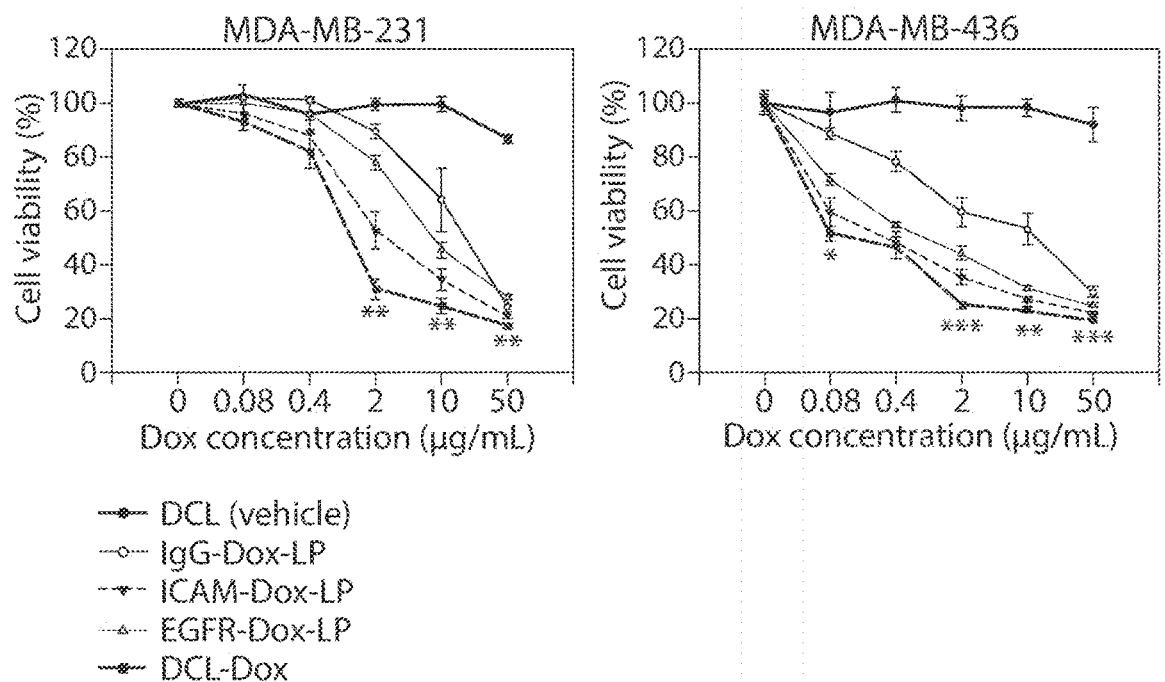

The potent inhibitory effects of this DCL vehicle on TNBC cell proliferation and invasion may further synergize with its chemotherapeutic payloads (e.g., doxorubicin) to generate maximal therapeutic benefits in vivo against TNBC progression and metastasis. To test this, DCLs was loaded with doxorubicin (DCL-Dox), a commonly used breast cancer chemotherapy drug, and evaluated its half maximal inhibitory concentration ($IC_{50}$) in two human TNBC cell lines. DCL-Dox_4.2/1 (optimized for MDA-MB-231 cells) showed significantly improved cytotoxicity against MDA-MB-231 cells, thirteen-fold higher than the cytotoxicity from IgG-Dox-LP (FIG. 5H). The quantified $IC_{50}$ for IgG-Dox-LP, ICAM-Dox-LP, EGFR-Dox-LP, and DCL-Dox_4.2/1 in MDA-MB-231 cells were 11.7, 2.4, 4.8, and 0.9 μg/mL, respectively. A similarly improved cytotoxicity profile was also observed with DCL-Dox_1.5/1 in MDA-MB-436 cells, achieving the lowest $IC_{50}$ of 0.04 μg/mL for DCL-Dox_1.5/1 compared with 3.74 μg/mL for IgG-Dox-LP, 0.08 μg/mL for ICAM-Dox-LP, and 0.23 μg/mL for EGFR-Dox-LP. In summary, DCL-Dox exhibited the lowest $IC_{50}$ in both MDA-MB-231 and MDA-MB-436 cells due to their complementary targeting capability.

DCL Inhibits Orthotopic TNBC Tumor Growth and Metastasis

Figure 8E:
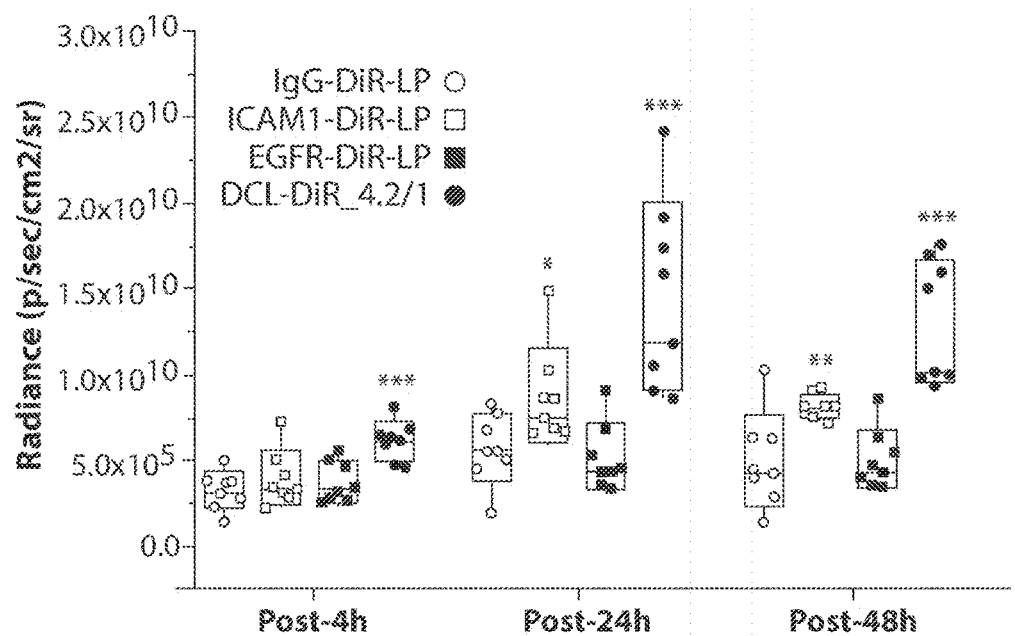
Figure 8F:
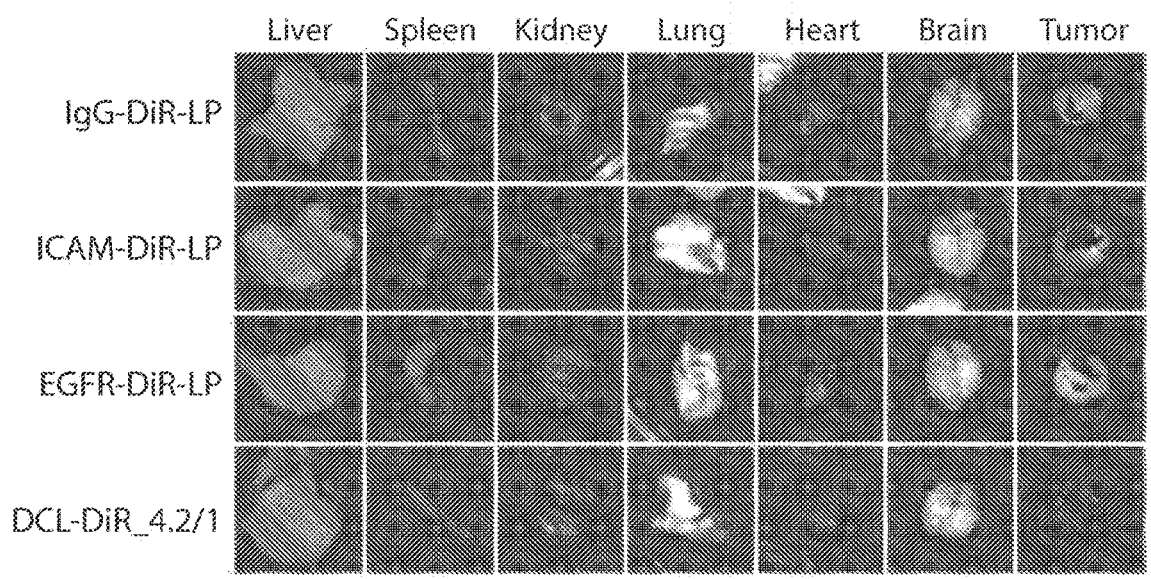

First, the in vivo tumor-targeting activity of DCLs was evaluated using near infrared (NIR) fluorescent imaging in an orthotopic TNBC tumor model (FIG. 8A). DCL_4.2/1 was labeled with DiR, a NIR lipid dye, (DCL-DiR_4.2/1) and intravenously injected it into MDA-MB-231 tumor-bearing mice. IgG-DiR-LP, ICAM-DiR-LP, and EGFR-DiR-LP were used as controls. In vivo NIR imaging was performed at 6 h, 24 h, and 48 h post-injection. Among four tested formulations, the DCL-DiR_4.2/1 group demonstrated the highest tumor accumulation at all time points (FIG. 8A). Quantified NIR signals confirmed that the tumor accumulation of DCL-DiR_4.2/1 was 2.8-fold higher than that of IgG-DiR-LP at 24 h after a single tail vein administration and was almost twice the amount of the highest single targeting group (ICAM-DiR-LP) (FIG. 8E). The biodistribution of DCL-DiR_4.2/1 was evaluated using ex vivo quantification of NIR signals in six organs and tumors excised from mice at 48 h (FIGS. 8D and 8F). Correlating with in vivo whole mice imaging data, DCL-DiR_4.2/1 accumulated in excised tumors approximately 2-fold higher than that of IgG-DiR-LP (FIG. 8D). These results demonstrated that complementary targeting is more effective than conventional single targeting approaches in recognizing and targeting TNBC tumors in vivo.

Next, the therapeutic efficacy of doxorubicin-loaded DCL_4.2/1 (DCL-Dox_4.2/1) in inhibiting orthotopic TNBC tumor growth and metastasis was examined (FIG. 9A). MDA-MB-231 tumor bearing mice were randomly divided into six groups and received treatment of PBS (sham), free doxorubicin (Free Dox), IgG-Dox-LP, ICAM-Dox-LP, EGFR-Dox-LP, or DCL-Dox_4.2/1, respectively, at a Dox dosage of 2.5 mg/kg via retro-orbital injection. As shown in FIGS. 9A and 9C, after a 21-day treatment regimen, DCL-Dox_4.2/1 exhibited the highest inhibitory effect on TNBC tumor growth among all tested groups. The quantified tumor mass revealed that DCL-Dox significantly reduced TNBC tumor growth by 70.3%, approximately 3-fold more efficient than IgG-Dox-LP (FIG. 9B). Furthermore, as shown in FIG. 12, DCL-Dox_4.2/1 substantially inhibited spontaneous metastasis compared to other groups (1/10 mice versus 5/9 to 8/8 mice).

DCL Inhibits TNBC Lung Metastasis

Figure 11A:
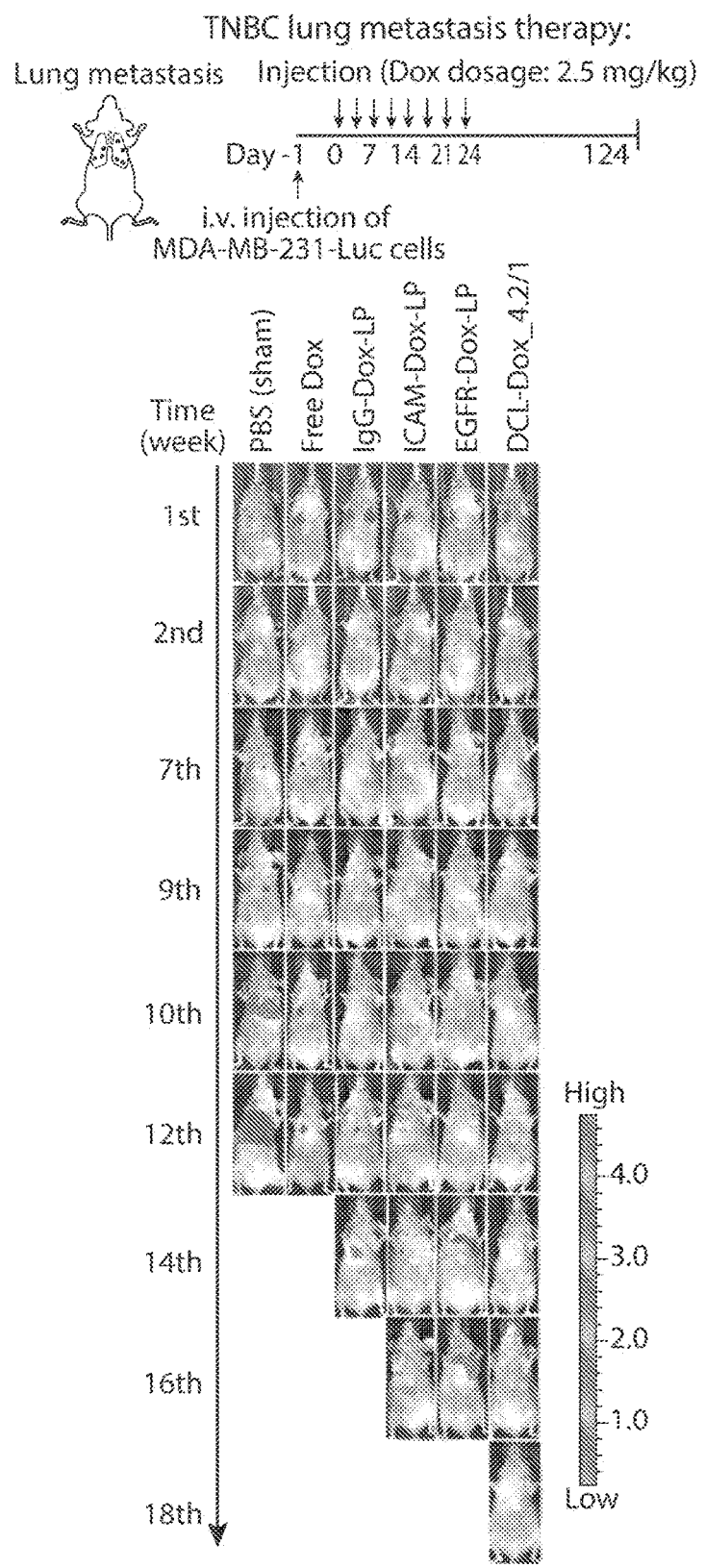
FIG. 11A-11I show that DCL-Dox inhibits TNBC lung metastasis and improves survival.
Figure 11B:
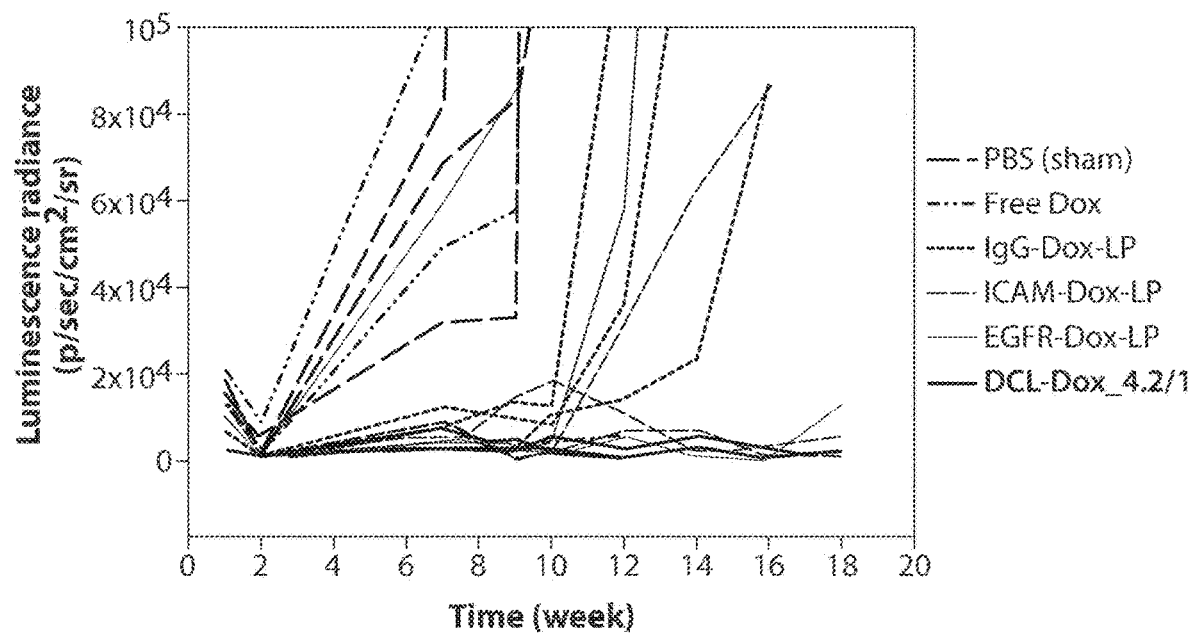
Figure 11C:
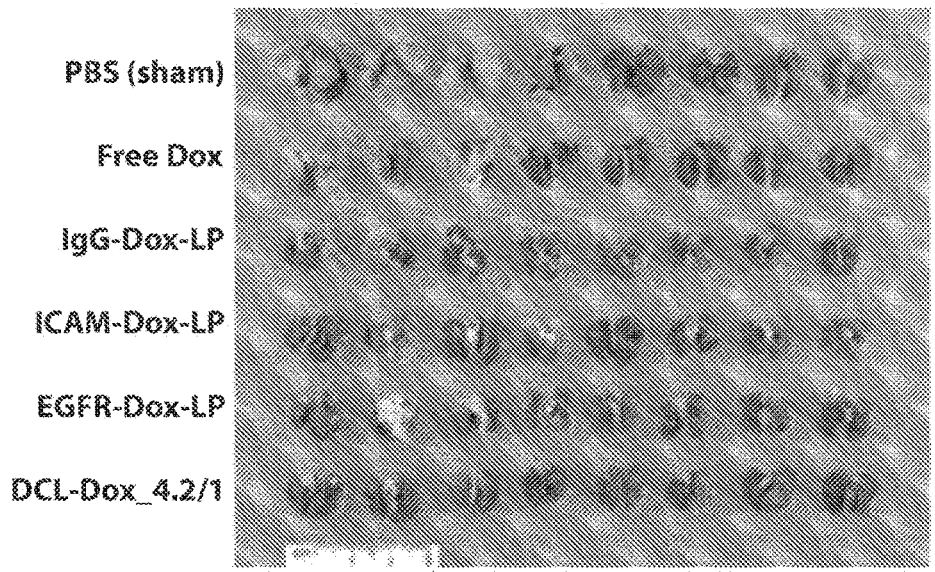
Figure 11D:
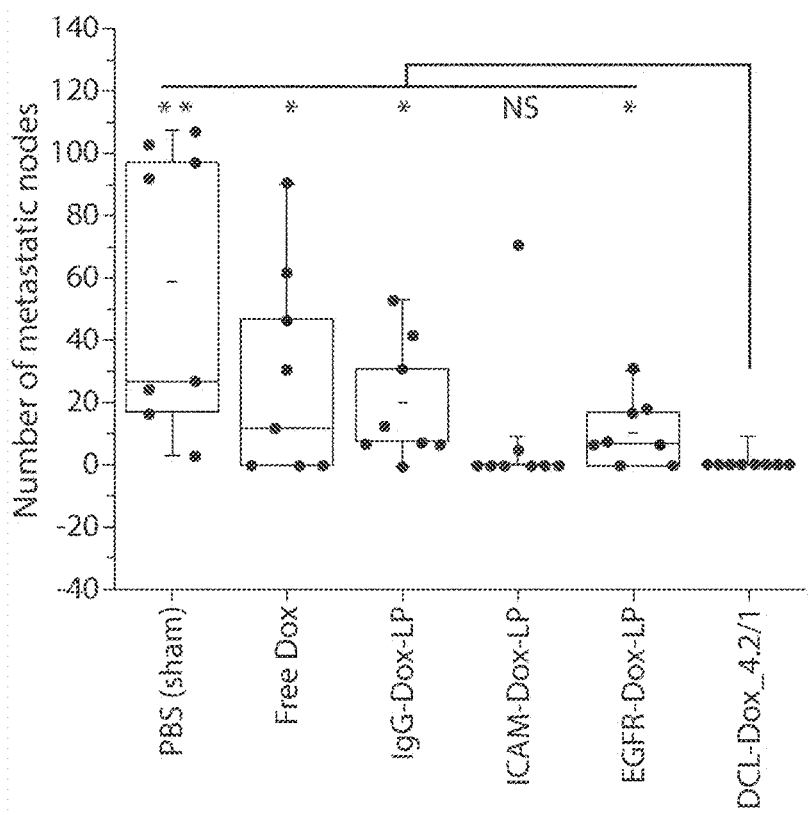
Figure 11E:
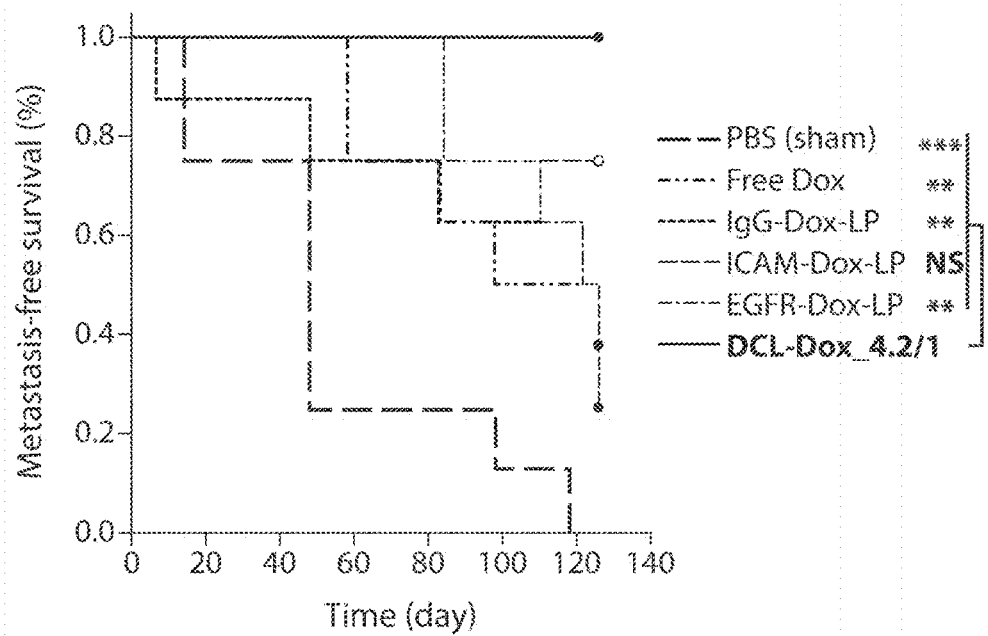
Figure 11F:
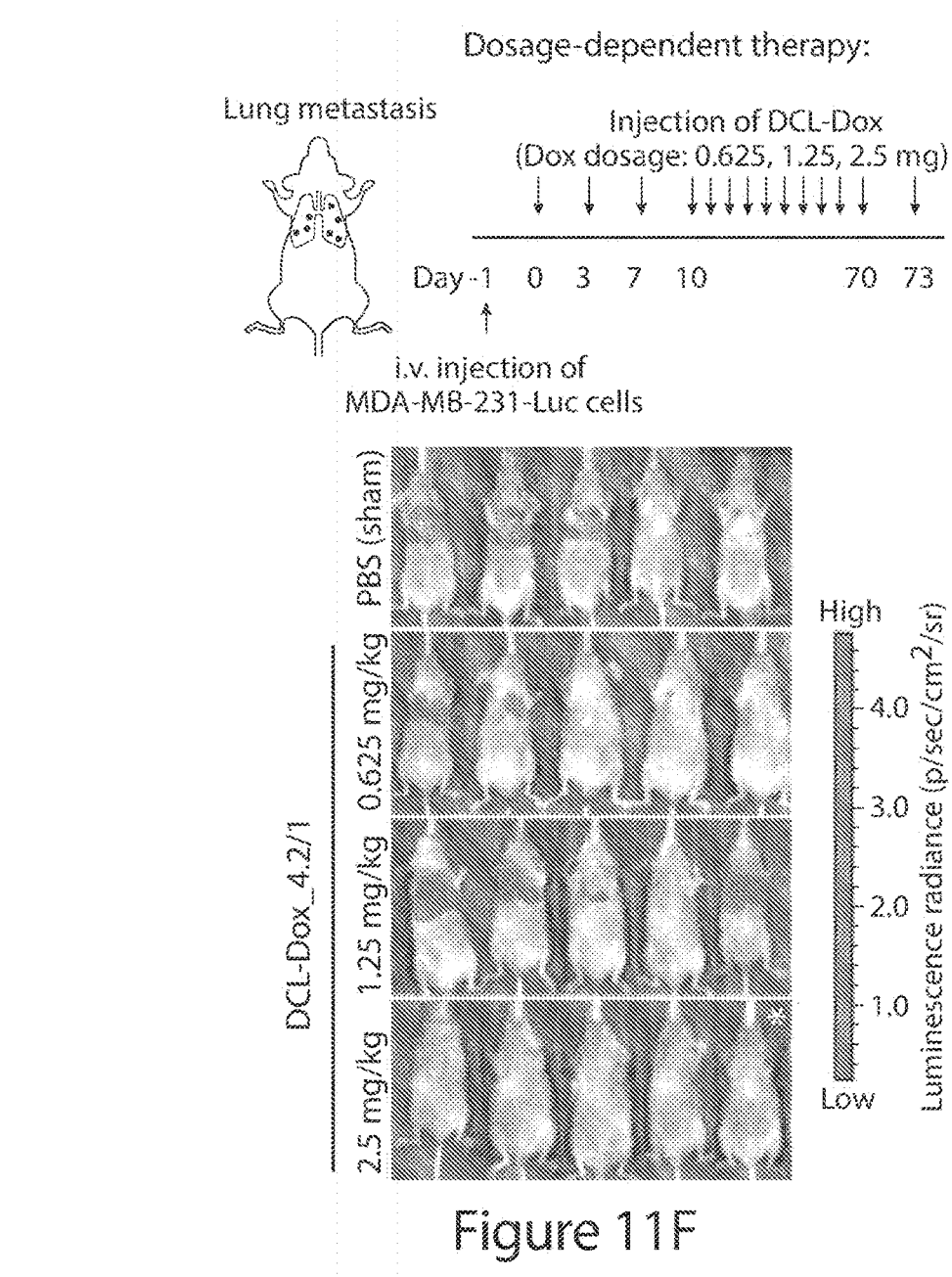

To extend the application of complementary targeting strategy to metastatic TNBC, the anti-tumor activity of DCL-Dox was examined in a lung metastasis model, which is known to be more aggressive and more refractory to conventional chemotherapy than an orthotopic tumor model. TNBC lung metastases were generated by tail vein administration of luciferase-labeled MDA-MB-231 (MDA-MB-231-Luc) cells (FIG. 11A). After confirming the formation of lung metastasis by in vivo bioluminescence imaging (FIG. 11A), mice were randomly divided into the same treatment groups used in the orthotopic model and administered via retro-orbital injection. After a 21-day treatment regimen, lung metastasis in each group was closely monitored by weekly bioluminescence imaging up to 124 days (FIGS. 11A and 11B). As shown in FIGS. 11A and 11B, DCL-Dox completely inhibited the progression of TNBC lung metastasis compared to the other groups. None of the mice treated with DCL-Dox_4.2/1 developed lung metastases, whereas 6/8 mice in the non-targeting IgG-Dox-LP and EGFR-Dox-LP group developed metastases (FIG. 12). Interestingly, ICAM-Dox-LPs also exhibited a slightly lower inhibitory activity (2/8 mice) than DCL-Dox, which correlates with the in vitro cell invasion studies (FIG. 11F). The DCL-Dox_4.2/1 complete inhibition of TNBC metastasis formation on excised lungs was confirmed in FIGS. 11C and 11D. It was further found that this potent metastasis-inhibitory activity of DCL-Dox_4.2/1 led to significant survival benefits. As shown in FIG. 11E, DCL-Dox substantially improved metastasis-free survival in comparison with all groups except ICAM-Dox-LP.

Determination of the Optimal Dosage for DCL Therapy

Figure 11G:
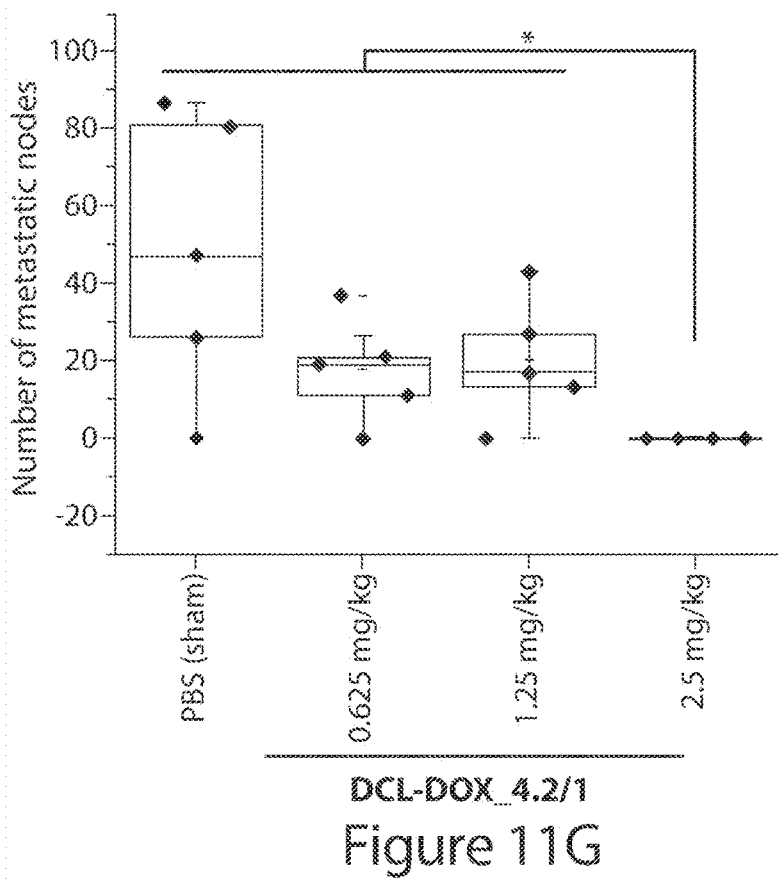
Figure 11H:
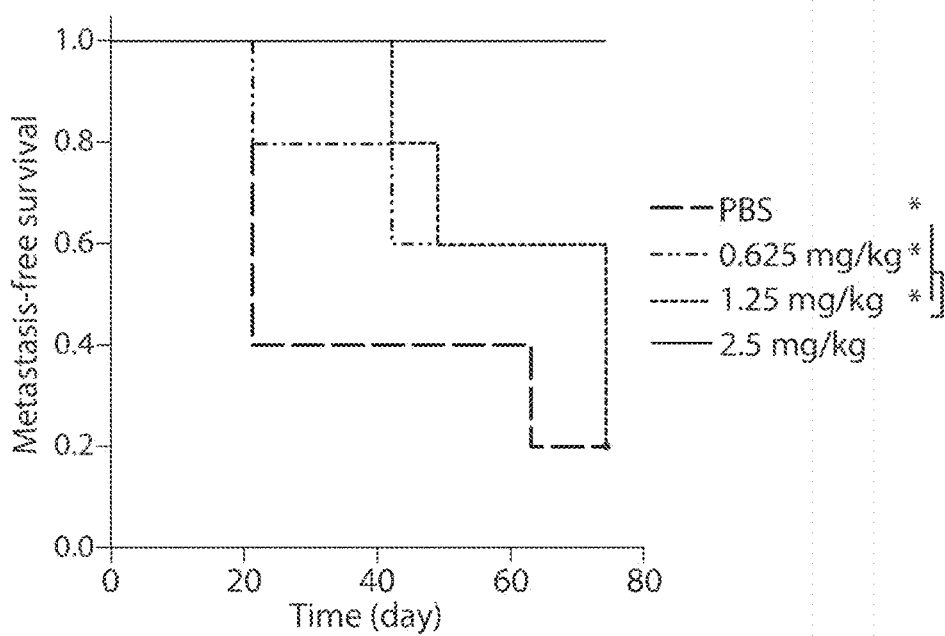
Figure 11I:
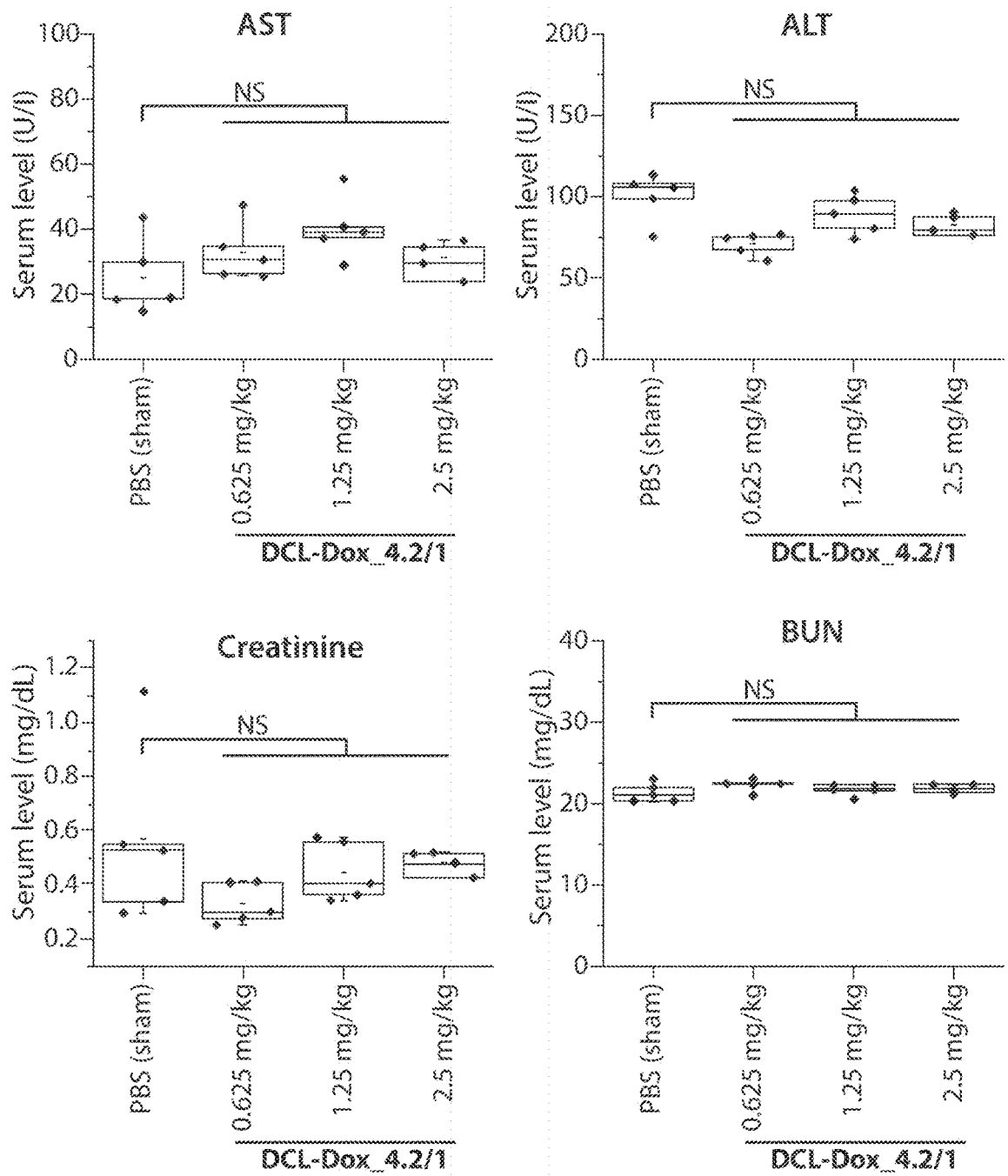

A dosage-dependent study was performed to determine the minimum effective dosage of DCL-Dox treatment (FIG. 11F). Mice with MDA-MB-231 lung metastases were treated with PBS (sham) or DCL-Dox_4.2/1 at three dosages (0.625, 1.25, and 2.5 Dox mg/kg) for up to 75 days. DCL-Dox at the dosages of 0.625 and 1.25 mg/kg did not inhibit lung metastasis as effectively as DCL-Dox at the dosage of 2.5 mg/kg (FIGS. 11F and 11G). Kaplan-Meier survival analysis further confirmed the significantly increased survival benefit of the 2.5 mg/kg dosage compared to the lower dosages (FIG. 11H). Thus, DCL-Dox_4.2/1 at the dosage of 2.5 mg/kg Dox was considered to be the optimal dosage for treating metastatic MDA-MB-231 tumors. Moreover, the chronic liver and renal toxicity of DCL-Dox_4.2/1 treatment was evaluated via blood chemistry analysis. At the end of the DCL-Dox_4.2/1 dosage-dependent study (day 75), the serum from each dosage group was collected and aspartate aminotransferase (AST) and alanine aminotransferase (ALT) levels were measured to evaluate liver toxicity. As shown in FIG. 11I, among all DCL-Dox_4.2/1 dosages, none of them, including the highest one, induced any elevation in either AST or ALT levels compared with the PBS group. Similarly, the renal toxicity of DCL-Dox_4.2/1 was evaluated by measuring creatinine and blood urea nitrogen (BUN) levels and no renal toxicity was observed among these DCL-Dox_4.2/1 dosage groups (FIG. 11I). It is noteworthy that the highest Dox dosage at 2.5 mg/kg for 75 days in mice is equivalent to a Dox cumulative dosage of 1760 mg/m$^2$ in human, which is close to the Dox life time cumulative dosage of 2220 mg/m$^2$ in human. These in vivo data demonstrate that DCL-Dox_4.2/1 at 2.5 mg/kg dosage exhibited the highest inhibitory activity against primary and metastatic TNBC tumors while exhibiting no systemic toxicity.

Conclusion

In summary, it was demonstrated herein that complementary targeting is a highly precise and effective strategy to recognize and target TNBC tumors both in vitro and in vivo. A dual complementary targeting, doxorubicin encapsulating liposome that significantly inhibits TNBC tumor progression and metastasis in both orthotopic tumor and lung metastasis models was engineered. In addition, an unbiased and quantitative screening method to identify optimal candidates for targeted drug delivery was provided, which provides the opportunity for other investigators to readily apply this complementary targeting strategy to the design of nanomedicines to treat other cancers or diseases. The biomechanisms by which complementary targeting nanotherapeutics interact with biological systems was elucidated, providing tunable parameters to optimize tumor specificity and therapeutic efficacy for multivalent nanomedicines.

Materials and Methods

Dulbecco's phosphate buffered saline (PBS), 4',6-diamidino-2-phenylindole (DAPI), 0.25% trypsin/2.6 mM ethylenediaminetetraacetic acid (EDTA) solution, Gibco® Dulbecco's Modified Eagle Medium (DMEM), Gibco®DMEM/F12 (1:1), and Gibco™ 0.4% Trypan Blue Solution were purchased from Invitrogen (Carlsbad, Calif., USA). 1-Ethyl-3-(3-dimethylaminopropyl) carbodiimide hydrochloride (EDC), N-hydroxysuccinimide (NHS), bovine serum albumin (BSA), anhydrous dimethyl sulfoxide (DMSO), doxorubicin (Dox), fluorescein isothiocyanate-dextran (FITC-dextran, MW 10 kD), aspartate aminotransferase (AST) activity assay kit, alanine aminotransferase (ALT) activity assay kit, creatinine activity assay kit, and urea activity assay kit were purchased from Sigma-Aldrich (St. Louis, Mo., USA). Corning™ BioCoat™ Matrigel™ Invasion Chamber with BD Matrigel Matrix, Lab-Tek II Chamber Slide System, formaldehyde, chloroform, anhydrous ethanol (EtOH), Slide-A-Lyzer dialysis cassette (MWCO 10 KD), 1,1'-Dioctadecyl-3,3,3',3'-Tetramethylindotricarbocyanine Iodide (DiR), and Diff-Quik Stain Set were purchased from Thermo Fisher Scientific (Pittsburgh, Pa., USA). Mouse anti-human ICAM1 neutralizing antibody (Clone BBIG-I1) and immunoglobulin G (IgG) isotype were purchased from R&D Systems (Minneapolis, Minn., USA). Phycoerythrin (PE)-conjugated mouse/rat anti-human antibodies against 68 cancer target candidates (Table 5), FITC-ICAM1 antibody, Alexa Fluor 488-ICAM1 antibody, and FITC and PE-conjugated mouse IgG isotypes were purchased from BioLegend (San Diego, Calif., USA). Mouse anti-human EGFR neutralizing antibody (Clone LA1) and Alexa Fluor 555-EGFR antibody were purchased from EMD Millipore (Billerica, Mass., USA). 1,2-dioleoyl-sn-glycero-3-phosphocholine (DOPC) and 1,2-distearoyl-sn-glycero-3-phosphoethanolamine-N-[carboxy(polyethylene glycol)-2000] (DSPE-PEG-COOH) were purchased from Avanti Polar Lipids (Alabaster, Ala., USA). Quantum Simply Cellular microbeads were purchased from Bangs Laboratory (Fishers, Ind., USA). Qiagen RNeasy minikit was purchased from QIAGEN (Germantown, Md., USA). FLOAT-A-LYZER G2 dialysis tubing (MWCO 1,000 kDa) was purchased from Spectrum Laboratories (Rancho Dominguez, Calif., USA). 2

μm borosilicate beads were purchased from Thomas Scientific (Swedesboro, N.J., USA). Dojindo cell counting kit was purchased from Dojindo Molecular Technologies (Rockville, Md., USA). BD Vacutainer was purchased from Becton Dickinson (Franklin Lakes, N.J., USA).

Cell Culture

Three human TNBC cell lines (MDA-MB-231, MDA-MB-436, and MDA-MB-157) and one human non-neoplastic mammary epithelial cell line (MCF10A) were used in the presented study. All four cell lines were purchased from American Type Culture Collection (ATCC, Manassas, Va., USA). MDA-MB-231, MDA-MB-436, and MDA-MB-157 cells were cultured in DMEM, MCF10A in DMEM/F12 (1:1), with all recommended supplements. All cells were maintained at 37° C. in a humidified incubator with 5% $CO_2$. Luciferase-labelled MDA-MB-231 (MDA-MB 231-Luc-D3H2LN) cells were purchased from Perkin Elmer (Hopkinton, Mass., USA) and cultured using the same condition as MDA-MB-231 cells.

Screening and Identification of Optimal Targets for COMP-Targeting

Cell membrane expression of molecular target candidates was evaluated using a BD FACSCalibur Flow Cytometer (BD Biosciences, San Jose, Calif., USA) as described previously. Briefly, $10^6$ cells were collected and rinsed twice through suspension-spin cycles. Cells were blocked by 1% BSA in PBS for 30 min in an ice bath. After BSA blocking, cells were incubated with PE-conjugated antibodies for 1 h at RT. Cells were rinsed with 1% BSA in PBS twice, resuspended in PBS, and evaluated by flow cytometry. Density of molecular targets on the cell surface was determined with reference to Quantum Simply Cellular microbeads, using the protocol provided by the manufacturer.

Quantification of Gene Expression

Gene expression levels of ICAM-1 and EGFR in TNBC cells were characterized using qRT-PCR. Cells were cultured at $3\times10^5$ cells/well in 6-well cell culture plate overnight. Cells were then removed from each well by incubating with a 0.25% Trypsin/2.6 mM EDTA solution for 3 min. The cells were washed with PBS for three times. RNA was extracted, purified using the Qiagen RNeasy minikit, and quantified using a SpectraMaxPlus 384 UV-Visible Spectrophotometer (Molecular Devices Corp, Sunnyvale, Calif., USA). Reverse transcription was conducted using the Applied Biosystems Taqman RT protocol. Detection and quantification of mRNA were performed using the StepOnePlus Real-Time PCR System (Applied Biosystems, Carlsbad, Calif., USA). All PCR samples were referenced to the gene expression level of Glyceraldehyde 3-phosphate dehydrogenase (GAPDH).

Immunofluorescent Staining

Twenty thousand cells were seeded in a Lab-Tek II Chamber Slide System with 2 mL media overnight at 37° C. After media was removed, cells were rinsed with PBS twice and fixed with 4% formaldehyde in PBS at RT for 10 min, followed by washing with PBS. Samples were blocked with 1% BSA in PBS for 30 min in an ice bath. After BSA blocking, samples were co-stained with FITC-conjugated ICAM1 antibody and PE-conjugated EGFR antibody for 1 h and rinsed with PBS. DAPI was used to stain the cell nucleus. Immunofluorescent stained samples were dried overnight in the dark and used for fluorescent microscope imaging. Samples were examined under a Leica TCS SP5 confocal fluorescent microscope (Leica Microsystems, Buffalo Grove, Ill., USA).

Fluorescence Resonance Energy Transfer (FRET) Assay

The FRET assay was performed on live MDA-MB-231, MDA-MB-436, and MCF10A cells. $10^4$ cells were seeded in each well of 96-well plate and grown overnight. Cells were washed twice with PBS and incubated with PBS, Alexa Fluor 488-ICAM1 antibody (Donor), Alexa Fluor 555-EGFR antibody (Receptor), or a mixture of Alexa Fluor 488-ICAM1 antibody and Alexa Fluor 555-EGFR antibody (Donor+Receptor, 1:1 ratio) at a final antibody concentration of 1 μg/$10^6$ cells for 45 min at 37° C. After staining, cells were washed twice with PBS and their FRET signals were measured at the donor's excitation wavelength of 495 nm and the receptor's emission wavelength of 565 nm using a SpectraMaxPlus 384 UV-Visible Spectrophotometer (Molecular Devices Corp, Sunnyvale, Calif., USA).

Preparation of Doxorubicin Encapsulating Dual Complementary Liposome (DCL-Dox)

DCL-Dox was prepared by the extrusion method as described previously with modifications. Briefly, a lipid formulation consisted of DOPC:DSPE-PEG-COOH (95:5, mol:mol) was used to prepare liposomes. 50 mmol lipid mixture was solubilized in chloroform and dried under a dry nitrogen stream. The resulting lipid film was dissolved in 1 mL DMSO:EtOH (7:3, v:v). The lipid solution was injected into 9 mL of 240 mM sodium sulfate in phosphate buffered saline (PBS, pH 7.4) while being rigorously agitated to yield a 5 mM lipid solution. After 10 freeze-thaw cycles, lipid solution was extruded via a Northern Lipids Extruder with a 100 nm polycarbonate nanoporous membrane. After extrusion, the liposome solution was dialyzed in PBS (pH 7.4) using a Slide-A-Lyzer dialysis cassette (MWCO 20 kDa) overnight at room temperature (RT). Then Dox was added to liposome solution to reach a final concentration of 1 mg/mL, and incubated for 6 h to facilitate active loading. The resulting Dox-encapsulating liposome solution was dialyzed in PBS (pH 7.4) using a Slide-A-Lyzer dialysis cassette (MWCO 20 kDa) overnight at RT.

The surface of DCL-Dox was modified with ICAM1 and EGFR neutralizing antibodies at optimal ratios via the DSPE-PEG-COOH anchor. EDC (2 mg) and NHS (3 mg) were mixed with 1 mmol of lipid (liposomes) in PBS (pH 7.4) and incubated for 6 h at RT. A Slide-A-Lyzer dialysis cassette (MWCO 20 kDa) was used to remove unreacted EDC and NHS. Next, ICAM1 and EGFR neutralizing antibodies at different molecular ratios (1/0, 0/1, 4.2/1, 1.5/1, and 1/1) or the IgG isotype were added to EDC-modified liposomes at a molar ratio of 1:1000 (antibody:phospholipid) and incubated overnight at RT. Unreacted antibodies were removed by using a FLOAT-A-LYZER G2 dialysis tubing (MWCO 1,000 kDa). In cellular binding and internalization experiments, non-cytotoxic FITC-dextran (MW 10 kD) encapsulating liposome (DCL-FITC) was prepared and tested to replace the cytotoxic DCL-Dox. The preparation process was similar to that of DCL-Dox except that 1 mL lipid solution was added to a 9 mL FITC-dextran solution (1 mg/mL). DiR labeled DCL (DCL-DiR) was also prepared for in vivo NIR imaging experiments by adding 1 mol % DiR to the lipid composition to prepare the dry lipid film while maintaining the rest steps as the same.

The density of ICAM1 and EGFR antibodies conjugated on liposomes was quantified via microbead assay as described previously. Liposomes cannot be detected by flow cytometry because of their size, therefore, 2 μm borosilicate beads were encapsulated within DOPC:DSPE-PEG-COOH (95:5, mol:mol) liposomes by sonicating small unilamellar liposomes with microbeads in PBS for 6 h. Microbeads were rinsed three times in PBS via suspension-spin cycles to separate free liposomes. Conjugation of FITC-ICAM1 antibody, PE-EGFR antibody or PE-IgG (nonspecific binding) to microbead encapsulating liposomes was performed using EDC/NHS chemistry. Surface densities and ratios of ICAM1 and EGFR antibody conjugated to each microbead was determined with reference to Quantum Simply Cellular microbeads, which have defined numbers of antibody binding sites per bead. Liposome size and zeta potential were measured using dynamic light scattering on a Zeta-PALS analyzer (Brookhaven Instruments, Holtsville, N.Y.) in PBS (pH 7.4).

Cellular Binding and Internalization Assay

Quantitative analysis of liposome binding to TNBC cells was studied by flow cytometry analysis. $10^6$ cells were placed in each well of a 6-well cell culture plate and incubated for 4 h at 37° C. with IgG-FITC-LP, ICAM-FITC-LP, EGFR-FITC-LP, DCL-FITC_4.2/1, DCL-FITC_1.5/1, DCL-FITC_1/1, ICAM-FITC-LP/EGFR-FITC-LP mixture (4.2/1 ratio), ICAM-FITC-LP/EGFR-FITC-LP mixture (1.5/1 ratio), and ICAM-FITC-LP/EGFR-FITC-LP mixture (1/1 ratio) at a final concentration of 1 µM lipids per $10^6$ cells. All liposome-treated cells were washed with PBS, harvested using a 0.25% Trypsin/2.6 m MEDTA solution, and washed with PBS (pH 7.4) three times. Binding data were acquired using a BD FACSCalibur flow cytometer and analyzed using FlowJo software. Cellular binding and uptake of DCLs was calculated by dividing the mean fluorescence intensity of DCL-FITC treated cells by that of the IgG-FITC-LP treated cells.

The internalization ratio of DCL was evaluated using Trypan Blue quenching assay as previously reported(5, 6). Briefly, $10^6$ liposome treated cells collected for flow cytometric analysis were equally divided into two parts. One part was directly used for flow cytometric measurement, and the fluorescence intensity of liposome treated cells was defined as the total fluorescence including both extracellular and internalized DCLs. The other part was incubated with 1 mg/mL Trypan Blue solution for 30 mins to quench extracellular fluorescence and washed with PBS. The fluorescence intensity of Trypan Blue quenched cells was defined as the internalized fluorescence. The internalization ratio was calculated by dividing internalized fluorescence with total cell fluorescence times one hundred.

Cytotoxicity Assay

The cytotoxicity of DCL-Dox was evaluated using a cell viability assay. Briefly, $10^4$ cells (MDA-MB-231 and MDA-MB-436) were seeded in each well of a 96 well plate and incubated for 24 h. Then cells were treated with PBS, Free Dox, IgG-Dox-LP, ICAM-Dox-LP, EGFR-Dox-LP, and DCL-Dox at Dox concentrations ranging from 0 to 50 µg/mL for 6 h. Cells were rinsed twice with PBS and grown for 48 h. Cell viability was determined using a Dojindo cell counting kit according to the protocol provided by the manufacturer.

Cell Proliferation Assay

Five thousand cells were seeded in each well of a 96-well plate and grown overnight. Then cells were incubated with PBS, IgG-LP, ICAM-LP, EGFR-LP, and DCL at the final liposome concentration of 1 µM lipids per $10^6$ cells for 48 h. Cell proliferation was analyzed using a Dojindo cell counting kit.

Cell Invasion Assay

One million cells seeded in 6-well plate were treated with PBS, IgG-LP, ICAM-LP, EGFR-LP, and DCL at the final liposome concentration of 1 µM lipids per $10^6$ cells for 24 h, and then re-seeded onto 24-well Corning™ BioCoat™ Matrigel™ Invasion Chamber system with permeable support polycarbonate membrane (with 8 µm pore size) at a cell density of $10^5$ cell per well. DMEM without FBS and DMEM with 10% FBS were added to the upper and lower wells, respectively. Cells were allowed to invade for 20 h. Cells on the reverse side of transwell membrane facing the lower chamber after transmigrating through the 8-µm pores of transwell membrane were stained with Diff-Quik Stain Set. Four fields were counted for each sample.

Orthotopic Tumor Model and Treatments

Animal studies were performed according to the protocols approved by the Institutional Animal Care and Use Committees of Boston Children's Hospital and The City College of New York. Breast tumors were orthotopically implanted by injecting $5\times10^6$ MDA-MB-231-Luc cells into the fourth right mammary fat pad of female nude mice (Charles River, Wilmington, Mass., USA). Tumor-bearing mice were randomized into various treatment groups (n=7-10 for each group). For in vivo near infrared (NIR) fluorescent imaging experiments, tumors were allowed to develop for 2-3 weeks until they were at least 200 mm³ in volume. In vivo NIR fluorescent imaging was performed on the tumor-bearing mice that were injected intravenously with liposomes at a dosage of 20 mg lipids/kg mouse weight) using tail-vein injection. At 4, 24, and 48 h after the injection, in vivo NIR fluorescence imaging was performed using an IVIS Lumina II system (Caliper, Hopkinton, Mass., USA). At 48 h post injection, mice were sacrificed and ex vivo NIR fluorescence intensity of various organs (brain, heart, liver, lung, kidney and spleen) and excised tumors was measured using IVIS Lumina II.

For therapeutic efficacy experiments, MDA-MB-231-Luc tumors were allowed to develop for 1-2 weeks until they reached 100 mm³ in volume. Mice were randomly divided into different groups and were treated with DCL-Dox or controls at a Dox dose of 2.5 mg/kg/half-week. All treatments were performed intravenously via retro-orbital injection in 50 µL volume. Tumor growth was monitored weekly using caliper. Twenty-four days after treatment, orthotopic tumors were excised to measure their mass and various organs (brain, heart, liver, lung, kidney and spleen) were collected and analyzed for metastasis using IVIS Lumina II.

Lung Metastasis Model and Treatments

One million MDA-MB-231-Luc cells in 100 µL PBS were injected to the lateral tail vein of female nude mice to allow the formation of lung metastasis. At 24 h post injection, in vivo bioluminescence imaging was performed to confirm the localization of MDA-MB-231-Luc cells in mice lungs using an IVIS Lumina II system. Then mice were randomized into six groups (n=8 for each group) and received treatments with PBS (sham), free Dox, IgG-Dox-LP, ICAM-Dox-LP, EGFR-Dox-LP or DCL-Dox_4.2/1 (2.5 mg/kg per dosage, twice a week) for 21 days. All injections for treatments were performed intravenously via retro-orbital injection in 50 µL volume. Lung metastasis of MDA-MB-231-Luc was monitored by weekly in vivo bioluminescence imaging for up to 124 days. Mice were sacrificed and organs were excised to estimate the metastatic burden. In dosage-dependent experiments, four dosages of DCL-Dox_4.2/1 (PBS (sham), 0.625, 1.25, and 2.5 mg/kg) were tested in mice with lung metastasis using the same experimental protocol.

Chronic liver and renal toxicity of DCL-Dox were evaluated by measuring AST, ALT, Creatinine and BUN levels in mice serum after treatment. At day 74 of dosage-dependent experiments, mice were euthanized with $CO_2$ and 500 μL whole blood was collected via cardiac puncturing. Mice blood was transferred to a BD Vacutainer and incubated for 20 min at RT to allow clotting. Then serum was collected after centrifuging at 2,000 g for 10 min in a refrigerated centrifuge. Serum levels of ALT, AST, Creatinine and BUN were determined using their activity assay kits purchased from Sigma-Aldrich (St Louis, Mo., USA) with provided protocols.

Statistical Analysis

All of the experimental data were obtained in triplicate unless otherwise mentioned and are presented as mean±standard deviation. Statistical comparison by analysis of variance was performed at a significance level of $P<0.05$ based on a Student's t-test.

TABLE 5

List of cell membrane proteins

| Name | Description |
|---|---|
| ALCAM | Activated leukocyte cell adhesion molecule |
| CCR2 | Chemokine (C-C motif) receptor 2 |
| CCR5 | Chemokine (C-C motif) receptor 5 |
| CCR7 | Chemokine (C-C motif) receptor 7 |
| CD19 | CD19 molecule |
| CD20 | CD20 molecule |
| CD34 | CD34 molecule |
| CD3E | CD3e molecule, epsilon |
| CD3HIT3a | CD3 molecule, HIT3a |
| CD3OKT3 | CD3 molecule, OKT3 |
| CD44 | CD44 molecule |
| CD52 | CD52 molecule |
| CDH1 | Cadherin 1, type 1, E-cadherin (epithelial) |
| CDH2 | Cadherin 2, type 1, N-cadherin |
| CDH5 | Cadherin 5, type 2 (vascular endothelium) |
| CTLA4 | Cytotoxic T-lymphocyte-associated protein 4 |
| CXCR1 | Chemokine (C—X—C motif) receptor 1 |
| CXCR4 | Chemokine (C—X—C motif) receptor 4 |
| EGFR | Epidermal growth factor receptor |
| ENG | Endoglin |
| EPHA2 | EPH receptor A2 |
| FLT3 | Fms-related tyrosine kinase 3 |
| FOLR1 | Folate receptor 1 |
| GLUT1 | Glucose transporter 1 |
| HER2 | human epidermal growth factor receptor 2 |
| ICAM1 | Intercellular adhesion molecule 1 |
| IGFR1 | Insulin-like growth factor 1 receptor |
| IL12 | Interleukin 12 |
| IL6R | Interleukin 6 receptor |
| ITGA1 | Integrin, alpha 1 |
| ITGA2 | Integrin, alpha 2 |
| ITGA3 | Integrin, alpha 3 |
| ITGA5 | Integrin, alpha 5 |
| ITGA6 | Integrin, alpha 6 |
| ITGAL | Integrin, alpha L |
| ITGAVB3 | Integrin alpha V beta 3 |
| ITGB1 | Integrin, beta 1 |
| ITGB2 | Integrin, beta 2 |
| KIT | Mast/stem cell growth factor receptor |
| MCAM | Melanoma cell adhesion molecule |
| MET | MET proto-oncogene, receptor tyrosine kinase |
| MSLN | Mesothelin |
| MUC1 | Mucin 1, cell surface associated |
| NGFR | Nerve Growth Factor Receptor |
| NRP1 | Neuropilin 1 |
| PD1 | Programmed cell death protein 1 |
| PDGFRA | Platelet-derived growth factor receptor, alpha polypeptide |
| PDGFRB | Platelet-derived growth factor receptor, beta polypeptide |
| PDL1 | Programmed death-ligand 1 |
| PECAM1 | Platelet/endothelial cell adhesion molecule 1 |
| PROM1 | Prominin 1 |
| PSMA | Prostate-specific membrane antigen |
| PTPRC | Protein tyrosine phosphatase, receptor type, C |
| RANKL | Receptor activator of nuclear factor kappa-B ligand |
| SELE | Selectin E |
| SELP | Selectin P |
| SSEA4 | Stage specific embryonic antigen 4 |
| TFRC | Transferrin receptor |
| THY1 | Thy-1 cell surface antigen |
| TIE2 | TEK tyrosine kinase, endothelial |
| TIM1 | T-cell immunoglobulin and mucin domain 1 |
| TIM3 | T-cell immunoglobulin and mucin-domain 3 |
| TIM4 | T-cell immunoglobulin and mucin-domain 4 |
| UPAR | Plasminogen activator, urokinase receptor |
| VCAM1 | Vascular cell adhesion molecule 1 |
| VEGFR1 | Vascular endothelial growth factor receptor 1 |
| VEGFR2 | Vascular endothelial growth factor receptor 2 |
| VEGFR3 | Vascular endothelial growth factor receptor 3 |

TABLE 6

ICAM1 and EGFR surface density and ratio on human TNBC cells

| Cell line | ICAM1 surface density (molecules/cell) | EGFR surface density (molecules/cell) | Total surface density (molecules/cell) | ICAM1/EGFR Protein Ratio |
|---|---|---|---|---|
| MDA-MB-231 | 2,350,000 ± 25,000 | 559,000 ± 1,200 | 2,909,000 | 4.2:1 |
| MDA-MB-436 | 758,000 ± 7,600 | 514,000 ± 2,000 | 1,270,000 | 1.5:1 |
| MDA-MB-157 | 751,000 ± 4,400 | 406,000 ± 8,900 | 1,157,000 | 1.8:1 |
| MCF10A | 93,000 ± 2,300 | 61,200 ± 740 | 154,200 | 1.5:1 |

TABLE 7

Dynamic light scattering characterization of DCL-Dox and controls

| Sample | Size (nm) | PDI | Zeta-potential (mV) | Dox Encapsulation Efficiency (%) |
|---|---|---|---|---|
| IgG-Dox-LP | 128 ± 32 | 0.050 | −10.8 ± 0.7 | 98.1 ± 2.2 |
| ICAM1-Dox-LP | 123 ± 21 | 0.022 | −8.2 ± 1.9 | 97.8 ± 0.7 |
| EGFR-Dox-LP | 125 ± 25 | 0.026 | −8.0 ± 0.6 | 97.6 ± 2.3 |
| DCL-Dox_4.2/1 | 132 ± 20 | 0.015 | −6.3 ± 1.6 | 98.6 ± 2.2 |
| DCL-Dox_1.5/1 | 133 ± 26 | 0.022 | −5.6 ± 0.7 | 98.5 ± 0.4 |
| DCL-Dox_1/1 | 132 ± 13 | 0.009 | −6.2 ± 0.9 | 97.9 ± 2.9 |

The foregoing written specification is considered to be sufficient to enable one skilled in the art to practice the disclosure. The present disclosure is not to be limited in scope by examples provided, since the examples are intended as a single illustration of one or more aspects of the disclosure and other functionally equivalent embodiments are within the scope of the disclosure.

Various modifications of the disclosure in addition to those shown and described herein will become apparent to those skilled in the art from the foregoing description and fall within the scope of the appended claims. The advantages and objects of the disclosure are not necessarily encompassed by each embodiment of the disclosure.

ACKNOWLEDGEMENT

The support from the Breast Cancer Research Foundation in making this invention is acknowledged.

What is claimed is:

1. A liposome comprising:
   (i) a lipid bilayer;
   (ii) an EGFR antibody conjugated to the liposome surface;
   (iii) an ICAM-1 antibody conjugated to the liposome surface; and
   (iv) a therapeutic agent encapsulated in the liposome,
   wherein the ratio of ICAM-1 antibody to EGFR antibody complements the ratio of ICAM-1 to EGFR protein on the surface of a triple negative breast cancer (TNBC) cell and the ratio is between 1 and 5.
2. The liposome of claim 1, wherein the lipid bilayer comprises a neutral lipid.
3. The liposome of claim 2, wherein the neutral lipid is 1,2-dioleoyl-sn-glycero-3-phosphocholine (DOPC).
4. The liposome of claim 1, wherein the lipid bilayer comprises an anionic lipid.
5. The liposome of claim 1, wherein the lipid bilayer further comprises a functionalized lipid.
6. The liposome of claim 5, wherein the functionalized lipid is a lipid-polymer conjugate.
7. The liposome of claim 5, wherein the functionalized lipid is 1,2-distearoyl-sn-glycero-3-phosphoethanolamine-N-[carboxy(polyethylene glycol)-2000]-COOH (DSPE-PEG-COOH).
8. The liposome of claim 1, wherein the functionalized lipid is up to 10% of total lipids in the liposome.
9. The liposome of claim 1, wherein the EGFR ligand or the ICAM-1 ligand is conjugated to the functionalized lipid.
10. The liposome of claim 1, wherein the lipid bilayer further comprises a pH-responsive lipid.
11. The liposome of claim 10, wherein the pH-responsive lipid comprises 1,2-dioleoyl-3-dimethylammoniumpropane (DODAP).
12. The liposome of claim 1, wherein the ratio of ICAM-1 antibody to EGFR antibody is 1.5 or 4.2.
13. The liposome of claim 1, wherein the therapeutic agent is an anticancer agent.
14. A pharmaceutical composition comprising the liposome of claim 1.
15. A method of treating triple negative breast cancer (TNBC), the method comprising administering to a subject in need thereof a therapeutically effective amount of the liposome of claim 1.

* * * * *